United States Patent
Bunnage et al.

(10) Patent No.: US 6,916,927 B2
(45) Date of Patent: Jul. 12, 2005

(54) PYRAZOLOPYRIMIDINONES WHICH INHIBIT TYPE 5 CYCLIC GUANOSINE 3',5'-MONOPHOSPHATE PHOSPHODIESTERASE (CGMP-PDE5) FOR THE TREATMENT OF SEXUAL DYSFUNCTION

(75) Inventors: Mark Edward Bunnage, Sandwich (GB); John Paul Mathias, Sandwich (GB); Stephen Derek Albert Street, Sandwich (GB); Anthony Wood, Sandwich (GB)

(73) Assignee: Pfizer Inc.

( * ) Notice: Subject to any disclaimer, the term of this patent is extended or adjusted under 35 U.S.C. 154(b) by 0 days.

(21) Appl. No.: 10/808,027

(22) Filed: Mar. 23, 2004

(65) Prior Publication Data

US 2004/0180944 A1 Sep. 16, 2004

Related U.S. Application Data

(62) Division of application No. 09/402,229, filed as application No. PCT/EP98/02257 on Apr. 10, 1998, now Pat. No. 6,723,719.

(30) Foreign Application Priority Data

| Apr. 25, 1997 | (GB) | ............................................. 9708406 |
| Jul. 22, 1997 | (GB) | ............................................. 9715380 |
| Oct. 30, 1997 | (GB) | ............................................. 9722954 |

(51) Int. Cl.[7] ...................... C07D 295/26; C07D 231/02

(52) U.S. Cl. ....................................... 544/358; 544/366

(58) Field of Search .............................. 544/358, 366

(56) References Cited

U.S. PATENT DOCUMENTS

| 3,992,441 A | 11/1976 | Helland ........................ 260/518 |
| 4,663,326 A | 5/1987 | Hamilton ..................... 514/258 |
| 4,666,908 A | 5/1987 | Hamilton ..................... 514/229 |
| 4,668,280 A | 5/1987 | Gehring et al. ................ 71/92 |
| 4,871,843 A | 10/1989 | Roger et al. ................. 540/575 |
| 5,250,534 A | 10/1993 | Bell et al. ................... 514/258 |
| 5,272,147 A | 12/1993 | Bell et al. ................ 514/234.2 |
| 5,294,612 A | 3/1994 | Bacon et al. ............ 514/234.2 |
| 5,346,901 A | 9/1994 | Bell et al. ................... 514/258 |
| 5,426,107 A | 6/1995 | Bell et al. ................... 514/23.4 |
| 5,719,283 A | 2/1998 | Bell et al. ................... 544/262 |
| 5,734,053 A | 3/1998 | Terrett ........................ 544/277 |
| 5,736,548 A | 4/1998 | Bacon et al. ............... 514/258 |
| 5,955,611 A | 9/1999 | Dunn et al. ................. 544/262 |

FOREIGN PATENT DOCUMENTS

| EP | 0201188 | 12/1986 | ......... C07D/487/04 |
| EP | 0352960 | 1/1990 | ........... C07D/31/52 |
| EP | 0371731 | 6/1990 | ......... C07D/239/91 |
| EP | 0442204 | 8/1991 | ......... C07D/487/04 |
| EP | 0463756 | 1/1992 | ......... C07D/487/04 |
| EP | 0526004 | 2/1992 | ......... C07D/487/04 |
| EP | 0579496 | 1/1994 | ......... C07D/401/04 |
| EP | 0349239 | 3/1994 | ......... C07D/487/04 |
| EP | 0636626 | 2/1995 | ......... C07D/487/04 |
| WO | WO 9306104 | 4/1993 | ......... C07D/487/04 |
| WO | WO 9307149 | 4/1993 | ......... C07D/487/04 |

(Continued)

OTHER PUBLICATIONS

DuMaitre et al., J. Med. Chem. 39(8), 1996, 1635–1644.
Bowman et al., Br. J. Pharmacol., 1984, 81(4), p. 665.
Am. J. Physiol, 1993, 264(2), p H419.

(Continued)

*Primary Examiner*—Venkataraman Balasubramanian
(74) *Attorney, Agent, or Firm*—Peter C. RIchardson; Gregg C. Benson; Martha G. Munchhof

(57) ABSTRACT

Compounds of formulae (IA) and (IB) or pharmaceutically or veterinarily acceptable salts thereof, or pharmaceutically or veterinarily acceptable solvates of either entity, wherein $R^1$ is $C_1$ to $C_3$ alkyl substituted with $C_3$ to $C_6$ cycloalkyl, $CONR^5R^6$ or a N-linked heterocyclic group; $(CH_2)_n$Het or $(CH_2)_n$Ar, $R^2$ is $C_1$ to $C_6$ alkyl; $R^3$ is $C_1$ to $C_6$ alkyl optionally substituted with $C_1$ to $C_4$ alkoxy; $R^4$ is $SO_2NR^7R^8$; $R^5$ and $R^6$ are each independently selected from H and $C_1$ to $C_4$ alkyl optionally substituted with $C_1$ to $C_4$ alkoxy, or, together with the nitrogen atom to which they are attached, form a 5- or 6-membered heterocyclic group; $R^7$ and $R^8$, together with the nitrogen atom to which they are attached, form a 4-$R^{10}$-piperazinyl group; $R^{10}$ is H or $C_1$ to $C_4$ alkyl optionally substituted with OH, $C_1$ to $C_4$ alkoxy or $CONH_2$; Het is an optionally substituted C-linked 5- or 6-membered heterocyclic group; Ar is optionally substituted phenyl; and n is 0 or 1; are potent and selective cGMP PDE5 inhibitors useful in the treatment of, inter alia, male erectile dysfunction and female sexual dysfunction (IA)

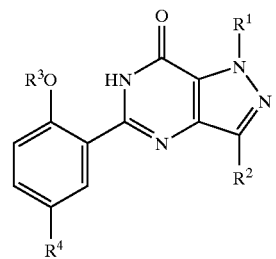

(IB)

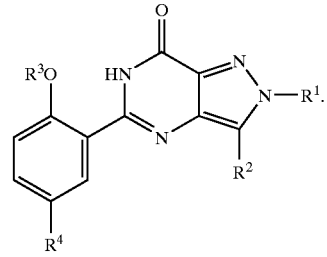

2 Claims, No Drawings

FOREIGN PATENT DOCUMENTS

| | | | |
|---|---|---|---|
| WO | WO 9312095 | 6/1993 | ......... C07D/239/91 |
| WO | WO 9315062 | 8/1993 | ......... C07D/241/04 |
| WO | WO 9400453 | 1/1994 | ......... C07D/473/30 |
| WO | WO 9405661 | 3/1994 | ......... C07D/471/04 |
| WO | WO 9428902 | 12/1994 | ......... A61K/31/505 |
| WO | WO 9616644 | 6/1996 | .......... A61K/31/00 |
| WO | WO 9616657 | 6/1996 | ......... A61K/31/505 |
| WO | WO 9628429 | 9/1996 | ......... C07D/239/70 |
| WO | WO 9628448 | 9/1996 | ......... C07D/487/04 |
| WO | WO 9849166 | 11/1998 | ......... C07D/487/04 |
| WO | WO 9954333 | 10/1999 | ......... C07D/487/04 |
| WO | WO 9964004 | 12/1999 | ......... A61K/31/505 |

OTHER PUBLICATIONS

Rajfer et al., New Eng. J. Med., 1992, 326(2), p. 90.
J. Urol., 1993, 149(4), p. 285A.
Murray, Drug News & Perspective, 1993, 6(23), p. 150.
Sohn et al., Int. J. Imp. Res., 1992, 4(S2), p. 11.
J. Urol., 1992, 147(S4), p. 454A.
Harriet W. Hamilton, et al., J. Med. Chem. 1987, 30, p. 91–96.
Czarniecki et al in Annual Reports in Medicinal Chemistry, 31, 61–70.
Henze et al., J. Am. Chems. Soc., Feb., 1939, pp. 433–435.
Terfort et al., J. Chem.. Soc., Perkin Trans. 1, 1996, pp. 1467–1479.

PYRAZOLOPYRIMIDINONES WHICH INHIBIT TYPE 5 CYCLIC GUANOSINE 3',5'-MONOPHOSPHATE PHOSPHODIESTERASE (CGMP-PDE5) FOR THE TREATMENT OF SEXUAL DYSFUNCTION

CROSS REFERENCE TO RELATED APPLICATIONS

This application is a divisional of U.S. patent application Ser. No. 09/402,229, filed Sep. 29, 1999, now U.S. Pat. No. 6,723,719 which was a National Phase filing under 35 USC §371 of PCT/EP98/02257, filed Apr. 10, 1998, and which claimed foreign priority to GB 9708406.5, filed Apr. 25, 1997, GB 9715380.3, filed Jul. 22, 1997, and GB 9722954.6, filed Oct. 30, 1997.

This invention relates to a series of pyrazolo[4,3-d]pyrimidin-7-ones, which inhibit cyclic guanosine 3',5'-monophosphate phosphodiesterases (cGMP PDEs). More notably, the compounds of the invention are potent and selective inhibitors of type 5 cyclic guanosine 3',5'-monophosphate phosphodiesterase (cGMP PDE5) and have utility therefore in a variety of therapeutic areas.

In particular, the compounds are of value in the treatment of male erectile dysfunction (MED) and female sexual dysfunction (FSD) but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, conditions of reduced blood vessel patency e.g. post-percutaneous transluminal coronary angioplasty (post-PTCA), peripheral vascular disease, stroke, bronchitis, allergic asthma, chronic asthma, allergic rhinitis, glaucoma and diseases characterised by disorders of gut motility, e.g. irritable bowel syndrome (IBS).

WO-A-94/28902 and WO-A-96/16644 relate to the use of various series of cGMP PDE inhibitors for the treatment of MED including, within the latter, the compounds disclosed in EP-A-0201188 which are also adenosine receptor antagonists and reported to be useful in the treatment of cardiovascular disorders as well as the compounds disclosed in EP-A-0352960 which have bronchodilator, vasodilator and anti-allergic properties.

Thus the invention provides compounds of formulae (IA) and (IB):

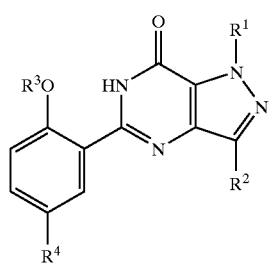

(IA)

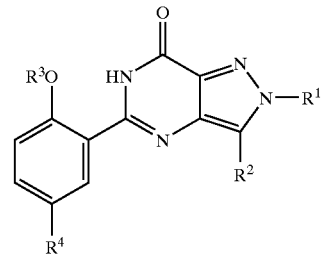

(IB)

or a pharmaceutically or veterinarily acceptable salt thereof, or a pharmaceutically or veterinarily acceptable solvate of either entity, wherein $R^1$ is $C_1$ to $C_3$ alkyl substituted with $C_3$ to $C_6$ cycloalkyl, $CONR^5R^6$ or a N-linked heterocyclic group selected from pyrazolyl, imidazolyl, triazolyl, pyrrolidinyl, piperidinyl, morpholinyl and 4-$R^9$-piperazinyl; $(CH_2)_n$Het or $(CH_2)_n$Ar;

$R^2$ is $C_1$ to $C_5$ alkyl;

$R^3$ is $C_1$ to $C_5$ alkyl optionally substituted with $C_1$–$C_4$ alkoxy;

$R^4$ is $SO_2NR^7R^8$;

$R^5$ and $R^6$ are each independently selected from H and $C_1$ to $C_4$ alkyl optionally substituted with $C_1$ to $C_4$ alkoxy, or, together with the nitrogen atom to which they are attached, form a pyrrolidinyl, piperidinyl, morpholinyl or 4-$R^9$-piperazinyl group;

$R^7$ and $R^8$, together with the nitrogen atom to which they are attached, form a 4-$R^{10}$-piperazinyl group;

$R^9$ is $C_1$ to $C_4$ alkyl;

$R^{10}$ is H or $C_1$ to $C_4$ alkyl optionally substituted with OH, $C_1$ to $C_4$ alkoxy or $CONH_2$;

Het is a C-linked 6-membered heterocyclic group containing one or two nitrogen atoms, optionally in the form of its mono-N-oxide, or a C-linked 5-membered heterocyclic group containing from one to four heteroatoms selected from nitrogen, oxygen and sulphur, wherein either of said heterocyclic groups is optionally substituted with one or two substituents selected from $C_1$ to $C_4$ alkyl optionally substituted with $C_1$ to $C_4$ alkoxy, $C_1$ to $C_4$ alkoxy, halo and $NH_2$;

Ar is phenyl optionally substituted with one or two substituents selected from $C_1$ to $C_4$ alkyl, $C_1$ to $C_4$ alkoxy, halo, CN, $CONH_2$, $NO_2$, $NH_2$, $NHSO_2$ ($C_1$ to $C_4$ alkyl) and $SO_2NH_2$;

and n is 0 or 1.

In the above definition, unless otherwise indicated, alkyl and alkoxy groups having three or more carbon atoms may be straight chain or branched chain. Halo means fluoro, chloro, bromo or iodo.

The compounds of formulae (IA) and (IB) may contain one or more chiral centres and therefore can exist as stereoisomers, i.e. as enantiomers or diastereoisomers, as well as mixtures thereof. The invention includes both the individual stereoisomers of the compounds of formulae (IA) and (IB) and any mixture thereof. Separation of diastereoisomers may be achieved by conventional techniques, e.g. by fractional crystallisation or chromatography (including HPLC) of a diastereoisomeric mixture of a compound of formula (IA) or (IB) or a suitable salt or derivative thereof. An individual enantiomer of a compound of formula (IA) or (IB) may be prepared from a corresponding optically pure intermediate or by resolution, either by HPLC of the racemate using a suitable chiral support or, where appropriate, by fractional crystallisation of the diastereoisomeric salts formed by reaction of the racemate with a suitable optically active acid or base.

The compounds of formulae (IA) and (IB) may also exist in tautomeric forms and the invention includes both mixtures thereof and the individual tautomers.

Also included in the invention are radiolabelled derivatives of compounds of formulae (IA) and (IB) which are suitable for biological studies.

The pharmaceutically or veterinarily acceptable salts of the compounds of formulae (IA) and (IB) which contain a basic centre are, for example, non-toxic acid addition salts formed with inorganic acids such as hydrochloric, hydrobromic, sulphuric and phosphoric acid, with organo-carboxylic acids, or with organo-sulphonic acids. Compounds of formulae (IA) and (IB) can also provide pharmaceutically or veterinarily acceptable metal salts, in particular non-toxic alkali metal salts, with bases. Examples include the sodium and potassium salts.

A preferred salt is the citrate.

A preferred group of compounds of formulae (IA) and (IB) is that wherein $R^1$ is $C_1$ to $C_2$ alkyl substituted with $C_3$ to $C_5$ cycloalkyl, $CONR^5R^6$ or a N-linked heterocyclic group selected from pyrazolyl, triazolyl, morpholinyl and 4-$R^9$-piperazinyl; $(CH_2)_n$Het or $(CH_2)_n$Ar; $R^5$ is H and $R^6$ is $C_1$ to $C_4$ alkyl optionally substituted with $C_1$ to $C_4$ alkoxy or $R^5$ and $R^6$, together with the nitrogen atom to which they are attached, form a morpholinyl group; Het is selected from pyridinyl, 1-oxidopyridinyl, pyridazinyl, pyrimidinyl, pyrazinyl, imidazolyl, isoxazolyl, thiazolyl, triazolyl and oxadiazolyl, any of which is optionally substituted with one or two substituents selected from $CH_3$, $CH_2CH_2OCH_3$, $OCH_3$ and $NH_2$; and $R^2$, $R^3$, $R^4$, $R^9$, Ar and n are as previously defined.

A more preferred group of compounds of formulae (IA) and (IB) is that wherein $R^1$ is $C_1$ to $C_2$ alkyl substituted with cyclobutyl, $CONR^5R^6$, pyrazol-1-yl, 1,2,3-triazol-1-yl, 1,2,4-triazol-1-yl, morpholin-4-yl or 4-methylpiperazin-1-yl; pyrimidin-2-yl; $CH_2$Het or $(CH_2)_n$Ar; $R^2$ is $C_1$ to $C_3$ alkyl; $R^3$ is $C_1$ to $C_3$ alkyl optionally substituted with $C_1$ to $C_2$ alkoxy; $R^5$ is H and $R^6$ is $C_1$ to $C_2$ alkyl optionally substituted with $C_1$ to $C_2$ alkoxy or $R^5$ and $R^6$, together with the nitrogen atom to which they are attached, form a morpholin-4-yl group; $R^{10}$ is $C_1$ to $C_2$ alkyl optionally monosubstituted with OH, $OCH_3$ or $CONH_2$; Het is selected from pyridin-2-yl, 1-oxidopyridin-2-yl, pyridin-3-yl, pyridazin-3-yl, pyridazin-4-yl, pyrimidin-4-yl, pyrimidin-5-yl, pyrazin-2-yl, 3-methoxypyridin-2-yl, 6-aminopyridin-2-yl, 1-methylimidazol-2-yl, 3,5-dimethylisoxazol-4-yl, 2-methylthiazol-4-yl, 1-methyl-1,2,4-triazol-5-yl, 1-(2-methoxyethyl)-1,2,4-triazol-5-yl, 4-methyl-1,2,4-triazol-3-yl, 3-methyl-1,2,4-triazol-5-yl, 1,2,4-oxadiazol-3-yl and 5-methyl-1,2,4-oxadiazol-3-yl; Ar is selected from phenyl, 4-chlorophenyl, 4-bromophenyl, 2-cyanophenyl, 2-carbamoylphenyl, 4-carbamoylphenyl, 2-nitrophenyl, 4-nitrophenyl, 2-aminophenyl, 4-aminophenyl, 2-methanesulphonamidophenyl, 4-methanesulphonamidophenyl, 4-ethanesulphonamidophenyl, 4-(prop-2-ylsulphonamido)phenyl and 4-sulphamoylphenyl; and n is as previously defined.

A particularly preferred group of compounds of formulae (IA) and (IB) is that wherein $R^1$ is cyclobutylmethyl, morpholin-4-ylcarbonylmethyl, 2-(morpholin-4-yl)ethyl, pyrimidin-2-yl, $CH_2$Het or $(CH_2)_n$Ar; $R^2$ is $CH_2CH_3$ or $CH_2CH_2CH_3$; $R^3$ is $CH_2CH_3$, $CH_2CH_2CH_3$ or $CH_2CH_2OCH_3$; $R^{10}$ is $CH_3$, $CH_2CH_3$ or $CH_2CH_2OH$; Het is selected from pyridin-2-yl, pyridazin-3-yl, pyrazin-2-yl, 3-methoxypyridin-2-yl, 6-aminopyridin-2-yl, 1-methylimidazol-2-yl, 3,5-dimethylisoxazol-4-yl, 1-methyl-1,2,4-triazol-5-yl, 1-(2-methoxyethyl)-1,2,4-triazol-5-yl and 5-methyl-1,2,4-oxadiazol-3-yl; Ar is selected from phenyl, 2-aminophenyl, 2-methanesulphonamidophenyl, 4-methanesulphonamidophenyl, 4-ethanesulphonamidophenyl and 4-(prop-2-ylsulphonamido)phenyl; and n is as previously defined.

Especially preferred individual compounds of the invention include

5-{5-[4-(2-hydroxyethyl)piperazin-1-ylsulphonyl]-2-n-propoxyphenyl}-3-n-propyl-1-(pyridin-2-yl)methyl-1,6-dihydro-7H-pyrazolo[4,3-d]pyrimidin-7-one;

1-(1-methylimidazol-2-yl)methyl-5-[5-(4-methylpiperazin-1-ylsulphonyl)-2-n-propoxyphenyl]-3-n-propyl-1,6-dihydro-7H-pyrazolo[4,3-d]pyrimidin-7-one;

5-{5-[4-(2-hydroxyethyl)piperazin-1-ylsulphonyl]-2-n-propoxyphenyl}-3-n-propyl-2-(pyridin-2-yl)methyl-2,6-dihydro-7H-pyrazolo[4,3-d]pyrimidin-7-one;

5-[5-(4-ethylpiperazin-1-ylsulphonyl)-2-n-propoxyphenyl]-3-n-propyl-2-(pyridin-2-yl)methyl-2,6-dihydro-7H-pyrazolo[4,3-d]pyrimidin-7-one;

3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one;

5-[5-(4-ethylpiperazin-1-ylsulphonyl)-2-n-propoxyphenyl]-3-n-propyl-2-(pyridazin-3-yl)methyl-2,6-dihydro-7H-pyrazolo[4,3-d]pyrimidin-7-one;

5-[5-(4-ethylpiperazin-1-ylsulphonyl)-2-n-propoxyphenyl]-3-n-propyl-2-(pyrazin-2-yl)methyl-2,6-dihydro-7H-pyrazolo[4,3-d]pyrimidin-7-one; and 5-[2-ethoxy-5-(4-ethylpiperazin-1-ylsulphonyl)phenyl]-3-n-propyl-2-(pyridin-2-yl)methyl-2,6-dihydro-7H-pyrazolo[4,3-d]pyrimidin-7-one.

In a further aspect, the present invention provides processes for the preparation of compounds of formulae (IA) and (IB), their pharmaceutically and veterinarily acceptable salts, and pharmaceutically and veterinarily acceptable solvates of either entity, as illustrated below.

It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps.

Illustrative of protecting group strategies are the routes to the syntheses of Example 56 in which alcohol protection using a t-butyldimethylsilyl group precedes the desired N-mesylation step, Example 63 in which the piperazine 4-position is Boc(t-butoxycarbonyl)-protected to preclude bis-sulphonylation of the piperazine, and Examples 23 and 68 in which amine protection using a pivaloyl group precedes the penultimate chlorosulphonation step.

It will also be appreciated that various standard substituent or functional group interconversions and transformations within certain compounds of formulae (IA) and (IB) will provide other compounds of formulae (IA) and (IB). Examples include alkoxide exchange at the 2-position of the 5-phenyl substituent (see conversion of Example 41 to Example 42), hydrolysis of cyano to carbamoyl (see conversion of Example 46 to Example 47), reduction of nitro to amino (see conversions of Examples 49, 50, 51, 91, 115, 118 and 121 to Examples 52, 53, 54, 93, 116, 119 and 122 respectively), sulphonylation of amino (see conversions of Examples 52, 54, 116, 119 and 122 to Examples 55, 57, 117, 120, and 123 and 124 respectively), hydrogenolysis of halo (see conversion of Example 88 to Example 87) and N-oxidation of pyridinyl. (see conversions of Examples 6 and 12 to Examples 128 and 129 respectively).

Moreover, certain compounds of formulae (IA) and (IB) maybe prepared directly from the corresponding 4-unsubstituted piperazine analogues, that is compounds of formulae (IA) and (IB) wherein $R^{10}$ is hydrogen, using standard alkylation procedures.

The following processes are illustrative of the general synthetic procedures which may be adopted in order to obtain the compounds of the invention.

1. A compound of formula (IA) or (IB) may be prepared from a compound of formula (IIA) or (IIB) respectively:

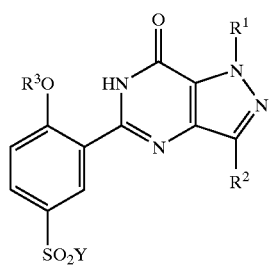
(IIA)

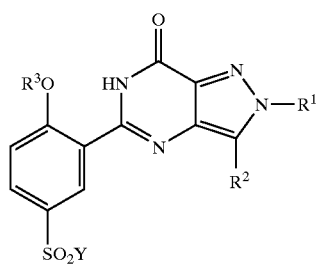
(IIB)

wherein Y is halo, preferably chloro, and $R^1$, $R^2$ and $R^3$ are as previously defined for formulae (IA) and (IB), by reaction with a compound of formula (III):

$R^7R^8NH$        (III)

wherein $R^7$ and $R^8$ are as previously defined for formulae (IA) and (IB).

The reaction is generally conducted at room temperature, preferably in the presence of an appropriate solvent such as a $C_1$ to $C_3$ alkanol, using an excess of (III) or other suitable base to scavenge the acid by-product (HY).

A compound of formula (IIA) or (IIB) may be prepared from a compound of formula (IVA) or (IVB) respectively:

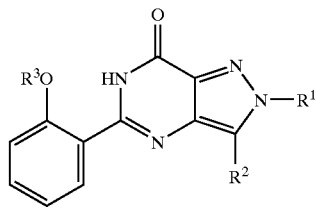
(IVA)

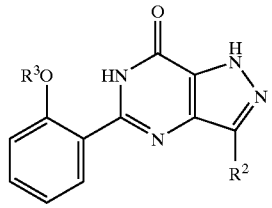
(IVB)

wherein $R^1$, $R^2$ and $R^3$ are as previously defined for formulae (IIA) and (IIB), by the application of known methods for the introduction of a $SO_2Y$ group, wherein Y is also as previously defined for formulae (IIA) and (IIB), into an aromatic ring system. For example, when Y is chloro, by the action of excess chlorosulphonic acid, optionally followed by excess thionyl chloride, at from about 0° C. to about room temperature.

A compound of formula (IVA) or (IVB) may be prepared by alkylation of a compound of formula (V):

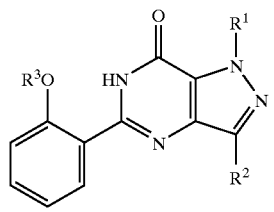
(V)

wherein $R^2$ and $R^3$ are as previously defined for formulae (IVA) and (IVB), using one or more of a plethora of well-known methods, such as:

(i) reaction of (V) with a compound of formula $R^1X$, wherein $R^1$ is as previously defined for formulae (IVA) and (IVB), and X is a suitable leaving group, e.g. halo (preferably chloro, bromo or iodo), $C_1$–$C_4$ alkanesulphonyloxy, trifluoromethanesulphonyloxy or arylsulphonyloxy (such as benzenesulphonyloxy or p-toluenesulphonyloxy), in the presence of an appropriate base, optionally in the presence of sodium iodide or potassium iodide, at from about −70° C. to about 100° C. Preferably the alkylation is conducted at from about room temperature to about 80° C.

Suitable base-solvent combinations may be selected from (a) sodium, potassium or cesium carbonate, sodium or potassium bicarbonate, or a tertiary amine such as triethylamine or pyridine, together with a $C_1$ to $C_4$ alkanol, 1,2-dimethoxyethane, tetrahydrofuran, 1,4-dioxan, acetonitrile, pyridine, dimethylformamide or N,N-dimethylacetamide;

(b) sodium or potassium hydroxide, or a sodium or potassium $C_1$ to $C_4$ alkoxide, together with a $C_1$ to $C_4$ alkanol, water or mixtures thereof;

(c) lithium, sodium or potassium hydride, lithium, sodium or potassium bis(trimethylsilyl)amide, lithium diisopropylamide or butyllithium, together with toluene, ether, 1,2-dimethoxyethane, tetrahydrofuran or 1,4-dioxan; or (d) under phase transfer catalysis conditions, a tetraalkylammonium halide or hydroxide, together with a mixture of an aqueous solution of sodium or potassium hydroxide and dichloromethane, 1,2-dichloroethane or chloroform;

(ii) reaction of (V) with a compound of formula $R^1OH$, wherein $R^1$ is as previously defined for formulae (IVA)

and (IVB), using classical Mitsunobu methodology. Typical reaction conditions involve treating (V) with the alkanol in the presence of a triarylphosphine and a di($C_1$ to $C_4$)alkyl azodicarboxylate, in a suitable solvent such as tetrahydrofuran or 1,4-dioxan, at from about −5° C. to about room temperature.

Certain compounds of formulae (IVA) and (IVB) may be obtained less directly from related analogues, when these are more readily accessible, using the alkylation methods previously described: see, for example, the hydrogenolytic transformation of Preparation 33, wherein $R^1$ is 2,4-dichloropyrimidin-5-ylmethyl, to Preparation 34, wherein $R^1$ is pyrimidin-5-ylmethyl. Similarly, the amides of Preparations 102, 103 and 104 and of Preparations 105, 106 and 107 are obtained from the corresponding carboxylic acids of Preparations 101 and 69 respectively.

Other compounds of formulae (IVA) and (IVB), wherein $R^1$ is $CH_2Het$, may be prepared by construction of the heterocyclic ring subsequent to the pyrazolopyrimidinone-alkylation step. This approach is particularly convenient when the required $HetCH_2X$ is relatively inaccessible. For example, when Het is either 3-methyl-1,2,4-triazol-5-yl or 5-methyl-1,2,4-oxadiazol-3-yl, the heterocyclic rings can be assembled from a carboxymethyl precursor and a cyanomethyl precursor respectively, i.e. a compound of formula (IVA) and (IVB) wherein $R^1$ is $CH_2CO_2H$ or $CH_2CN$, by a series of conventional steps. Each alternative is illustrated by the transformations of Preparation 69 to Preparation 72 and of Preparations 73 and 77 to Preparations 76 and 79.

Yet another variation for obtaining a compound of formula (IVA) or (IVB) is to incorporate the $R^1$ group at a much, earlier stage in the synthetic pathway, e.g. by generating a suitably $N^1$- or $N^2$-alkylated pyrazole derivative, which is then processed to (IVA) or (IVB) by analogy with the subsequently described conversion of (VII) to (V).

A compound of formula (V) may be obtained from a compound of formula (VI):

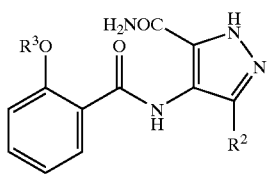

(VI)

wherein $R^2$ and $R^3$ are as previously defined for formula (V), by the application of known cyclisation methods for pyrimidinone ring formation. Thus, for example, the cyclisation may be effected by the treatment of (V) with a base such as sodium or potassium hydroxide, or sodium or potassium carbonate, optionally in the presence of hydrogen peroxide, in a $C_1$ to $C_4$ alkanol-water medium at from about 60° C to the reflux temperature of the reaction mixture.

The cyclisation may also be mediated by a sodium or potassium $C_1$ to $C_5$ alkoxide, in a $C_1$ to $C_5$ alkanol as solvent, at from about 60° C. to the reflux temperature of the reaction mixture.

Alternative cyclisation procedures include the treatment of (V) with either polyphosphoric acid at from about 130 to about 150° C. or with a Lewis acid, e.g. anhydrous zinc chloride at from about 200 to about 220° C.

A compound of formula (VI) may be obtained by selective N-acylation of a compound of formula (VII):

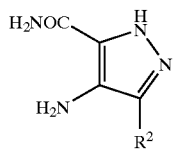

(VII)

wherein $R^2$ is as previously defined for formula (VI), with a compound of formula (VIII):

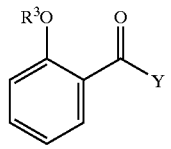

(VIII)

wherein Y is a suitable leaving group, and $R^3$ is as previously defined for formula (VI). For example, when Y is chloro, the reaction may be conducted with the appropriate aroyl chloride in the presence of an excess of a tertiary amine such as triethylamine or pyridine to act as scavenger for the acid by-product (HY), optionally in the presence of a catalyst such as 4-dimethylaminopyridine, in a suitable solvent such as dichloromethane, at from about 0° C. to about room temperature. For convenience, pyridine may also be used as the solvent.

2. An alternative, generally applicable, synthetic route to compounds of formulae (IA) and (IB) involves the incorporation of the R substituent at an earlier stage of the synthesis.

Thus a compound of formula (IA) or (IB) may be prepared by cyclisation of a compound of formula (IXA) or (IXB) respectively:

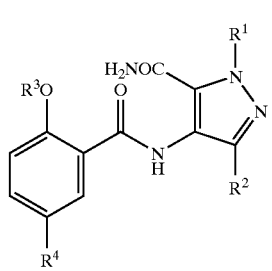

(IXA)

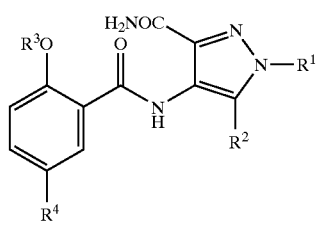

(IXB)

wherein $R^1$, $R^2$, $R^3$ and $R^4$ are as previously defined for formulae (IA) and (IB). The cyclisation may be effected under basic, neutral or acidic conditions.

Under neutral conditions, a compound of formula (IXA) or (IXB) may be heated, optionally in the presence of a solvent and/or optionally in the presence of a dehydrating agent and/or mechanical water-removal system, e.g. a Dean-Stark apparatus. A suitable solvent is 1,2-dichlorobenzene, sulpholane or N-methylpyrrolidin-2-one, a suitable dehydrating agent is molecular sieves and, preferably, the reaction is carried out at from 180 to 220° C.

Under acidic conditions, the cyclisation may be carried out by reaction of a compound of formula (IXA) or (IXB) with a protic acid or Lewis acid, optionally in the presence of a solvent. A suitable protic acid is concentrated sulphuric acid, phosphoric acid or p-toluenesulphonic acid, a suitable Lewis acid is boron trifluoride, aluminium chloride, silicon tetrachloride, stannic chloride, titanium tetrachloride, ferric chloride or zinc chloride, a suitable solvent is glacial acetic acid, tetrahydrofuran, 1,4-dioxan or chlorobenzene and, preferably, the reaction is carried out at from 65 to 210° C.

However, the preferred mode of cyclisation of a compound of formula (IXA) or (IXB) is under basic conditions, preferably in a solvent, optionally in the presence of hydrogen peroxide or a peroxide salt, and is followed, where necessary, by neutralisation of the reaction mixture. A suitable base is selected from the group consisting of the $C_1$–$C_{12}$ alkoxide and hydride salts of lithium, sodium and potassium, sodamide, sodium cyclohexylamide and cesium carbonate, the quantity of base employed is from 1.1 to 2.0 molecular equivalents, a suitable solvent is selected from the group consisting of ethanol, n-propanol, t-butanol, t-amyl alcohol, 1-methylcyclohexanol, tetrahydrofuran and 1,4-dioxan, and the reaction is carried out at from 60 to 105° C.

Preferably the base is selected from the group consisting of sodium ethoxide, sodium t-butoxide, potassium t-butoxide and sodium hydride; and the solvent is selected from the group consisting of ethanol, n-propanol, t-butanol, t-amyl alcohol and tetrahydrofuran.

A compound of formula (IXA) or (IXB) may be prepared by reaction of a compound of formula (XA) or (XB) respectively:

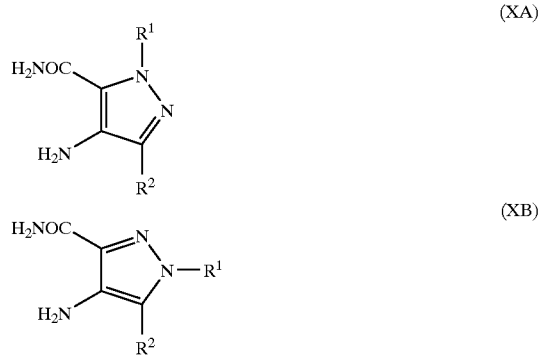

wherein $R^1$ and $R^2$ are as previously defined for formulae (IXA) and (IXB) with a compound of formula (XI):

wherein $R^3$ and $R^4$ are also as previously defined for formulae (IXA) and (IXB).

The coupling reaction may be achieved using conventional amide bond-forming techniques, e.g. via the acyl chloride derivative of (XI), by analogy with the preparation of a compound of formula (VI), ensuring that any potentially vulnerable substituent (for example when $R^{10}$ is $C_1$ to $C_4$ alkyl substituted with OH or $CONH_2$) is appropriately protected.

In particular, any one of a host of amino acid coupling variations may be used. For example, the acid of formula (XI) may be activated using a carbodiimide such as 1,3-dicyclohexylcarbodiimide or 1-ethyl-3-(3-dimethylaminoprop-1-yl)carbodiimide optionally in the presence of 1-hydroxybenzotriazole and/or a catalyst such as 4-dimethylaminopyridine, or by using a halotrisaminophosphonium salt such as bromotris(pyrrolidino)phosphonium hexafluorophosphate. Either type of coupling is conducted in a suitable solvent such as dichloromethane, optionally in the presence of a tertiary amine such as N-methylmorpholine or N-ethyldiisopropylamine (for example when either the compound of formula (XA) or (XB), or the activating reagent, is presented in the form of an acid addition salt), at about 0° C. Preferably, from 1.1 to 2.0 molecular equivalents of the activating reagent and from 2.0 to 3.0 molecular equivalents of any tertiary amine present are employed.

Preferably, a mixture of (XI) and either (XA) or (XB) is treated with about one molecular equivalent of the coupling reagent (benzotriazol-1-yloxy)tripyrrolidinophosphonium hexafluorophosphate (PyBOP) in a suitable solvent such as dimethylformamide at about room temperature.

In a further variation, the carboxylic acid function of (XI) may first of all be activated using up to about a 5% excess of a reagent such as N,N'-carbonyidiimidazole in a suitable solvent, e.g. ethyl acetate or butan-2-one, at from about room temperature to about 80° C., followed by reaction of the intermediate imidazolide with either (XA) or (XB) at from about 20 to about 90° C.

The amines of formula (III), the 4-aminopyrazole-5-carboxamides of formulae (VII), (XA) and (XB), the carboxylic acid derivatives of formula (VIII) and the carboxylic acids of formula (XI), when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formulae (IA) and (IB) to be obtained.

The pharmaceutically acceptable acid addition salts of the compounds of formulae (IA) and (IB) which contain a basic centre may also be prepared in a conventional manner. For example a solution of the free base is treated with the appropriate acid, either neat or in a suitable solvent, and the resulting salt isolated either by filtration of by evaporation under vacuum of the reaction solvent. Pharmaceutically acceptable base addition salts can be obtained in an analogous manner by treating a solution of a compound of formula (IA) or (IB) with the appropriate base. Both types of salt may be formed or interconverted using ion-exchange resin techniques.

The biological activities of the compounds of the present invention were determined by the following test methods.

Phosphodiesterase (PDE) Inhibitory Activity

In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE$^4$) from human skeletal muscle; and the photoreceptor PDE (PDE6) from bovine retina.

Assays were performed using a modification of the "batch" method of W. J. Thompson et al. (Biochem., 1979, 18, 5228). Results from these tests show that the compounds of the present invention are potent and selective inhibitors of cGMP-specific PDE5.

Functional Activity

This was assessed in vitro by determining the capactiy of a compound of the invention to enhance sodium nitroprusside-induced relaxation of pre-contracted rabbit corpus cavernosum tissue strips, as described by S. A. Ballard M al. (Brit. J. Pharmacol., 1996, 118 (suppl.), abstract 153P).

In Vivo Activity

Compounds were screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

In human therapy, the compounds of formulae (IA) and (IB), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example intracavernosally, intravenously, intramuscularly or subcutaneously. For parenteral administration, they are best used in the form of a sterile aqueous solution which may contain other substances, for example enough salts or monosaccharides to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formulae (IA) and (IB) and their pharmaceutically acceptable salts and solvates may be from 10 to 500 mg (in single or divided doses). Thus, for example, tablets or capsules may contain from 5 to 100 mg of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention.

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 25 to 100 mg of compound when required. In circumstances where the recipient suffers from a swallowing disorder or from impairment of drug absorption after oral administration, the drug may be administered parenterally, e,g. sublingually or buccally.

For veterinary use, a compound of formula (IA) or (IB), or a veterinarily acceptable salt thereof, or a veterinarily acceptable solvate of either entity, is administered as a suitably acceptable formulation in accordance with normal veterinary practice and the veterinary surgeon will determine the dosing regimen and route of administration which will be most appropriate for a particular animal.

Thus the invention provides a pharmaceutical composition comprising a compound of formula (IA) or (IB), or a pharmaceutically acceptable salt thereof, or a pharmaceutically acceptable solvate of either entity, together with a pharmaceutically acceptable diluent or carrier.

It further provides a veterinary formulation comprising a compound of formula (IA) or (IB), or a veterinarily acceptable salt thereof, or a veterinarily acceptable solvate of either entity, together with a veterinarily acceptable diluent or carrier.

The invention also provides a compound of formula (IA) or (IB), or a pharmaceutically acceptable salt thereof, or a pharmaceutically acceptable solvate of either entity, or a pharmaceutical composition containing any of the foregoing, for use as a human medicament.

In addition, it provides a compound of formula (IA) or (IB), or a veterinarily acceptable salt thereof, or a veterinarily acceptable solvate of either entity, or a veterinary formulation containing any of the foregoing, for use as an animal medicament.

In yet another aspect, the invention provides the use of a compound of formula (IA) or (IB), or a pharmaceutically acceptable salt thereof, or a pharmaceutically acceptable solvate of either entity, for the manufacture of a human medicament for the curative or prophylactic treatment of a medical condition for which a cGMP PDE5 inhibitor is indicated.

It also provides the use of a compound of formula (IA) or (IB), or a veterinarily acceptable salt thereof, or a veterinarily acceptable solvate of either entity, for the manufacture of an animal medicament for the curative or prophylactic treatment of a medical condition for which a cGMP PDE5 inhibitor is indicated.

Moreover, the invention provides the use of a compound of formula (IA) or (IB), or a pharmaceutically acceptable salt thereof, or a pharmaceutically acceptable solvate containing either entity, for the manufacture of a human medicament for the curative or prophylactic treatment of male erectile dysfunction, female sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility.

It also provides the use of a compound of formula (IA) or (IB), or a veterinarily acceptable salt thereof, or a veterinarily acceptable solvate containing either entity, for the manufacture of an animal medicament for the curative or prophylactic treatment of male erectile dysfunction, female sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility.

Additionally, the invention provides a method of treating or preventing a medical condition for which a cGMP PDE5 inhibitor is indicated, in a mammal (including a human being), which comprises administering to said mammal a therapeutically effective amount of a compound of formula (IA) or (IB), or a pharmaceutically or. veterinarily acceptable salt thereof, or a pharmaceutically or veterinarily acceptable solvate of either entity, or a pharmaceutical composition or veterinary formulation containing any of the foregoing.

Still further, the invention provides a method of treating or preventing male erectile dysfunction, female sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility in a mammal (including a human being), which comprises administering to said mammal a therapeutically effective amount of a compound of formula (IA) or (IB), or a pharmaceutically or veterinarily acceptable salt thereof, or a pharmaceutically or veterinarily acceptable solvate of either entity, or a pharmaceutical composition or veterinary formulation containing any of the foregoing.

The invention also includes any novel intermediates described herein, for example those of formulae (IIA), (IIB), (IVA), (IVB), (IXA) and (IXB).

The syntheses of the compounds of the invention and of the intermediates for use therein are illustrated by the following Examples and Preparations.

$^1$H Nuclear magnetic resonance (NMR), spectra were recorded using either a Varian Unity 300 or a Varian Inova 400 spectrometer and were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; b, broad.

Mass spectra (m/z) were recorded using a Fisons Instruments Trio mass spectrometer in the thermospray ionisation mode.

Room temperature means 20 to 25° C.

EXAMPLE 1

Aminosulphonylation of 1/2-alkylated-5-(2-alkoxyphenyl)-3-alkyl-1/2,6-dihydro-7H-pyrazolo[4,3-d]pyrimidin-7-ones Chlorosulphonic acid (30 mmol) was added slowly to an ice-cooled sample of either the N1- or the N2-alkylated substrate (3 mmol), followed by thionyl chloride (4.5 mmol), then the resulting mixture was allowed to warm to room temperature and stirred for 24 hours. The reaction mixture was ice-cooled and carefully poured into stirred ice/water, then the precipitate was collected and dried by suction to give the crude sulphonyl chloride which was of sufficient purity to use directly in the subsequent N-sulphonylation step.

Excess (generally from 2 to 5 mol. equiv.) 1-substituted piperazine was added portionwise to a stirred mixture of the sulphonyl chloride and ethanol. The reaction mixture was stirred for 20 hours at room temperature and then evaporated under reduced pressure. The residue was partitioned between ethyl acetate and saturated aqueous sodium bicarbonate solution, then the organic phase separated and combined with three ethyl acetate extracts of the aqueous phase. The combined organic solutions were dried ($Na_2SO_4$) and evaporated under reduced pressure to provide the crude sulphonamide, which was purified by column chromatography on silica gel.

In cases where the sulphonyl chloride did not precipitate on ice-water quenching of the chlorosulphonation reaction mixture, the resulting aqueous solution was diluted with an equal volume of ethanol, ice-cooled and treated with the appropriate piperazine derivative as described above.

EXAMPLE 2

3-Ethyl-5-[5-(4-ethylpiperazin-1-ylsulphonyl)-2-n-propoxyphenyl]-1-(pyridin-2-yl)methyl-1,6-dihydro-7H-pyrazolo[4,3-d]pyrimidin-7-one Obtained as a white solid (40%) from the title compound of Preparation 16 and 1-ethylpiperazine using the procedure of Example 1. Found: C, 59.06; H, 6.19; N, 17.00. $C_{28}H_{35}N_7O_4S$ requires C, 59.45; H, 6.24; N, 17.33% δ($CDCl_3$): 1.02 (3H, t), 1.18 (3H, t), 1.42 (3H, t), 2.02 (2H, m), 2.40 (2H, q), 2.54 (4H, m), 3.02 (2H, q), 3.12 (4H, m), 4.25 (2H, t), 5.93 (2H, s), 7.00 (1H, d), 7.17 (2H, m), 7.60 (1H, m), 7.84 (1H, d), 8.58 (1H, d), 8.88 (1H, s), 10.92 (1H, s). LRMS: m/z 566 (M+1)$^+$.

EXAMPLE 3

5-[5-(4-Methylpiperazin-1-ylsulphonyl)-2-n-propoxyphenyl]-3-n-proyl-1-(pyridin-2-yl)methyl-1,6-dihydro-7H-pyrazolo[4,3-d]pyrimidin-7-one Obtained as a white solid (62%) from the title compound of Preparation 17 and 1-methylpiperazine using the procedure of Example 1. sound: C, 59.51; H, 6.42; N, 16.67. $C_{28}H_{35}N_7O_4S$ requires C, 59.45; H. 6.24; N, 17.33%. δ ($CDCl_3$): 0.98 (3H, t), 1.18 (3H, t), 1.87(2H, m), 2.02 (2H, m), 2.28 (3H, s), 2.50 (4H, m), 2.96 (2H, t), 3.14 (4H, m), 4.25 (2H, t), 5.92 (2H, s), 6.98 (1H, d), 7.16 (2H, m), 7.60 (1H, m), 7.84 (1H, d), 8.57 (1H, d), 8.88 (1H, s), 10.90 (1 H, s). LRMS: m/z 566 (M+1)$^+$.

EXAMPLE 4

5-{5-[4-(2-Hydroxyethyl)piperazin-1-ylsulphonyl]-2-n-propoxyphenyl}-3-n-propyl-1-(pyridin-2-yl)methyl-1,6-dihydro-7H-pyrazolo[4,3-d]pyrimidin-7-one Obtained as a white foam (12%) from the title compound of Preparation 17 and 1-(2-hydroxyethyl)piperazine using the procedure of Example 1. Found: C, 58.18; H, 6.25; N, 15.81. $C_{29}H_{37}N_7O_5S$ requires C, 58.47; H, 6.26; N, 16.46%. δ ($CDCl_3$): 1.00 (3H, t), 1.18 (3H, t), 1.88 (2H, m), 2.04 (2H, m), 2.30 (1H, s), 2.58 (2H, m), 2.66 (4H, m), 2.98 (2H, t), 3.13 (4H, m), 3.58 (2H, t), 4.28 (2H, t), 5.96 (2H, s), 7.00 (1H, d), 7.18 (2H, m), 7.60 (1H, m), 7.86 (1H, d), 8.58 (1H, d), 8.90 (1H, s), 10.94 (1H, s). LRMS: m/z 596 (M+1)$^+$.

EXAMPLE 5A

3-Ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (a) Obtained as a white solid (30%) from the title compound of Preparation 18 and 1-ethylpiperazine using the procedure of Example 1. Found: C, 58.92; H, 6.34; N, 17.03. $C_{28}H_{35}N_7O_4S$ requires C, 59.45; H, 6.24; N, 17.33%. δ (CDCl$_3$): 1.02 (3H, t), 1.14 (3H, t), 1.30 (3H, t), 2.02 (2H, m), 2.40 (2H, q), 2.52 (4H, m), 3.04 (2H, q), 3.08 (4H, m), 4.23 (2H, t), 5.68 (2H, s), 7.08 (1H, d), 7.15 (1H, d), 7.20 (1H, m); 7.62 (1H, m), 7.82 (1H, d), 8.58 (1H, d), 8.78 (1H, s), 10.60 (1H, s). LRMS: m/z 566 (M+1)$^+$.

(b) A stirred mixture of the title compound of Preparation 136 (385.1 g, 0.66 mol) and n-propanol (1932 ml) was distilled under reduced pressure until approximately half the volume (990 ml) of n-propanol had been removed, then cooled to about 37° C. under nitrogen. Potassium t-butoxide (222.2 g, 1.98 mol) was added portionwise over 15 minutes and the reaction mixture heated under reflux for 26 hours, allowed to cool, treated with water (1932 ml) and filtered. The pH of the filtrate was adjusted to 7.5 using 1M hydrochloric acid (1840 ml), then the solid precipitate granulated for 30 minutes, collected, washed with water and dried to give the title compound (275.2 g, 73.7%) as a white solid. δ(DMSOd$_6$): 0.92 (6H, m), 1.19 (3H, t), 1.72 (2H, m), 2.25 (2H, q), 2.39 (4H, m), 2.88 (4H, m), 2.96 (2H, q), 4.11 (2H, t), 5.68 (2H, s), 7.21 (1H, d) 7.34 (3H, m), 7.80 (2H, m), 7.87 (1H, s), 8.51 (1 H, d), 11.72 (1H, s). LRMS: m/z 566 (M+1)$^+$.

EXAMPLE 5B

3-Ethyl-5-[5-(4-ethylpiperazin-1-sulphonyl)-2-n-propoxyphenyl]-2-(pyridin-2-yl)methyl-2,6-dihydro-7H-pyrazolo[4,3-d]pyrimidin-7-one citrate A stirred mixture of the title compound of Example 5A (15.0 g, 26.5 mmol) and acetone (150 ml) was heated under reflux, then filtered. To the stirred filtrate was added a filtered solution of citric acid (5.10 g, 26.5 mmol) in a mixture of acetone (75 ml) and water (7.5 ml), then the reaction mixture heated under reflux for 75 minute and allowed to cool. The resulting suspension was granulated for 1 hour and filtered, then the solid thus obtained washed with acetone (20 ml) and dried at 45° C. to provide the title compound (18.33 g, 91%) as a white solid, m.p. 185° C. Found: C, 53.84; H, 5.71; N, 12.89. $C_{28}H_{35}N_7O_4S$; $C_6H_8O_7$ requires C, 53.89; H, 5.72; N, 12.94. δ(DMSOd$_6$): 0.95 (6H, m), 1.20 (3H, t), 1.72 (2H, m), 2.40–2.73 (10H, m), 2.96 (4H, m), 4.11 (2H, t), 5.68 (2H, s), 7.21 (1H, d), 7.34 (2H, m), 7.82(3H, m), 8.51 (1H, d), 11.72 (1H, s).

EXAMPLE 6

5-[5-(4-Methylpiperazin-1-ylsulphonyl)-2-n-propoxyphenyl]-3-n-propyl-2-(pyridin-2-yl)methyl-2,6-dihydro-7H-pyrazolo[4,3-d]pyrimidin-7-one Obtained as a white solid (53%) from. the title compound of Preparation 20 and 1-methylpiperazine using the procedure of Example 1. Found: C, 58.96; H, 6.23; N, 17.03. $C_{28}H_{35}N_7O_4S$ requires C, 59.45; H, 6.24; N, 17.33%. δ (CDCl$_3$): 0.96 (3H, t), 1.16 (3H, t), 1.76 (2H, m), 2.04 (2H, m), 2.26 (3H, s), 2.50 (4H, m), 2.98 (2H, t), 3.10 (4H, m), 4.25 (2H, t), 5.66 (2H, s), 7.06 (1H, d), 7.15 (1H, d), 7.22 (1H, m), 7.64 (1H, m), 7.83 (1H, d), 8.58 (1H, d), 8.78 (1H, s), 10.60 (1H, s). LRMS: m/z 566 (M+1)$^+$.

EXAMPLE 7

5-{5-[4-(2-Hydroxyethyl)piperazin-1-ylsulphonyl]-2-n-propoxyphenyl}-3-n-propyl-2-(pyridin-2-yl)methyl-2,6-dihydro-7H-pyrazolo[4,3-d]pyrimidin-7-one Obtained as a white foam (30%) from the title compound of Preparation 20 and 1-(2-hydroxyethyl)piperazine using the procedure of Example 1. Found: C, 57.84; H, 6.44; N, 15.99. $C_{29}H_{37}N_7O_5S$; 0.10 $CH_2Cl_2$ requires C, 57.85; H, 6.21; N, 16.23%. δ (CDCl$_3$): 0.95 (3H, t), 1.17 (3H, t), 1.75 (2H, m), 2.04 (2H, m), 2.28 (1H, s), 2.54 (2H, t), 2.60 (4H, m), 2.98 (2H, t), 3.10 (4H, m), 3.58 (2H, m), 4.25 (2H, t), 5.68 (2H, s), 7.07 (1H, d), 7.17 (1H, d), 7.20 (1H, m), 7.62 (1H, m), 7.83 (1H, d), 8.58 (1H, d), 8.78 (1H, s), 10.62 (1H, s). LRMS: m/z 596 (M+1)$^+$.

EXAMPLE 8

3-Ethyl-5-[5-(4-methylpiperazin-1-ylsulphonyl)-2-n-propoxyphenyl]-2-(pyridin-2-yl)methyl-2,6-dihydro-7H-pyrazolo[4,3-d]pyrimidin-7-one Obtained as a white solid (35%) from the title compound of Preparation 18 and 1-methylpiperazine using the procedure of Example 1. Found: C, 58.24; H, 6.06; N, 17.53. $C_{27}H_{33}N_7O_4S$ requires C, 58.79; H, 5.99; N, 17.78%. δ (CDCl$_3$): 1.12 (3H, t), 1.26 (3H, t), 1.99 (2H, m), 2.24 (3H, s), 2.45 (4H, m), 2.98 (2H, q), 3.06 (4H, m), 4.20 (2H, t), 5.65 (2H, s), 7.04 (1H, d), 7.12 (1H, d), 7.18 (1H, m), 7.60 (1H, m), 7.78 (1H, d), 8.54 (1H, d), 8.74 (1H, s), 10.57 (1H, s). LRMS: m/z 552 (M+1)$^+$.

EXAMPLE 9

3-Ethyl-5-{5-[4-(2-hydroxyethyl)piperazin-1-ylsulphonyl]-2-n-propoxyphenyl}-2-(pyridin-2-yl)methyl-2,6-dihydro-7H-pyrazolo[4,3-d]pyrimidin-7-one Obtained as a white solid (30%) from the title compound of Preparation 18 and 1-(2-hydroxyethyl)piperazine using the procedure of Example 1. Found: C, 56.11; H, 6.10; N, 16.15. $C_{28}H_{35}N_7O_5S$; $H_2O$ requires C, 56.08; H, 6.22; N, 16.35%. δ (CDCl$_3$): 1.12 (3H, t), 1.30 (3H, t), 2.00 (2H, m), 2.26 (1H, s), 2.52 (2H, t), 2.57 (4H, m), 3.00 (2H, q), 3.06 (4H, m), 3.54 (2H, m), 4.20 (2H, t), 5.64 (2H, s), 7.04 (1H, d), 7.13 (1H, d), 7.58 (1H, m), 7.78 (1H, m), 8.53 (1H, d), 8.76 (1H, s), 10.58 (1H, s). LRMS: m/z 582 (M+1)$^+$.

EXAMPLE 10

5-[2-Ethoxy-5-(4-methylpiperazin-1-ylsulphonyl)phenyl]-3-n-propyl-2-(pyridin-2-yl)methyl-2,6-dihydro-7H-pyrazolo[4,3-d]pyrimidin-7-one Obtained as a white foam (32%) from the title compound of Preparation 19 and 1-methylpiperazine using the procedure of Example 1. Found: C, 57.82; H, 6.08; N, 17.19%. $C_{27}H_{33}N_7O_4S$; 0.20 $CH_2Cl_2$ requires C, 57.45; H, 5.92; N, 17.24%. δ (CDCl$_3$): 0.95 (3H, t), 1.65 (3H, t), 1.77 (2H, m), 2.28 (3H, s), 2.50 (4H, m), 2.98 (2H, t), 3.10 (4H, m), 4.38 (2H, q), 5.68 (2H, s), 7.08 (1H, d), 7.15 (1H, d), 7.23 (1H, m), 7.64 (1H, m), 7.84 (1H, d), 8.58 (1H, d), 8.80 (1H, s), 10.62 (1H, s). LRMS: m/z 552 (M+1)$^+$.

EXAMPLE 11

5-[2-Ethoxy-5-(4-ethylpiperazin-1-ylsulphonyl)phenyl]-3-n-propyl-2-(pyridin-2-yl)methyl-2,6-dihydro-7H-pyrazolo[4,3-d]pyrimidin-7-one Obtained as a white solid (35%) from the title compound of Preparation 19 and 1-ethylpiperazine using the procedure of Example 1. Found: C, 58.93; H, 6.24; N, 17.09. $C_{28}H_{35}N_7O_4S$ requires C, 59.45; H, 6.24; N, 17.33%. δ ($CDCl_3$): 0.90 (3H, t), 0.98 (3H, t), 1.60 (2H, m), 1.72 (2H, m), 2.36 (2H, q), 2.50 (4H, m), 2.94 (2H, t), 3.06 (4H, m), 4.34 (2H, q), 5.65 (2H, s), 7.05 (1H, d), 7.10 (1H, d), 7.18 (1H, m), 7.58 (1H, m), 7.80 (1H, d), 8.54 (1H, d), 8.76 (1H, s), 10.58 (1 H, s). LRMS: m/z 566 $(M+1)^+$.

EXAMPLE 12

5-[5-(4-Ethylpiperazin-1-ylsulphonyl)-2-n-propoxyphenyl]-3-n-propyl-2-(pyridin-2-yl)methyl-2,6-dihydro-7H-pyrazolo[4,3-d]pyrimidin-7-one Obtained as a white foam (42%) from the title compound of Preparation 20 and 1-ethylpiperazine using the procedure of Example 1. Found: C, 59.46; H, 6.44; N, 16.53. $C_{29}H_{37}N_7O_4S$; 0.35 $H_2O$ requires C, 59.44; H, 6.48; N, 16.73%. δ ($CDCl_3$): 0.94 (3H, t), 1.03 (3H, t), 1.18 (3H, t), 1.76 (2H, m), 2.04 (2H, m), 2.41 (2H, q), 2.53 (4H, m), 3.00 (2H, t), 3.12 (4H, m), 4.25 (2H, t), 5.67 (2H, s), 7.08 (1H, d), 7.15 (1H, d), 7.23 (1H, m), 7.63 (1H, m), 7.83 (1H, d), 8.58 (1H, d), 8.79 (1H, s), 10.60 (1H, s). LRMS: m/z 580 $(M+1)^+$.

EXAMPLE 13

5-[5-(4-Ethylpiperazin-1-ylsulphonyl)-2-n-propoxyphenyl]-3-n-propyl-2-(pyridin-3-yl)methyl-2,6-dihydro-7H-pyrazolo[4,3-d]pyrimidin-7-one Obtained as a white foam (39%) from the title compound of Preparation 21 and 1-ethylpiperazine using the procedure of Example 1. Found: C, 59.25; H, 6.47; N, 16.73. $C_{29}H_{37}N_7O_4S$; 0.25 $CH_2Cl_2$ requires C, 59.65; H, 6.40; N, 16.79%. δ ($CDCl_3$): 0.92 (3H, t), 0.98 (3H, t), 1.14 (3H, t), 1.74 (2H, m), 2.00 (2H, m), 2.37 (2H, q), 2.50 (4H, m), 2.88 (2H, t), 3.05 (4H, m), 4.20 (2H, t), 5.54 (2H, s), 7.10 (1H, d), 7.22 (1H, m), 7.53 (1H, m), 7.79 (1H, d), 8.54 (2H, m), 8.74 (1H, s), 10.58 (1H, s). LRMS: m/z 580 $(M+1)^+$.

EXAMPLE 14

3-Ethyl-5-[5-(4-ethylpiperazin-1-ylsulphonyl)-2-n-propoxyphenyl]-2-(pyridazin-3-yl)methyl-2,6-dihydro-7H-pyrazolo[4,3-d]pyrimidin-7-one Obtained as a solid (40%) from the title compound of Preparation 29 and 1-ethylpiperazine using the procedure of Example 1. Found: C, 55.73; H, 6.07; N, 18.93. $C_{27}H_{34}N_8O_4S$; 0.75 $H_2O$ requires C, 55.89; H, 6.17; N, 19.31%. δ ($CDCl_3$): 1.10 (3H, t), 1.15 (3H, t), 1.34 (3H, t), 2.04 (2H, m), 2.40 (2H, q), 2.50 (4H, m), 3.08 (6H, m), 4.24 (2H, t), 5.88 (2H, s), 7.15 (1H, d), 7.46 (2H, m), 7.82 (1H, d), 8.76 (1H, s), 9.15 (1H, d), 10.60 (1H, s). LRMS: m/z 567 $(M+1)^+$.

EXAMPLE 15

5-[5-(4-Ethylpiperazin-1-ylsulphonyl)-2-n-propoxyphenyl]-3-n-propyl-2-(pyridazin-3-yl)methyl-2,6-dihydro-7H-pyrazolo[4,3-d]pyrimidin-7-one Obtained as a white solid (32%) from the title compound of Preparation 30 and 1-ethylpiperazine using the procedure of Example 1. Found: C, 57.61; H, 6.11; N, 19.10. $C_{28}H_{36}N_8O_4S$ requires C, 57.91; H, 6.25; N, 19.30%. δ ($CDCl_3$): 0.92 (3H, t), 0.98 (3H, t), 1.12 (3H, t), 1.75 (2H, m), 2.00 (2H, m), 2.37 (2H, q), 2.48 (4H, m), 3.00 (2H, t), 3.05 (4H, m), 4.20 (2H, t), 5.87 (2H, s), 7.12 (1H, d), 7.42 (1H, m), 7.46 (1H, d), 7.80 (1H, d), 8.74 (1H, s), 9.12 (1H, d), 10.62 (1H, s). LRMS: m/z 581 $(M+1)^+$.

EXAMPLE 16

5-[5-(4-Ethylpiperazin-1-ylsulphonyl)-2-n-propoxyphenyl]-3-n-propyl-2-(pyridazin-4-yl)methyl-2,6-dihydro-7H-pyrazolo[4,3-d]pyrimidin-7-one Obtained as a pale brown solid (20%) from the title compound of Preparation 31 and 1-ethylpiperazine using the procedure of Example 1. δ ($CDCl_3$): 1.01 (6H, m), 1.18 (3H, t), 1.87 (2H, m), 2.04 (2H, m), 2.41 (2H, q), 2.55 (4H, m), 2.95 (2H, t), 3.12 (4H, m), 4.26 (2H, t), 5.80 (2H, s), 7.15 (1H, d), 7.40 (1H, d), 7.86 (1H, d), 8.85 (1H, s), 9.14 (1H, d), 9.20 (1H, s), 10.99 (1H, s). LRMS: m/z 581 $(M+1)^+$.

EXAMPLE 17

5-[5-(4-Ethylpiperazin-1-ylsulphonyl)-2-n-propoxyphenyl]-3-n-propyl-2-(pyrimidin-4-yl)methyl-2,6-dihydro-7H-pyrazolo[4,3-d]pyrimidin-7-one Obtained as a foam (58%) from the title compound of Preparation 32 and 1-ethylpiperazine using the procedure of Example 1. Found: C, 57.31; H, 6.21; N, 18.98. $C_{28}H_{36}N_8O_4S$ requires C, 57.91; H, 6.25; N, 19.30%. δ ($CDCl_3$): 0.92 (3H, t), 0.97 (3H, t), 1.12 (3H;t), 1.73 (2H, m), 2.00 (2H, m), 2.38 (2H, q), 2.59 (4H, m), 2.92 (2H, t), 3.04 (4H, m), 4.20 (2H, t), 5.60 (2H, s), 6.96 (1H, d), 7.12 (1H, d), 7.80 (1H, d), 8.64 (1H, d), 8.75 (1H, s), 10.63 (1H, s). LRMS: m/z 581 $(M+1)^+$.

EXAMPLE 18

5-[5-(4-Ethylpiperazin-1-ylsulphonyl)-2-n-propoxyphenyl]-3-n-propyl-2-(pyrimidin-5-yl)methyl-2,6-dihydro-7H-pyrazolo[4,3-d]pyrimidin-7-one Obtained as a cream foam (44%) from the title compound of Preparation 34 and 1-ethylpiperazine using the procedure of Example 1. Found: C, 57.00; H, 6.20; N, 18.42. $C_{28}H_{36}N_8O_4S$; 0.15 $CH_2Cl_2$ requires C, 56.98; H, 6.17; N. 18.88%. δ ($CDCl_3$): 0.99 (6H, m), 1.11 (3H, t), 1.78 (2H, m), 2.00 (2H, m), 2.37 (2H, q), 2.50 (4H, m), 2.94 (2H, m), 3.05 (4H, m), 4.21 (2H, t), 5.51 (2H, s), 7.10 (1H, d), 7.80 (1H, d), 8.64 (2H, s), 8.75 (1H, s), 9.15 (1H, s), 10.64 (1H, s). LRMS: m/z 581 $(M+1)^+$.

EXAMPLE 19

3-Ethyl-5-[5-(4-ethylpiperazin-1-ylsulphonyl)-2-n-propoxyphenyl]-2-(pyrazin-2-yl)methyl-2.6-dihydro-7H-pyrazolo[4,3-d]pyrimidin-7-one Obtained as an off-white foam (47%) from the title compound of Preparation 35 and 1-ethylpiperazine using the procedure of Example 1. δ ($CDCl_3$): 1.01 (3H, t), 1.15 (3H, t), 1.37 (3H, t), 2.02 (2H, m), 2.39 (2H,q), 2.50 (4H, m), 3.08 (6H, m), 4.24 (2H, t), 5.70 (2H, s), 7.15 (1H, d), 7.82 (1H, d), 8.52 (3H, m), 8.78 (1H, s), 10.60 (1H, s). LRMS: m/z 567 $(M+1)^+$.

EXAMPLE 20

5-[5-(4-Ethylpiperazin-1-ylsulphonyl)-2-n-propoxyphenyl]-3-n-propyl-2-(pyrazin-2-yl)methyl-2,6-dihydro-7H-pyrazolo[4,3-d]pyrimidin-7-one Obtained as a white solid (37%) from the title compound of Preparation 36 and 1-ethylpiperazine using the procedure of Example 1. Found: C, 56.80; H, 6.11; N, 18.84. $C_{28}H_{36}N_8O_4S$; 0.80 $H_2O$ requires C, 56.51; H, 6.37; N, 18.83%. δ ($CDCl_3$): 0.99 (6H, m), 1.10 (3H, t), 1.78 (2H, m), 2.00 (2H, m), 2.38 (2H, q), 2.48 (4H, m), 3.00 (2H, t), 3.05 (4H, m), 4.22 (2H, t), 5.68 (2H, s), 7.14 (1H, d), 7.80 (1H, d), 8.47 (1 H, s), 8.50 (2H, s), 8.74 (1H, s), 10.62 (1H, s). LRMS: 581 $(M+1)^+$.

EXAMPLE 21

5-[2-Methoxy-5-(4-methylpiperazin-1-ylsulphonyl) phenyl]-3-n-propyl-1-(pyridin-2-yl)methyl-1,6-dihydro-7H-pyrazolo[4,3-d]pyrimidin-7-one Obtained as a white crystalline solid (15%) from the title compound of. Preparation 41 and 1-methylpiperazine using the procedure of Example 1. Found: C, 57.93; H, 5.75; N, 18.00. $C_{26}H_{31}N_7O_4S$ requires C, 58.10; H, 5.77; N, 18.25%. δ ($CDCl_3$): 1.00 (3H, t), 1.87 (2H, m), 2.30 (3H, s), 2.50 (4H, m), 2.98 (2H, m), 3.12 (4H, m), 4.12 (3H, s), 5.96 (2H, s), 7.00 (1H, d), 7.18 (2H, m), 7.60 (1H, m), 7.88 (1H, d), 8.58 (1H, d), 8.85 (1H, s), 10.68 (1H, s). LRMS: m/z 538 $(M+1)^+$.

EXAMPLE 22

5-[5-(4-Ethylpiperazin-1-ylsulphonyl)-2-n-propoxyphenyl]-1-(3-methoxypyridin-2-yl)methyl-3-n-propyl-1,6-dihydro-7H-pyrazolo[4,3-d]pyrimidin-7-one Obtained as a white solid (27%) from the title compound of Preparation 47 and 1-ethylpiperazine using the procedure of Example 1. Found: C, 58.83; H, 6.48; N, 15.76. $C_{30}H_{39}N_7O_5S$ requires C, 59.09; H, 6.45; N, 16.08%. δ ($CDCl_3$): 1.00 (6H, m), 1.18 (3H, t), 1.87 (2H, m), 2.02 (2H, m), 2.40 (2H, q), 2.56 (4H, m), 2.96 (2H, t), 3.13 (4H, m), 3.84 (3H, s), 4.24 (2H, t), 5.98 (2H, s), 7.14 (3H, m), 7.83 (1H, d), 8.02 (1H, d), 8.87 (1H, s), 10.80 (1H, s). LRMS: m/z 610 $(M+1)^+$.

EXAMPLE 23

1-(6-Aminopyridin-2-yl)methyl-5-[5-(4-ethylpiperazin-1-ylsulphonyl)-2-n-propoxyphenyl]-3-n-propyl-1,6-dihydro-7H-pyrazolo[4,3-d]pyrimidin-7-one Obtained as a white solid (44%) from the title compound of Preparation 50 and 1-ethylpiperazine using the procedure of Example 1. Found: C, 58.31; H, 6.45; N, 18.52. $C_{29}H_{38}N_8O_4S$ requires C, 58.57; H, 6.44; N, 18.84%. δ ($CDCl_3$): 1.02 (6H, m), 1.17 (3H, t), 1.88 (2H, m), 2.05 (2H, m), 2.42 (2H, q), 2.56 (4H, m), 2.98 (2H, t), 3.14 (4H, m), 4.25 (2H, t), 4.40 (2H, s), 5.74 (2H, s), 6.25 (1H, d), 6.35 (1H, d), 7.15 (1H, d), 7.34 (1H, d), 7.85 (1H, d), 8.88 (1H, s), 10.88 (1H, s). LRMS: m/z 595 $(M+1)^+$.

EXAMPLE 24

1-(1-Methylimidazol-2-yl)methyl-5-[5-(4-methylpiperazin-1-ylsulphonyl)-2-n-propoxyphenyl]-3-n-propyl-1,6-dihydro-7H-pyrazolo[4,3-d]pyrimidin-7-one Obtained as a white foam (36%) from the title compound of Preparation 51 and 1-methylpiperazine using the procedure of Example 1. δ ($CDCl_3$): 0.98 (3H, t), 1.18 (3H, t), 1.84 (2H, m), 2.04 (2H, m), 2.27 (3H, s), 2.50 (4H, m), 2.82 (2H, t), 3.10 (4H, m), 3.76 (3H, s), 4.24 (2H, t), 5.90 (2H, s), 6.84 (1H, s), 6.99 (1H, s), 7.16 (1H, d), 7.84 (1H, d), 8.84 (1H, s), 10.94 (1H, s). LRMS: m/z 569 $(M+1)^+$.

EXAMPLE 25

5-{5-[4-(2-Hydroxyethyl)piperazin-1-ylsulphonyl]-2-n-propoxyphenyl}-1-(1-methylimidazol-2-yl) methyl-3-n-propyl-1,6-dihydro-7H-pyrazolo[4,3-d] pyrimidin-7-one Obtained as a white solid (55%) from the title compound of Preparation 51 and 1-(2-hydroxyethyl)piperazine using the procedure of Example 1. δ ($CDCl_3$): 1.00 (3H, t), 1.18 (3H, t), 1.66 (1H, s), 1.84 (2H, m), 2.06 (2H, m), 2.55 (2H, t), 2.62 (4H, m), 2.92 (2H, t), 3.12 (4H, m), 3.58 (2H, m), 3.77 (3H, s), 4.88 (2H, t), 5.90 (2H, s), 6.85 (1H, s), 7.00 (1H, s), 7.18 (1H, d), 7.85 (1H, d), 8.80 (1H, s). LRMS: m/z 599 $(M+1)^+$.

EXAMPLE 26

5-[5-(4-Ethylpiperazin-1-ylsulphonyl)-2-n-propoxyphenyl]-1-(1-methylimidazol-2-yl)methyl-3-n-propyl-1,6-dihydro-7H-pyrazolo[4,3-d]pyrimidin-7-one Obtained as a white foam (66%) from the title compound of Preparation 51 and 1-ethylpiperazine using the procedure of Example 1. Found: C, 57.48; H, 6.60; N, 18.70. $C_{28}H_{38}N_8O_4S$ requires C, 57.71; H, 6.57; N, 19.23%. δ ($CDCl_3$): 1.00 (6H, m), 1.20 (3H, t), 1.84 (2H, m), 2.05 (2H, m), 2.40 (2H, q), 2.54 (4H, m), 2.92 (2H, t), 3.10 (4H, m), 3.76 (3H, s), 4.26 (2H, t), 5.90 (2H, s), 6.86 (1H, s), 7.00 (1H, s), 7.16 (1H, d), 7.84 (1H, d), 8.84 (1H, s), 10.90 (1H, s). LRMS: m/z 583 $(M+1)^+$.

EXAMPLE 27

1-(3,5-Dimethylisoxazol-4-yl)methyl-5-[5-(4-methylpiperazin-1-ylsulphonyl)-2-n-propoxyphenyl]-3-n-propyl-1,6-dihydro-7H-pyrazolo-[4,3-d]pyrimidin-7-one Obtained as a white solid (83%) from the title compound of Preparation 53 and 1-methylpiperazine using the procedure of Example 1. Found: C, 57.02; H, 6.30; N, 16.28. $C_{28}H_{37}N_7O_5S$; 0.30 $H_2O$ requires C, 56.99; H, 6.59; N, 16.61%. δ ($CDCl_3$): 1.00 (3H, t), 1.17 (3H, t), 1.83 (2H, m), 2.04 (2H, m), 2.25 (3H, s), 2.32 (3H, s), 2.50 (7H, m), 2.90 (2H, t), 3.09 (4H, m), 4.25 (2H t), 5.52 (2H, s), 7.14 (1H, d), 7.83 (1H, d), 8.84 (1H, s), 10.86 (1H, s). LRMS: m/z 584 $(M+1)^+$.

EXAMPLE 28

5-{5-[4-(2-Hydroxyethyl)piperazin-1-ylsulphonyl]-2-n-propoxyphenyl}-1-(3,5-dimethylisoxazol-4-yl) methyl-3-n-propyl-1,6-dihydro-7H-pyrazolo-[4,3-d] pyrimidin-7-one Obtained as a white foam (57%) from the title compound of Preparation 53 and 1-(2-hydroxyethyl)piperazine using the procedure of Example 1. Found: C, 56.33; H, 6.42; N, 15.69. $C_{29}H_{39}N_7O_6S$ requires C, 56.75; H, 6.41; N, 15.98%. δ ($CDCl_3$): 1.01 (3H, t), 1.20 (3H, t), 1.86 (2H, m), 2.06 (2H, m), 2.28 (1H, s), 2.36 (3H, s), 2.52 (3H, s), 2.56 (2H, t), 2.62 (4H, m), 2.92 (2H, t), 3.10 (4H, m), 3.58 (2H, m), 4.28 (2H, t), 5.55 (2H, s), 7.18 (1H, d), 7.86 (1H, d), 8.85 (1H, s), 10.88 (1H, s): LRMS: m/z 614 $(M+1)^+$.

EXAMPLE 29

5-[2-Ethoxy-5-(4-methylpiperazin-1-ylsulphonyl) phenyl]-3methyl-1-(3,5-dimethylisoxazol-4-yl) methyl-1,6-dihydro-7H-pyrazolo[4,3-d]pyrimidin-7-one Obtained as a white solid (88%) from the title compound of Preparation 54 and 1-methylpiperazine using the procedure of Example 1. Found: C, 54.33; H, 5.72; N, 17.74. $C_{25}H_{31}N_7O_5S$; 0.10 $CH_2Cl_2$ requires C, 54.80; H, 5.72; N, 17.82%. δ ($CDCl_3$): 1.65 (3H, t), 2.27 (3H, s), 2.32 (3H, s), 2.50 (10H, m), 3.12 (4H, m), 4.38 (2H, q), 5.52 (2H, s), 7.16,(1H, d), 7.84 (1H, d), 8.88 (1H, s), 10.85 (1H, s). LRMS: m/z 542 $(M+1)^+$.

EXAMPLE 30

5-[5-(4-Methylpiperazin-1-ylsulphonyl)-2-n-propoxyphenyl]-1-(2-methylthiazol-4-yl)methyl-3-n-propyl-1,6-dihydro-7H-pyrazolo[4,3-d]pyrimidin-7-one Obtained as a white foam (61%) from the title compound of Preparation 56 and 1-methylpiperazine using the procedure of Example 1. Found: C, 55.51; H, 6.12; N, 16.28. $C_{27}H_{35}N_7O_4S_2$ requires C, 55.36; H, 6.02; N, 16.74%. δ ($CDCl_3$): 1.00 (3H, t), 1.18 (3H, t), 1.86 (2H, m), 2.04 (2H, m), 2.28 (3H, s), 2.50 (4H, m), 2.68 (3H, s), 2.97 (2H, t), 3.12 (4H, m), 4.26 (2H, t), 5.88 (2H, s), 6.88 (1H, s), 7.17 (1H, d), 7.84 (1H, d), 8.88 (1H, s), 10.90 (1H, s). LRMS: m/z 586 $(M+1)^+$.

EXAMPLE 31

5-[5-(4-Methylpiperazin-1-ylsulphonyl)-2-n-propoxyphenyl]-1(1-methyl-1,2,4-triazol-5-yl)methyl-3-n-propyl-1,6-dihydro-7H-pyrazolo-[4,3-d]pyrimidin-7-one Obtained as a white solid (49%) from the title compound of Preparation 59 and 1-methylpiperazine using the procedure of Example 1. Found: C, 54.96; H, 6.38; N, 21.17. $C_{26}H_{35}N_9O_4S$ requires C, 54.82; H, 6.19; N, 22.13%. δ ($CDCl_3$): 1.01 (3H, t), 1.20 (3H, t), 1.86 (2H, m), 2.06 (2H, m), 2.30 (3H, s), 2.50 (4H, m), 2.94 (2H, t), 3.12 (4H, m), 4.01 (3H, s), 4.27 (2H, t), 5.97 (2H, s), 7.16 (1H, d), 7.84 (1H, s), 7.86 (1H, d), 8.85 (1H, s), 10.96 (1H, s). LRMS: m/z 570 $(M+1)^+$.

EXAMPLE 32

5-{5-[4-(2-Hydroxyethyl)piperazin-1-ylsulphonyl]-2-n-propoxyphenyl}-1-(1-methyl-1,2,4-triazol-5-yl)methyl-3-n-propyl-1,6-dihydro-7H-pyrazolo-[4,3-d]pyrimidin-7-one Obtained as a white foam (62%) from the title compound of Preparation 59 and 1-(2-hydroxyethyl)piperazine using the procedure of Example 1. Found: C, 52.96; H, 6.40; N, 20.14. $C_{27}H_{37}N_9O_5S$; 0.70 $H_2O$ requires C, 52.96; H, 6.32; N, 20.59%. δ ($CDCl_3$): 1.00 (3H, t), 1.20 (3H, t), 1.85 (2H, m), 2.06 (2H, m), 2.30 (1H, s), 2.55 (2H, t), 2.61 (4H, m), 2.94 (2H, t), 3.12 (4H, m), 3.58 (2H, m), 4.00 (3H, s), 4.30 (2H, t), 5.97 (2H, s), 7.18 (1H, d), 7.82 (1H, s), 7.85 (1H, d), 8.85 (1H, s), 10.98 (1H, s). LRMS: m/z 600 $(M+1)^+$.

EXAMPLE 33

5-[5-(4-Ethylpiperazin-1-ylsulphonyl)-2-n-propoxyphenyl]-1-(1-methyl-1,2,4-triazol-5-yl)methyl-3-n-propyl-1,6-dihydro-7H-pyrazolo[4,3-d]pyrimidin-7-one Obtained as a white solid (40%) from the title compound of Preparation 59 and 1-ethylpiperazine using the procedure of Example 1. Found: C, 55.31; H, 6.60; N, 21.09. $C_{27}H_{37}N_9O_4S$ requires C, 55.56; H, 6.39; N, 21.60%. δ ($CDCl_3$): 1.02 (6H, m), 1.18 (3H, t), 1.86 (2H, m), 2.06 (2H, m), 2.41 (2H, q), 2.55 (4H, m), 2.94 (2H, t), 3.10 (4H, m), 4.00 (3H, s), 4.26 (2H, t), 5.97 (2H, s), 7.16 (1H, d), 7.83 (1H, s), 7.85 (1H, d), 8.84 (1H, s), 10.96 (1H, s). LRMS: m/z 584 $(M+1)^+$.

EXAMPLE 34

5-{5-[4-(2-Methoxyethylpiperazin-1-ylsulphonyl]-2-n-propoxyphenyl}-1-(1-methyl-1,2,4-triazol-5-yl)methyl-3-n-propyl-1,6-dihydro-7H-pyrazolo-[4,3-d]pyrimidin-7-one Obtained as a white solid (43%) from the title compound of Preparation 59 and 1-(2-methoxyethyl)piperazine using the procedure of Example 1. δ ($CDCl_3$): 1.00 (3H, t), 1.20 (3H, t), 1.86 (2H, m), 2.06 (2H, m), 2.57 (6H, m), 2.92 (2H, t), 3.12 (4H, m), 3.30 (3H, s), 3.44 (2H, t), 4.00 (3H, s), 4.28 (2H, t), 5.98 (2H, s), 7.16 (1H, d), 7.83 (1H, s), 7.85 (1H, d), 8.86 (1H, s), 10.95 (1H, s). LRMS: m/z 614 $(M+1)^+$.

EXAMPLE 35

1-[1-(2-Methoxyethyl)-1,2,4-triazol-5-yl]methyl-5-[5-(4-methylpiperazin-1-ylsulphonyl)-2-n-propoxyphenyl]-3-n-propyl-1,6-dihydro-7H-pyrazolo[4,3-d]-pyrimidin-7-one Obtained as a white foam (77%) from the title compound of Preparation 64 and 1-methylpiperazine using the procedure of Example 1. δ ($CDCl_3$): 0.97 (3H, t), 1.16 (3H, t), 1.82 (2H, m), 2.00 (2H, m), 2.24 (3H, s), 2.46 (4H, m), 2.86 (2H, t), 3.25 (3H, s), 3.66 (2H, t), 4.22 (2H, t), 4.52 (2H, t), 5.97 (2H, s), 7.12 (1H, d), 7.80 (2H, m), 8.82 (1H, s), 10.86 (1H, s). LRMS: m/z 614 $(M+1)^+$.

EXAMPLE 36

5-[5-(4-Ethylpiperazin-1-ylsulphonyl)-2-n-propoxyphenyl]-1-[1-(2-methoxyethyl)-1,2,4-triazol-5-yl]methyl-3-n-propyl-1,6-dihydro-7H-pyrazolo-[4,3-d]pyrimidin-7-one Obtained as a white foam (66%) from the title compound of Preparation 64 and 1-ethylpiperazine using the procedure of Example 1. Found: C, 55.10; H, 6.62; N, 19.71. $C_{29}H_{41}N_9O_5S$ requires C, 55.49; H, 6.58; N. 20.08%. δ ($CDCl_3$): 0.98 (6H, m), 1.15 (3H, t), 1.80 (2H, m), 2.00 (2H, m), 2.37 (2H, q), 2.50 (4H, m), 2.90 (2H, t), 3.08(4H, m), 3.26 (3H, s), 3.68 (2H, t), 4.22 (2H, t), 4.62 (2H, t), 5.96 (2H, s), 7.12 (1H, d), 7.80 (2H, m), 8.82 (1H, s), 10.86 (1H, s). LRMS: m/z 628 $(M+1)^+$.

EXAMPLE 37

5-[5-(4-Ethylpiperazin-1-ylsulphonyl)-2-n-propoxyphenyl]-1-(4-methyl-1,2,4-triazol-3-yl)methyl-3-n-propyl-1,6-dihydro-7H-pyrazolo[4,3-d]-pyrimidin-7-one Obtained as a white solid (43%) from the title compound of Preparation 66 and 1-ethylpiperazine using the procedure of Example 1. Found: C, 54.46; H, 6.31; N, 21.08. $C_{27}H_{37}N_9O_4S$; 0.60 $H_2O$ requires C, 54.54; H, 6.47; N, 21.20%. 6 ($CDCl_3$): 1.00 (6H, m), 1.20 (3H, t), 1.84 (2H, m), 2.06 (2H, m), 2.40 (2H, q). 2.56 (4H, m), 2.92 (2H, t), 3.12 (4H, m), 3.76 (3H, s), 4.28 (2H, t), 6.04 (2H, s); 7.17 (1H, d), 7.86 (1H, d), 8.10 (1H, s), 8.86 (1H, s), 10.96.(1H, s). LRMS: m/z 584 $(M+1)^+$.

EXAMPLE 38

5-[5-(4-Methylpiperazin-1-ylsulphonyl)-2-n-propoxyphenyl]-1-(4-methyl-1,2,4-triazol-3-yl)methyl-3-n-propyl-1,6-dihydro-7H-pyrazolo[4,3-d]pyrimidin-7-one Obtained as a white solid (51%) from the title compound of Preparation 66 and 1-methylpiperazine using the procedure of Example 1. Found: C, 53.07; H, 6.14; N, 20.48. $C_{26}H_{35}N_9O_4S$; 0.80 $H_2O$; 0.10 $CH_2Cl_2$; 0.05 $CH_3OH$ requires C, 52.86; H, 6.30; N, 21.20%. 5 ($CDCl_3$): 1.00 (3H, t), 1.20 (3H, t), 1.82 (2H, t), 2.06 (2H, m), 2.28 (3H, s), 2.50 (4H, m), 2.92 (2H, t), 3.10 (4H, m), 3.75 (3H, s), 4.27 (2H, t), 6.04 (2H, s), 7.16 (1H, d), 7.84 (1H, s), 7.86 (1H, d), 8.84 (1H, s), 10.96 (1H, s). LRMS; m/z 570 $(M+1)^+$.

EXAMPLE 39

5-{5-[4-(2-Hydroxyethyl)piperazin-1-ylsulphonyl]-2-n-propoxyphenyl}-1-(4-methyl-1,2,4-triazol-3-ylmethyl-3-n-propyl-1,6-dihydro-7H-pyrazolo-[4,3-d]pyrimidin-7-one Obtained as a white solid (37%) from the title compound of Preparation 66 and 1-(2-hydroxyethyl)piperazine using the procedure of Example 1. Found: C, 53.49; H, 6.04; N, 21.50. $C_{27}H_{37}N_9O_5S$; 0.10 $H_2O$ requires C, 53.91; H, 6.23; N, 20.96%. 3 ($CDCl_3$): 1.00 (3H, t), 1.20 (3H, t), 1.84 (2H, m), 2.06 (2H, m), 2.28 (1H, s), 2.56 (2H, t), 2.64 (4H, m), 2.92 (2H, t), 3.14 (4H, m), 3.58 (2H, m), 3.77 (3H, s), 4.28 (2H, t), 6.02 (2H, s), 7.18 (1H, d), 7.86 (1H, d), 8.10 (1H, s), 8.86 (1H, s), 10.98 (1H, s). LRMS: m/z 600 $(M+1)^+$.

EXAMPLE 40

5-[5-(4-Methylpiperazin-1-ylsulphonyl)-2-n-propoxyphenyl]-1-(1,2,4-oxadiazol-3-yl)methyl-3-n-propyl-1,6-dihydro-7H-pyrazolo[4,3-d]pyrimidin-7-one Obtained as a solid (33%) from the title compound of Preparation 67 and 1-methylpiperazine using the procedure of Example 1. δ ($CDCl_3$): 1.00 (3H, t), 1.18 (3H, t), 1.87 (2H, m), 2.04 (2H, m), 2.28 (3H, s), 2.50 (4H, m), 2.94 (2H, t), 3.12 (4H, m), 4.26 (2H, t), 6.02 (2H, s), 7.17 (1H, d), 7.85 (1H, d), 8.67 (1H, s), 8.88 (1H, s), 10.96 (1H, s). LRMS: m/z 557 $(M+1)^+$.

EXAMPLE 41

1-Benzyl-5-[2-ethoxy-5-(4-methylpiperazin-1-ylsulphonyl)phenyl]-3-n-propyl-1,6-dihydro-7H-pyrazolo[4,3-d]pyrimidin-7-one The title compound of Preparation 86 (5.0 g, 8.8 mmol) was added to a stirred solution of potassium t-butoxide (1.2 g, 10 mmol) in t-butanol (75 ml) and the resulting mixture heated under reflux for 20 hours, allowed to cool and evaporated under reduced pressure. The residue was partitioned between ethyl acetate (300 ml) and water (300 ml), then the separated aqueous phase extracted with ethyl acetate (3×150 ml). The combined organic solutions were washed successively with water (150 ml) and brine (150 ml), dried ($MgSO_4$) and evaporated under reduced pressure to give a white solid, trituration of which with ether, followed by drying under vacuum, yielded the title compound (4.29 g) as fine white crystals. Found: C, 60.84; H, 6.20; N, 15.08. $C_{28}H_{34}N_6O_4S$ requires C, 61.08; H, 6.22; N, 15.26%. δ ($CDCl_3$): 1.01 (3H, t), 1.64 (3H, t), 1.88 (2H, m), 2.26 (3H, s), 2.48 (4H, m), 2.96 (2H, t), 3.12 (4H, m), 4.38 (2H, q), 5.78 (2H, s), 7.14 (1H, d), 7.26 (3H, m), 7.40 (2H, m), 7.82 (1H, d), 8.84 (1H, s), 10.80 (1H, s). LRMS: m/z 551 $(M+1)^+$.

EXAMPLE 42

1-Benzyl-5-[5-(4-methylpiperazin-1-ylsulphonyl)-2-n-propoxyphenyl]-3-n-propyl-1-1,6-dihydro-7H-pyrazolo[4,3-d]pyrimidin-7-one A 60% w/w dispersion of sodium hydride in mineral oil (1.60 mg, 4 mmol) was added portionwise to stirred, ice-cooled propan-1-ol (20 ml). When the effervescence had ceased, the title compound of Example 41 (550 mg, 1 mmol) was added and the resulting mixture heated under reflux for 96 hours, then allowed to cool and evaporated under reduced pressure. The residue was partitioned between ethyl acetate (50 ml) and water (50 ml), then the separated aqueous phase extracted with ethyl acetate (100 ml in total). The combined organic solutions were dried ($Na_2SO_4$) and evaporated under reduced pressure, then the residue purified by column chromatography on silica gel, using ethyl acetate:methanol:0.880 aqueous ammonia (95:5:0.5) as eluant, to provide the title compound (230 mg) as a colourless foam. Found: C, 61.65; H, 6.48; N, 14.53. $C_{29}H_{36}N_6O_4S$ requires C, 61.68; H, 6.48; N, 14.88%. δ ($CDCl_3$): 0.98 (3H, t), 1.15 (3H, t), 1.83 (2H, m), 2.01 (2H, m), 2.24 (3H, s), 2.46 (4H, m), 2.92 (2H, t), 3.08 (4H, m), 4.22 (2H, t), 5.73 (2H, s), 7.12 (1H, d), 7.27 (3H, m), 7.36 (2H, m), 7.80 (1H, d), 8.82 (1H, s), 11.84 (1H, s). LRMS: m/z 565 $(M+1)^+$.

EXAMPLE 43

1-(4-Chlorobenzyl)-5-[5-(4-methylpiperazin-1-ylsulphonyl)-2-n-propoxyphenyl]-3-n-propyl-1,6-dihydro-7H-pyrazolo[4,3-d]pyrimidin-7-one Obtained as a white solid (75%) from the title compound of Preparation 87 and 1-methylpiperazine using the procedure of Example 1. Found: C, 57.99; H, 5.94; N, 13.76. $C_{29}H_{35}ClN_6O_4S$ requires C, 58.14; H, 5.89; N, 14.03%. δ ($CDCl_3$): 1.00 (3H, t), 1.19 (3H, t), 1.86 (2H, m), 2.06 (2H, m), 2.28 (3H, s), 2.48.(4H, m), 2.94 (2H, t), 3.08 (4H, m), 4.24 (2H, t), 5.72 (2H, s), 7.15 (1H, d), 7.26 (2H, d), 7.34 (2H, d), 7.82 (1H, d), 8.84 (1H, s), 10.90 (1H, s). LRMS: m/z 599 $(M+1)^+$.

EXAMPLE 44

1-(4-Chlorobenzyl)-5-[2-ethoxy-5-(4-methylpiperazin-1-ylsulphonyl)-phenyl]-3-n-propyl-1,6-dihydro-7H-pyrazolo[4,3-d]pyrimidin-7-one Obtained as a white crystalline solid (27%) from the title compound of Preparation 88 and 1-methylpiperazine using the procedure of Example 1. Found: C, 57.43; H, 5.67; N, 14.30. $C_{28}H_{33}ClN_6O_4S$ requires C, 57.47; H, 5.68; N, 14.36%. δ ($CDCl_3$): 1.00 (3H, t), 1.66 (3H, t), 1.84 (2H, m), 2.36 (3H, s), 2.60 (4H, m), 2.92 (2H, t), 3.18 (4H, m), 4.36 (2H, q), 5.72 (2H, s), 7.14 (1H, d), 7.24 (2H, d), 7.34 (2H, d), 7.82, (1H, d), 8.84 (1H, s), 10.86 (1H, s). LRMS: m/z 585 $(M+1)^+$.

EXAMPLE 45

1-(4-Chlorobenzyl)-5-{2-ethoxy-5-[4-(2-hydroxyethyl)piperazin-1-ylsulphonyl]phenyl}-3-n-propyl-1,6-dihydro-7H-pyrazolo[4,3-d]pyrimidin-7-one Obtained as a white crystalline solid (68%) from the title compound of Preparation 88 and 1-(2hydroxyethyl)piperazine using the procedure of Example 1. Found: C, 56.60; H, 5.71; N, 13.47. $C_{29}H_{35}ClN_6O_5S$ requires C, 56.62; H, 5.73; N, 13.66%. δ ($CDCl_3$): 1.00 (3H, t), 1.64 (3H, t), 1.86 (2H, m), 2.72 (3H, m), 2.82 (4H, m), 2.92 (2H, t), 3.28 (4H, m), 3.70 (2H, m), 4.28 (2H, q), 5.72 (2H, s), 7.18 (1H, d), 7.26 (2H, d), 7.35 (2H, d), 7.82 (1H, d), 8.82 (1H, s), 10.88 (1H, s). LRMS: m/z 615 $(M+1)^+$.

EXAMPLE 46

1-(2-Cyanobenzyl)-5-[2-ethoxy-5-(4-methylpiperazin-1-ylsulphonyl)-phenyl]-3-n-propyl-1,6-dihydro-7H-pyrazolo[4,3-d]pyrimidin-7-one Obtained as a white powder (60%) from the title compound of Preparation 90 and 1-methylpiperazine using the procedure of Example 1. Found: C, 60.42; H, 5.79; N, 16.85. $C_{29}H_{33}N_7O_4S$ requires C, 60.50; H, 5.78; N, 17.03%. δ ($CDCl_3$): 1.00 (3H, t), 1.65,(3H, t), 1.90 (2H, m), 2.28 (3H, s), 2.52 (4H, m), 2.96 (2H, t), 3.15 (4H, m), 4.38 (2H, q), 6.04 (2H, s), 7.08 (1H, d), 7.16 (1H, d), 7.36 (1H, m), 7.68 (1H, d), 7.84 (1H, d), 8.90 (1H, s), 10.88 (1H, s), LRMS: m/z 576 (M+1)⁺.

EXAMPLE 47

1-(2 Carbamoylbenzyl)-5-[2-ethoxy-5-(4-methylpiperazin-1-ylsulphonyl)-phenyl]-3-n-propyl-1,6-dihydro-7H-pyrazolo[4,3-d]pyrimidin-7-one 2M Aqueous sodium hydroxide solution (5 ml) was added to a stirred solution of the title compound of Example 46 (200 mg, 0.35 mmol) in ethanol (5 ml) and the mixture stirred at room temperature for 3 hours, then evaporated under reduced pressure. The residue was dissolved in water (10 ml) and the solution extracted with ethyl acetate (50 ml in total), then the combined organic extracts dried ($Na_2SO_4$) and evaporated under reduced pressure. Purification of the residue by reverse phase column chromatography on polystyrene resin (MCl gel), using an elution gradient of acetonitrile:water (10:90 to 40:60), furnished the title compound (72 mg) as a white powder. Found: C, 56.67; H, 5.79; N, 16.00. $C_{29}H_{35}N_7O_5S$; $H_2O$ requires C, 56.94; H, 6.10; N, 16.03%. δ ($DMSO_{d6}$): 0.94 (3Ht), 1.34 (3H, t), 1.77 (2H, m), 2.14 (3H, s), 2.38 (4H, m), 2.80 (2H, t), 2.92 (4H, m), 4.21 (2H, q), 5.98 (2H, s), 6.59 (1H, s), 7.36 (3H, m), 7.56 (2H, m), 7.82 (1H, d), 7.90 (1H, s), 8.00 (1H, s), 12.26 (1H, s).

EXAMPLE 48

1-(4-Carbamoylbenzyl)-5-[2-ethoxy-5-(4-methylpiperazin-1-ylsulphonyl)-phenyl]-3-n-propyl-1,6-dihydro-7H-pyrazolo[4,3-d]pyrimidin-7-one Obtained as a white solid (93%) from the title compound of Preparation 91 and 1-methylpiperazine using the procedure of Example 1. Found: C, 58.17; H, 5.88; N, 16.28. $C_{29}H_{35}N_7O_5S$ requires C, 58.67; H, 5.94; N, 16.51%. δ ($DMSOd_6$): 0.94 (3H, t), 1.35 (3H, t), 1.76 (2H, m), 2.15 (3H, s), 2.37 (4H, m), 2.80 (2H, t), 2.92 (4H, m), 4.21 (?H, q), 5.79 (2H, s), 7.30 (3H, m), 7.39 (1H, d), 7.84 (5H, m), 12.29 (1H, s). LRMS: m/z 594 (M+1)⁺.

EXAMPLE 49

5-[2-Ethoxy-5-(4-methylpiperazin-1-ylsulphonyl) phenyl]-1-(2-nitrobenzyl)-3-n-propyl-1,6-dihydro-7H-pyrazolo[4,3-d]pyrimidin-7-one Obtained as a white powder (88%) from the title compound of Preparation 93 and 1-methylpiperazine using the procedure of Example 1. Found: C, 56.37; H, 6.14; N, 14.03. $C_{28}H_{33}N_7O_6S$; $CH_3CO_2CH(CH_3)_2$ requires C, 56.80; H, 6.21; N, 14.05%. δ ($CDCl_3$): 1.00 (3H, t), 1.60 (3H, t), 1.88 (2H, m), 2.28 (3H, s), 2.52 (4H, m), 2.97 (2H, t), 3.10 (4H, m), 4.36 (2H, q), 6.24 (2H, s), 6.70 (1H, d), 7.14 (1H, d), 7.44 (2H, m), 7.84 (1H, d), 8.12 (1H, d), 8.86 (1H, s), 10.90 (1H, s). LRMS: m/z 596 (M+1)⁺.

EXAMPLE 50

5-{5-[4-(2-Hydroxyethyl)piperazin-1-ylsulphonyl]-2-n-propoxyphenyl}-1-(2-nitrobenzyl)-3-n-propyl-1,6-dihydro-7H-pyrazolo[4,3-d]pyrimidin-7-one Obtained as a white crystalline solid (76%) from the title compound of Preparation 94 and 1-(2-hydroxyethyl) piperazine using the procedure of Example 1. Found: C, 56.15; H, 5.83; N, 15.06. $C_{30}H_{37}N_7O_7S$ requires C, 56.33; H, 5.83; N, 15.33%. δ ($CDCl_3$): 1.04 (3H, t), 1.17 (3H, t), 1.90 (2H, m), 2.04 (2H, m), 2.30 (1H, t), 2.57 (2H, t), 2.62 (4H, m), 2.98 (2H, t), 3.12 (4H, m), 3.58 (2H, m), 4.26 (2H, t), 6.24 (2H, s), 6.68 (1H, d), 7.18 (1H, d), 7.46 (2H, d), 7.86 (1H, d), 8.12 (1H, d), 8.90 (1H, s), 10.96 (1H, s). LRMS: m/z 640 (M+1)⁺.

EXAMPLE 51

5-[2-Ethoxy-5-(4-methylpiperazin-1-ylsulphonyl) phenyl]-1-(4-nitrobenzyl)-3-n-propyl-1,6-dihydro-7H-pyrazolo[4,3-d]pyrimidin-7-one Obtained as an off-white solid (64%) from the title compound of Preparation 95 and 1-methylpiperazine using the procedure of Example 1. Found: C, 56.10; H, 5.55; N, 16.01. $C_{28}H_{33}N_7O_6S$ requires C, 56.46; H, 5.58; N, 16.46%. δ ($CDCl_3$): 1.00 (3H, t), 1.66 (3H, t), 1.88 (2H, m), 2.40 (3H, s), 2.68 (4H, m), 2.96 (2H, t), 3.24 (4H, m), 4.37 (2H, q), 5.84 (2H, s), 7.16 (1H, d), 7.52 (2H, d), 7.82 (1H, d), 8.16 (1H, s), 8.18 (2H, d), 10.92 (1H, s).

EXAMPLE 52

1-(2-Aminobenzyl)-5-[2-ethoxy-5-(4-methylpiperazin 1-ylsulphonyl)phenyl]-3-n-propyl-1,6-dihydro-7H-pyrazolo[4,3-d]pyrimidin-7-one Raney nickel catalyst (300 mg) was added to a stirred suspension of the title compound of Example 49 (240 mg, 0.4 mmol) in methanol (40 ml) and the mixture hydrogenated at 345 kPa (50 psi) and 50° C. for 20 hours, then allowed to cool and filtered. The filter pad was washed with methanol (50 ml) and the combined methanol solutions evaporated under reduced pressure. The residue was purified by column chromatography on silica gel, using dichloromethane: methanol (95:5) as eluant, followed by crystallisation from ethyl acetate, to afford the title compound (190 mg) as a white powder. Found: C, 58.98; H, 6.20; N, 17.25. $C_{28}H_{35}N_7O_4S$ requires C, 59.45; H, 6.24; N, 17.33%. δ ($CDCl_3$): 1.00 (3H, t), 1.64 (3H, t), 1.83 (2H, m), 2.27 (3H, s), 2.48 (4H, m), 2.92 (2H, t), 3.10 (4H, m), 4.39 (2H, q), 4.78 (2H, s), 5.69 (2H, s), 6.70 (2H, m), 7.12 (2H, m), 7.58 (1H, d), 7.82 (1H, d), 8.80 (1H, s), 10.85 (1H, s).

EXAMPLE 53

1-(2-Aminobenzyl)-5-{5-[4-(2-hydroxyethyl) piperizin-1-ylsulphonyl]-2-n-propoxyphenyl}-3-n-propyl-1,6-dihydro-7H-pyrazolo[4,3-d]pyrimidin-7-one Obtained as a white crystalline solid (54%) from the title compound of Example 50 using the procedure of Example 52, except that ethyl acetate: methanol (95:5) was used as the chromatography eluant and ethanol as the crystallisation solvent. δ ($CDCl_3$): 1.01 (3H, t), 1.20 (3H, t), 1.84 (2H, m), 2.05 (2H, m), 2.30 (1H, s), 2.57 (2H, t), 2.60 (4H, m), 2.92 (2H, t), 3.10 (4H, m), 3.58 (2H, m), 4.26 (2H, t), 4.78 (2H, s), 5.68 (2H, s), 6.70 (2H, m), 7.08 (1H, m), 7.18 (1H, d), 7.57 (1H, d), 7.82 (1H, d), 8.81 (1H, s), 10.98 (1H, s). LRMS: m/z 610 (M+1)⁺.

EXAMPLE 54

1-(4-Aminobenzyl)-5-[2-ethoxy-5-(4-methylpiperazin-1-ylsulphonyl)-phenyl]-3-n-propyl-1,6-dihydro-7H-pyrazolo[4,3-d]pyrimidin-7-one Obtained as a white solid (88%) from the title compound of Example 51 using the procedure of Example 52. Found:

C, 59.38; H, 6.28; N, 17.00. $C_{28}H_{35}N_7O_4S$ requires C, 59.45; H, 6.24; N, 17.33%. δ ($CDCl_3$): 1.00 (3H, t), 1.65 (3H, t), 1.87 (2H, m), 2.28 (3H, s), 2.50 (4H, m), 2.92 (2H, t), 3.10 (4H, m), 3.61 (2H, s), 4.36 (2H, q), 5.62 (2H, s), 6.60 (2H, d), 7.13 (1H, d), 7.26 (2H, d), 7.82 (1H, d), 8.82 (1H, s), 10.83 (1H, s). LRMS: m/z 566 $(M+1)^+$.

EXAMPLE 55

5-[2-Ethoxy-5-(4-methylpiperazin-1-ylsulphonyl) phenyl]-1-(2-methanesulphonamidobenzyl)-3-n-propyl-1,6-dihydro-7H-pyrazolo-[4,3-d]pyrimidin-7-one Methanesulphonyl chloride (31 μl, 0.40 mmol) was added to a stirred, ice-cooled solution of the title compound of Example 52 (150 mg, 0.27 mmol) in pyridine (3 ml) and the mixture stirred at room temperature for 2 hours, then evaporated under reduced pressure. The residue was treated with water (10 ml) and the resulting suspension extracted with dichloromethane (40 ml in total). The combined extracts were dried ($Na_2SO_4$) and evaporated under reduced pressure to give an orange oil which was purified by chromatography on silica gel, using ethyl acetate:methanol:0.880 aqueous ammonia (94:5:1) as eluant, to provide the title compound (62 mg) as a white foam. Found: C, 54.03; H, 5.87; N, 14.70. $C_{29}H_{37}N_7O_6S_2$ requires C, 54.10; H, 5.79; N, 15.23%. δ ($CDCl_3$): 1.02 (3H, t), 1.66 (3H, t), 1.90 (2H, m), 2.28 (3H, s), 2.50 (4H, m), 2.96 (2H, t), 3.10 (7H, m), 4.39 (2H, q), 5.79 (2H, s), 7.18 (2H, m), 7.36 (1H, m), 7.60 (1H, d), 7.72 (1H, d), 7.83 (1H, d), 8.80 (1H, s), 9.68 (1H, s), 10.95 (1H, s). LRMS: m/z 644 $(M+1)^+$.

EXAMPLE 56

5-{5-[4-(2-Hydroxyethyl)piperazin-1-ylsulphonyl]-2-n-propoxyphenyl}-1-(2-methanesulphonamidobenzyl)-3-n-propyl-1,6-dihydro-7H-pyrazolo[4,3-d]-pyrimidin-7-one A 1M solution of tetra-n-butylammonium fluoride in tetrahydrofuran (0.27 ml, 0.27 mmol) was added to a stirred solution of the title compound of Preparation 98 (145 mg, 0.18 mmol) in tetrahydrofuran (3 ml). After a further 20 hours at room temperature, water (5 ml) was added and the resulting mixture extracted with ethyl acetate (20 ml in total). The combined extracts were dried ($Na_2SO_4$) and evaporated under reduced pressure to yield a yellow oil which was purified by column chromatography on silica gel, using ethyl acetate: methanol:0.880 aqueous ammonia (94:5:1) as eluant, followed by crystallisation from ethyl acetate, to furnish the title compound (83 mg) as a white solid. Found: C, 53.89; H, 6.00; N, 14.09. $C_{31}H_{41}N_7O_7S_2$ requires C, 54.13; H, 6.01; N, 14.25%. δ ($CDCl_3$): 1.02 (3H, t), 1.20 (3H, t), 1.90 (2H, m), 2.06 (2H, m), 2.28 (1H, s), 2.56 (2H, m), 2.60 (4H, m), 2.96 (2H, t), 3.10 (7H, m), 3.57 (2H, m), 4.28 (2H, t), 5.79 (2H, s), 7.18 (2H, m), 7.36 (1H, m), 7.60 (1H, d), 7.70 (1H, m), 7.84 (1H, d), 8.82 (1H, s), 9.68 (1H, s),10.99 (1H, s).

EXAMPLE 57

5-[2-Ethoxy-5-(4-methylpiperazin-1-ylsulphonyl) phenyl]-1-(4-methanesulphonamidobenzyl)-3-n-propyl-1,6-dihydro-7H-pyrazolo[4,3-d]-pyrimidin-7-one Obtained as a white solid (64%) from the title compound of Example 54 using the procedure of Example 55. Found: C, 51.10; H, 6.01; N, 13.85. $C_{29}H_{37}N_7O_6S_2$; $2H_2O$ requires C, 51.23; H, 6.08; N, 14.42%. δ ($CDCl_3$): 1.00 (3H, t), 1.62 (3H, t), 1.86 (2H, m), 2.28 (3H, s), 2.50 (4H, m), 2.94 (5H, m), 3.12 (4H, m), 4.36 (2H, q), 5.62 (2H, s), 7.15 (4H, m), 7.38 (2H, d), 7.82 (1H, d), 8.75 (1H, s), 10.94 (1H, s). LRMS: m/z 644 $(M+1)^+$.

EXAMPLE 58

5-[2-Ethoxy-5-(4-methylpiperazin-1-ylsulphonyl) phenyl]-3-n-propyl-1-(4-sulphamoylbenzyl)-1,6-dihydro-7H-pyrazolo[4,3-d]pyrimidin-7-one Obtained as a fine white solid (39%) from the title compound of Preparation 99 and 1-methylpiperazine using the procedure of Example 1. Found: C, 51.72; H, 5.42; N, 14.85. $C_{28}H_{35}N_7O_6S_2$; $H_2O$ requires C, 51.92; H 5.76; N, 15.14%. δ ($CDCl_3$): 1.00 (3H, t), 1.64 (3H, t), 2.28 (3H, m), 2.50 (4H, m), 2.95 (2H, t), 3.10 (4H, m), 4.37 (2H, q), 4.75 (2H, s), 5.80 (2H, s), 7.16 (2H, d), 7.52 (2H, d), 7.84 (3H, m), 8.84 (1H, s), 10.90 (1H, s).

EXAMPLE 59

5-[2-Ethoxy-5-(4-methylpiperazin-1-ysulphonyl) phenyl]-3-methyl-2-(pyridin-2-yl)methyl-2,6-dihydro-7H-pyrazolo[4,3-d]pyrimidin-7-one Obtained as a tan solid (57%) from the title compound of Preparation 42 and 1-methylpiperazine using the procedure of Example 1. δ ($DMSO_{d6}$): 1.30 (3H, t), 2.20 (3H, s), 2.50 (7H, m), 3.06 (4H, m), 4.14 (2H, q), 5.66 (2H, s), 7.06 (1H, d), 7.20 (1H, d), 7.32 (1H, m), 7.64 (1H, d), 7.78 (1H, m), 7.90 (1H, s), 8.50 (1H, d), 11.58 (1H, s). LRMS: m/z 542 $(M+18)^+$.

EXAMPLE 60

5-{2-Ethoxy-5-[4-(2-hydroxyethyl)piperazin-1-ylsulphonyl]phenyl}-3-methyl-2-(pyridin-2-yl) methyl-2,6-dihydro-7H-pyrazolo[4,3-d]pyrimidin-7-one Obtained as a tan foam (47%) from the title compound of Preparation 42 and 1-(2-hydroxyethyl)piperazine using the procedure of Example 1. δ ($CDCl_3$): 1.52 (3H, t), 2.50 (3H, s), 2.55 (2H, t), 2.76 (4H, m), 3.24 (4H, m,), 3.58 (2H, m), 4.24 (2H, q), 5.57 (2H, s), 6.98 (1H, d), 7.10 (1H, d), 7.18 (1H, m), 7.62 (1H, m), 7.88 (1H, d), 8.50 (1H, d), 8.72 (1H, s).

EXAMPLE 61

5-[2-Methoxy-5-(4-methylpiperazin-1-ylsulphonyl) phenyl]-3-n-propyl-2-(pyridin-2-yl)methyl-2,6-dihydro-7H-pyrazolo[4,3-d]pyrimidin-7-one Obtained as a colourless oil (19%) from the title compound of Preparation 43 and 1-methylpiperazine using the procedure of Example 1. Found: C, 56.44; H, 5.76; N, 17.86. $C_{26}H_{31}N_7O_4S$; $H_2O$ requires C, 56.16; H, 5.94; N, 17.64%. δ ($CDCl_3$): 0.94 (3H, t), 1.76 (2H, m), 2.28 (3H, s), 2.50 (4H, m), 2.98 (2H, t), 3.10 (4H, m), 4.12 (3H, s), 5.68 (2H, s), 7.08 (1H, d), 7.18 (2H, m), 7.63 (1H, m), 7.86 (1H, d), 8.58 (1H, d), 8.78 (1H, s), 10.52 (1H, s). LRMS: m/z 538 $(M+1)^+$.

EXAMPLE 62

3-Ethyl-5-[5-(piperazin-1-ylsulphonyl)-2-n-propoxyphenyl]-2-(pyridin-2-yl)methyl-2,6-dihydro-7H-pyrazolo[4,3-d]pyrimidin-7-one Obtained as a white solid (33%) from the title compound of Preparation 18 and piperazine using the procedure of Example 1. Found: C, 57.40; H, 5.81; N. 17.91. $C_{26}H_{31}N_7O_4S$; 0.50 $H_2O$ requires C, 57.13; H, 5.90; N, 17.94%. δ ($CDCl_3$): 1.14 (3H, t), 1.30 (3H, t), 2.01 (2H, m), 2.92 (4H, m), 3.00 (6H, m), 4.22 (2H, t), 5.66 (2H, s), 7.08 (1H, d), 7.14 (1H, d), 7.24 (1H, m), 7.61 (1H, m), 7.82 (1H, d), 8.54 (1H, s), 8.78 (1H, s), 10.60 (1H, s). LRMS: m/z 538 $(M+1)^+$.

EXAMPLE 63

5-[5-(Piperazin-1-ylsulphonyl)-2-n-propoxyphenyl]-3-n-propyl-2-(pyridin-2-yl)methyl-2,6-dihydro-7H-pyrazolo[4,3-d]pyrimidin-7-one trifluoroacetate Trifluoroacetic acid (4 ml) was added to a stirred solution of the title compound of Preparation 44 (388 mg, 0.6 mmol) in dichloromethane (4 ml) and the mixture stirred for 18 hours at room temperature, then evaporated under reduced pressure. The resulting residue was purified by column chromatography on silica gel, using dichloromethane:methanol:0.880 aqueous ammonia (97:3:1) as eluant, to afford the title compound (65%) as a solid. Found: C, 51.93; H, 5.14; N, 14.42. $C_{27}H_{33}N_7O_4S$; $CF_3CO_2H$ requires C, 52.32; H, 5.14; N, 14.73%. δ ($DMSO_{d6}$): 0.86 (3H, t), 1.14 (3H, t), 1.65 (2H, m), 1.74 (2H, m), 2.94 (2H, t), 3.12 (8H, m), 4.14 (2H, t), 5.68 (2H, s), 7.21 (1H, d), 7.34 (1H, m), 7.41 (1H, d), 7.80 (2H, +m), 7.92 (1H, s), 8.12 (1H, s), 8.51 (1H, d), 11.74 (1H, s). LRMS: m/z 573 $(M+18)^+$.

EXAMPLE 64

5-{5-[4-(2-Methoxyethyl)piperazin-1-ylsulphonyl]-2-n-propoxyphenyl}-3-n-propyl-2-(pyridin-2-yl)methyl-2,6-dihydro-7H-pyrazolo[4,3-d]pyrimidin-7-one Obtained as a cream foam (58%) from the title compound of Preparation 20 and 1-(2-methoxyethyl)piperazine using the procedure of Example 1. Found: C, 58.45; H, 6.45; N, 16.08. $C_{30}H_{39}N_7O_5S$; 0.35 $H_2O$ requires C, 58.49;.H, 6.50; N, 15.92%. δ ($CDCl_3$): 0.96 (3H, t), 1.19 (3H, t), 1.76 (2H, m), 2.04 (2H, m), 2.59 (6H, m), 2.98 (2H, m), 3.12 (4H, m), 3.30 (3H, s), 3.42 (2H, t) 4.23 (2H, t), 5.69 (2H, s), 7.06 (1H, d), 7.15 (1H, d), 7.22 (1H, m), 7.62 (1H, m), 7.83 (1H, d), 8.58 (1H, d), 8.77 (1H, s), 1Q.60 (1H, s). LRMS: m/z 610 $(M+1)^+$.

EXAMPLE 65

5-[5-(4-Carbamoylmethylpiperazin-1-ylsulphonyl)-2-n-propoxyphenyl]-3-n-propyl-2-(pyridin-2-y)methyl-2,6-dihydro-7H-pyrazolo[4,3-d]pyrimidin-7-one Obtained as a pale yellow foam (16%) from the title compound of Preparation 20 and 1-carbamoylmethylpiperazine (Indian J. Chem., 1984, 23B, 650) using the procedure of Example 1. δ ($CDCl_3$): 0.95 (3H, t), 1.17 (3H, t), 1.73 (2H, m), 2.05 (2H, m), 2.64 (4H, m), 3.00 (2H, t), 3.02 (2H, s), 3.12 (4H, m), 4.28 (2H, t), 5.69 (2H, s), 6.66 (2H, s), 7.10 (1H, d), 7.18 (1H, d), 7.23 (1H, m), 7.63 (1H, m), 7.86 (1H, d), 8.59 (1H, d), 8.80 (1H, s), 10.62 (1H, s). LRMS: m/z 609 $(M+1)^+$.

EXAMPLE 66

2-(3-Methoxypyridin-2-yl)methyl-5-[5-(4-methylpiperazin1-ylsulphonyl)-2-n-propoxyphenyl]-3-n-propyl-2,6-dihydro-7H-pyrazolo[4,3-d]pyrimidin-7-one Obtained as a white solid (82%) from the title compound of Preparation 48 and 1-methylpiperazine using the procedure of Example 1. Found: C, 57.60; H, 6.23; N, 15.92. $C_{29}H_{37}N_7O_5S$; 0.50 $H_2O$ requires C, 57.60; H, 6.33; N, 16.21%. δ ($CDCl_3$): 0.94 (3H, t), 1.09 (3H, t), 1.78 (2H, m), 1.98 (2H, m), 2.23 (3H, s), 2.44 (4H, m), 2.96 (2H, t), 3.07 (4H, m), 3.86 (3H, s), 4.19 (2H, t), 5.66 (2H, s), 7.10 (1H, d), 7.14 (2H, m); 7.78 (1H, d), 8.06 (1H, d), 8.66 (1H, s), 10.45 (1H, s). LRMS: m/z 595 $(M)^+$.

EXAMPLE 67

5-[5-(4-Ethylpiperazin-1-ylsulphonyl)-2-n-propoxyphenyl]-2-(3-methoxypyridin-2-ylmethyl-3-n-propyl-2,6-dihydro-7H-pyrazolo[4,3-d]pyrimidin-7-one Obtained as a white solid (85%) from the title compound of Preparation 48 and 1-ethylpiperazine using the procedure of Example 1. Found: C, 58.19; H, 6.49; N, 15.62. $C_{30}H_{39}N_7O_5S$; 0.50 $H_2O$ requires C, 58.23; H, 6.52; N, 15.85%. δ ($CDCl_3$): 0.98 (6H, m), 1.10 (3H, t), 1.78 (2H, m), 1.98 (2H, m), 2.37 (2H, q), 2.50 (4H, m), 2.86 (2H, t), 3.07 (4H, m), 3.84 (3H, s), 4.19 (2H, t), 5.67 (2H, s), 7.10 (1H, d), 7.15 (2H, m), 7.68.(1H, d), 8.06 (1H, d), 8.77 (1H, s), 10.44 (1H, s). LRMS: m/z 610 $(M+1)^+$.

EXAMPLE 68

2-(6-Aminopyridin-2-yl)methyl-5-[5-(4-ethylpiperazin-1-ylsulphonyl)-2-n-propoxyphenyl]-3-n-propyl-1,6-dihydro-7H-pyrazolo[4,3-d]pyrimidin-7-one Obtained as a white solid (30%) from the title compound of Preparation 49 using the procedure of Example 1. Found: C, 58.20; H, 6.61; N, 17.77. $C_{29}H_{38}N_8O_4S$; 0.60 $CH_3OH$ requires C, 57.91; H, 6.63; N, 18.25%. δ ($CDCl_3$): 1.00.(6H, m), 1.18 (3H, t), 1.79 (2H, t), 2.04 (2H, t), 2.42 (2H, m); 2.56 (4H, m), 2.99 (2H, t), 3.10 (4H, m), 4.25 (2H, t), 4.42 (2H, s), 5.48 (2H, s), 6.30 (1H, d), 7.15 (1H, d), 7.35 (1H, m), 7.83 (1H, d), 7.79 (1H, s), 8.50 (1H, s), 10.58 (1H, s), LRMS: m/z 595 $(M+1)^+$.

EXAMPLE 69

2-(1-Methylimidazol-2-yl)methyl-5-[5(4-methylpiperazin-1-ylsulphonyl)-2-n-propoxyphenyl]-3-n-propyl-2,6-dihydro-7H-pyrazolo[4,3-d]pyrimidin-7-one Obtained as a white foam (52%) from the title compound of Preparation 52 and 1-methylpiperazine using the procedure of Example 1. δ ($CDCl_3$): 0.96 (3H, t), 1.14 (3H, t), 1.75 (2H, m), 2.02 (2H, m), 2.26 (3H, s), 2.50 (4H, m), 3.10 (6H, m), 3.75 (3H, s), 4.24 (2H, t), 5.67 (2H, s), 6.86 (1H, s), 7.00 (1H, s), 7.14 (1H, d), 7.82 (1H, d), 8.76 (1H, s), 10.60 (1H, s). LRMS: m/z 569 $(M+1)^+$.

EXAMPLE 70

5-[5-(4-Ethylpiperazin-1-ylsulphonyl)-2-n-propoxyphenyl]-2-(1-methylimidazol-2-yl)methyl-3-n-propyl-2,6-dihydro-7H-pyrazolo[4,3-d]-pyrimidin-7-one Obtained as a white solid (70%) from the title compound of Preparation 52 and 1-ethylpiperazine using the procedure of Example 1. Found: C, 56.67; H, 6.65; N, 18.54. $C_{28}H_{38}N_8O_4S$; 0.60 $H_2O$ requires C, 56.66; H, 6.66 N, 18.88%. δ ($CDCl_3$): 1.00 (6H, m), 1.16 (3H, t), 1.76 (2H, m), 2.03 (2H, m), 2.40 (2H, q), 2.52 (4H, m), 3.10 (6H, m), 3.78

(3H, s), 4.23 (2H, t), 5.68 (2H, s), 6.86 (1H, s), 7.00 (1H, s), 7.14 (1H, d), 7.84 (1H, d), 8.77 (1H, s), 10.60 (1H, s). LRMS: m/z 583 (M+1)+.

EXAMPLE 71

5-{5-[4-(2-Hydroxyethyl)piperazin-1-ylsulphonyl]-2-n-propoxyphenyl}-2-(1-methylimidazol-2-yl)methyl-3-n-propyl-2,6-dihydro-7H-pyrazolo[4,3-d]-pyrimidin-7-one Obtained as a white solid (31%) from the title compound of Preparation 52 and 1-(2-hydroxyethyl)piperazine using the procedure of Example 1. δ (CDCl$_3$): 0.98 (3H, t), 1.14 (3H, t), 2.74 (2H, m), 2.04 (2H, m), 2.32 (1H, s), 2.54 (2H, t), 2.60 (4H, m), 3.12 (6H, m), 3.56 (2H, m), 3.76 (3H, s), 4.24 (2H, t), 5.66 (2H, s), 6.84 (1H, s), 7.00 (1H, s), 7.15 (1H, d), 7.82 (1H, d), 8.75 (1H, s), 10.62 (1H, s). LRMS: m/z 599 (M+1)+.

EXAMPLE 72

5-[5-(4-Carbamoylmethylpiperazin-1-ylsulphonyl)-2-n-propoxyphenyl]-1-(1-methylimidazol-2-yl)methyl-3-n-propyl-1,6-dihydro-7H-pyrazolo[4,3-d]-pyrimidin-7-one Obtained as a white solid (17%) from the title compound of Preparation 51 and 1-carbamoylmethylpiperazine (Indian J. Chem., 1984, 23B, 650) using the procedure of Example 1. δ (CDCl$_3$): 1.00 (3H, t), 1.18 (3H, t), 1.86 (2H, m), 2.00 (2H, m), 2.68 (4H, m), 2.92 (2H, t), 3.04 (2H, s), 3.14 (4H, m), 3.78 (3H, s), 4.28 (2H, t), 5.37 (1H, s), 5.90 (2H, s), 6.66 (1H, s), 6.86 (1H, s), 7.00 (1H, s), 7.18 (1H, d), 7.87 (1H, d), 8.84 (1H, s), 10.90 (1H, s). LRMS: m/z 612 (M+1)+.

EXAMPLE 73

2-(3,5-Dimethylisoxazol-4-yl)methyl-5-[5-(4-methylpiperazin-1-ylsulphonyl)-2-n-propoxyphenyl]-3-n-propyl-2,6-dihydro-7H-pyrazolo[4,3-d]-pyrimidin-7-one Obtained as a white foam (34%) from the title compound of Preparation 55 and 1-methylpiperazine using the procedure of Example 1. Found: C, 57.19; H, 6.37; N. 16.19, C$_{28}$H$_{37}$N$_7$O$_5$S; 0.35 H$_2$O requires C, 56.82; H, 6.42; N, 16.66%. δ (CDCl$_3$): 0.98 (3H, t), 1.14 (3H, t), 1.78 (2H, m), 2.02 (2H, m), 2.16 (3H, s), 2.24 (3H, s), 2.35 (3H, s), 2.46 (4H, m), 2.90 (2H, t), 3.57 (4H, m), 4.23 (2H, t), 5.28 (2H, s), 7.14 (1H, d), 7.80 (1H, d), 8.74 (1H, s), 10.64 (1H, s). LRMS: m/z 584 (M+1)+.

EXAMPLE 74

5-{5-[4-(2-Hydroxyethyl)piperazin-1-ylsulphonyl]-2-n-propoxyphenyl}-2-(3,5-dimethylisoxazol-4-yl)methyl-3-n-propyl-2,6-dihydro-7H-pyrazolo[4,3-d]-pyrimidin-7-one Obtained as a white solid (31%) from the title compound of Preparation 55 and 1-(2-hydroxyethyl)piperazine using the procedure of Example 1. Found: C, 55.98; H, 6.44; N, 15.50. C$_{29}$H$_{39}$N$_7$O$_5$S requires C, 56.75; H, 6.41; N, 5.98%. δ (CDCl$_3$): 1.00 (3H, t), 1.15 (3H, t), 1.78 (2H, m), 2.04 (2H, m), 2.18 (3H, s), 2.32 (1H, s), 2.38 (3H, s), 2.54 (2H, t), 2.60 (4H, m), 2.90 (2H, t), 3.08 (4H, m), 3.57 (2H, m), 4.26 (2H, t), 5.30 (2H, s), 7.18 (1H, d), 7.82 (1H, d), 8.77 (1H, s), 10.65 (1H, s). LRMS: m/z 614 (M+1)+.

EXAMPLE 75

5-[2-Ethoxy-5-(4-methylpiperazin-1-ylsulphonyl)phenyl]-3-methyl-2-(2-methylthiazol-4-yl)methyl-2,6-dihydro-7H-pyrazolo[4,3-d]pyrimidin-7-one Obtained as a white solid (80%) from the title compound of Preparation 57 and 1-methylpiperazine using the procedure of Example 1. Found: C, 52.52; H, 5.40; N, 17.54. C$_{24}$H$_{29}$N$_7$O$_4$S$_2$ requires C, 53.02; H, 5.38; N, 18.03%. δ (CDCl$_3$): 1.60 (3H, t), 2.26 (3H, s), 2.48 (4H, m), 2.66 (3H, s), 2.68 (3H, s), 3.10 (4H, m), 4.36 (2H, q), 5.58 (2H, s), 6.92 (1H, s), 7.14 (1H, d), 7.82 (1H, d), 8.80 (1H, s), 10.52 (1H, s). LRMS: m/z 544 (M+1)+.

EXAMPLE 76

5-[5-(4-Methylpiperazin-1-ylsulphonyl)-2-n-propoxyphenyl]-2-(2-methylthiazol-4-yl)methyl-3-n-propyl-2,6-dihydro-7H-pyrazolo[4,3-d]pyrimidin-7-one Obtained as a white foam (43%) from the title compound of Preparation 58 and 1-methylpiperazine using the procedure of Example 1. Found: C, 55.42.; H, 6.13; N, 16.24. C$_{27}$H$_{35}$N$_7$O$_4$S$_2$ requires C, 55.36; H, 6.02; N, 16.74%: δ (CDCl$_3$): 1.00 (3H, t), 1.15 (3H, t), 1.82 (2H, m), 2.04 (2H, m), 2.27 (3H, s), 2.50 (4H, m), 2.70 (3H, s), 3.05 (2H, t), 3.10 (4H, m), 4.24 (2H, t), 5.62 (2H, s), 6.90 (1H, s), 7.16 (1H, d), 7.82 (1H, d), 8.78 (1H, s), 10.58 (1H, s). LRMS: m/z 586 (M+1)+.

EXAMPLE 77

5-[5-(4-Methylpiperazin-1-ylsulphonyl)-2-n-propoxyphenyl]-2-(1-methyl-1,2,4-triazol-5-yl)methyl-3-n-propyl-2,6-dihydro-7H-pyrazolo[4,3-d]pyrimidin-7-one Obtained as a white solid (44%) from the title compound of Preparation 60 and 1-methylpiperazine using the procedure of Example 1. δ (CDCl$_3$): 1.00 (3H, t), 1.16 (3H, t), 1.82 (2H, m), 2.04 (2H, m), 2.27 (3H, s), 2.48 (4H, m), 3.10 (6H, m), 4.02 (3H, s), 4.26 (2H, t), 5.70 (2H, s), 7.15 (1H, d), 7.84 (2H, m), 8.76 (1H, d), 10.63 (1H, s). LRMS: m/z 570 (M+1)+.

EXAMPLE 78

5-[5-(4-Ethylpiperazin-1-ylsulphonyl)-2-n-propoxyphenyl]-2-(1-methyl-1,2,4-triazol-5-yl)methyl-3-n-propyl-2,6-dihydro-7H-pyrazolo[4,3-d]pyrimidin-7-one Obtained as a white solid (83%) from the title compound of Preparation 60 and 1-ethylpiperazine using the procedure of Example 1. Found: C, 54.76; H, 6.36; N, 21.05. C$_{27}$H$_{37}$N$_9$O$_4$S; 0.50 H$_2$O requires C, 54.71; H, 6.46; N, 21.27%. δ (CDCl$_3$): 1.00 (6H, m), 1.15 (3H, t), 1.80 (2H, m), 2.04 (2H, m), 2.40 (2H, q), 2.54.(4H, m), 3.12 (6H, m), 4.02 (3H, s), 4.25 (2H, t), 5.72 (2H, s), 7.13 (1H, d), 7.83 (1H, d), 7.85 (1H, s), 8.74 (1H, s), 10.62 (1H, s). LRMS: m/z 584 (M+1)+.

EXAMPLE 79

5-{5-[4-(2-Methoxyethyl)piperazine-1-ylsulphonyl]-2-n-propoxyphenyl}-2-(1-methyl-1,2,4-triazol-5-yl)methyl-3-n-propyl-2,6-dihydro-7H-pyrazolo[4,3-d]-pyrimidin-7-one Obtained as a white solid (89%) from the title compound of Preparation 60 and 1-(2-methoxyethyl)piperazine using the procedure of Example 1. Found: C, 54.36; H, 6.38; N, 20.15. C$_{28}$H$_{39}$N$_9$O$_5$S requires C, 54.80; H, 6.41; N, 20.54%. δ (CDCl$_3$): 1.00 (3H, t), 1.17 (3H, t), 1.80 (2H, m), 2.04 (2H, m), 2.58 (6H, m), 3.10 (4H, m), 3.30 (3H, s), 3.43 (2H, t), 4.00 (3H, s), 4.26 (2H, t), 5.72 (2H, s), 7.14 (1H, d), 7.83 (2H, m), 8.77 (1H, s), 10.63 (1H, s). LRMS: m/z 614 (M+1)+.

EXAMPLE 80

5-[5-(4-Ethylpiperazin-1-ylsulphonyl)-2-n-propoxyphenyl]-2-[1-(2-methoxyethyl)-1,2,4-triazol-5-yl]methyl-3-n-propyl-2,6-dihydro-7H-pyrazolo-[4,3-d]pyrimidin-7-one Obtained as a white foam (68%) from the title compound of Preparation 65 and 1-ethylpiperazine using the procedure of Example 1. Found: C, 54.96; H, 6.59; N, 19.67. $C_{29}H_{41}N_9O_5S$ requires C, 55.49; H, 6.58; N, 20.08. δ (CDCl$_3$): 1.00 (6H, m), 1.14 (3H, t), 1.80 (2H, m), 1.98 (2H, m), 2.37 (2H, q), 2.50 (4H, m), 3.05 (6H, m), 3.26 (3H, s), 3.68 (2H, t), 4.20 (2H, t), 4.58 (2H, t), 5.73 (2H, s), 7.10 (1H, d), 7.80 (2H, m), 8.73 (1H, s), 10.54 (1H, s). LRMS: m/z 628 (M+1)$^+$.

EXAMPLE 81

5-[5-(4-Methylpiperazin-1-ylsulphonyl)-2-n-propoxyphenyl]-2-(3-methyl-1,2,4-triazol-5-yl)methyl-3-n-propyl-2,6-dihydro-7H-pyrazolo[4,3-d]pyrimidin-7-one Obtained as a white solid (49%) from the title compound of Preparation 72 and 1-methylpiperazine using the procedure of Example 1. δ (CDCl$_3$): 1.02 (3H, t), 1.15 (3H, t), 1.86 (2H, m), 2.02.(2H, m), 2.27 (3H, s), 2.42 (3H, s), 3.08 (4H, m), 4.24 (2H, t), 5.61 (2H, s), 7.12 (1H, d), 7.79 (1H, d), 8.76 (1H, s), 10.65 (1H, s). LRMS: m/z 570 (M+1)$^+$.

EXAMPLE 82

5-[2-Ethoxy-5-(4-methylpiperazin-1-ylsulphonyl)phenyl]-2-(5-methyl-1,2,4-oxadiazol-3-yl)methyl-3-n-propyl-2,6-dihydro-7H-pyrazolo[4,3-d]pyrimidin-7-one Obtained as a white solid (470%) from the title compound of Preparation 79 and 1-methylpiperazine using the procedure of Example 1. Found: C, 52.44; H, 5.63; N, 19.48. $C_{25}H_{32}N_8O_5S$; H$_2$O requires C, 52.25; H, 5.96; N, 19.50%. δ (DMSO$_{d6}$): 0.93 (3H, t), 1.34 (3H, t), 1.74 (2H, m), 2.12 (3H, s), 2.35 (4H, m), 2.56 (3H, s), 2.90 (4H, m), 2.98 (2H, t), 4.20 (2H, q), 5.76 (2H, s), 7.36 (1H, d), 7.81 (1H, d), 7.85 (1H, s), 11.80 (1H, s). LRMS: m/z 557 (M+1)$^+$.

EXAMPLE 83

5-{2-Ethoxy-5-[4-(2-hydroxyethyl)piperazin-1-ylsulphonyl]phenyl}-2-(5-methyl-1,2,4-oxadiazol-3-yl)methyl-3-n-propyl-2,6-dihydro-7H-pyrazolo[4,3-d]pyrimidin-7-one Obtained as a solid (56%) from the title compound of Preparation 79 and 1-(2-hydroxyethyl)piperazine using the procedure of Example 1. Found: C, 53.15; H, 6.14; N, 17.98. $C_{26}H_{34}N_8O_6S$ requires C, 53.23; H, 5.84; N, 19.10%. δ (CDCl$_3$): 1.03 (3H, t), 1.63 (3H, t), 1.88 (4H, m), 2.57 (4H, m), 2.65 (4H, m), 3.05 (2H, t), 3.12 (4H, m), 3.60 (2H, t), 4.38 (2H, q), 5.62 (2H, s), 7.16 (1H, d), 7.83 (1H, d), 8.77 (1H, d), 10.61 (1H, s). LRMS: m/z 587 (M+1)$^+$.

EXAMPLE 84

2-(5-Methyl-1,2,4-oxadiazol-3-yl)methyl-5-[5-(4-methylpiperazin-1-ylsulphonyl)-2-n-propoxyphenyl]-3-n-propyl-2,6-dihydro-7H-pyrazolo[4,3-d]-pyrimidin-7-one Obtained as a white solid (91%) from the title compound of Preparation 76 and 1-methylpiperazine using the procedure of Example 1. Found: C, 54.43; H, 6.06; N, 19.46. $C_{26}H_{34}N_8O_5S$ requires C, 54.72; H, 6.01; N, 19.64%. δ (DMSO$_{d6}$): 0.94 (6H, m), 1.74 (4H, m), 2.15 (3H, s), 2.36 (4H, m), 2.58 (3H, s), 2.90 (4H, m), 2.98 (2H, t), 4.12 (2H, t), 5.78.(2H, s), 7.38 (1H, d), 7.80 (1H, d); 7.84 (1H, s), 11.79 (1H, s). LRMS m/z 571 (M+1)$^+$.

EXAMPLE 85

5-[5-(4-Ethylpiperazin-1-ylsulphonyl)-2-n-propoxyphenyl1-2-(5-methyl-1,2,4-oxadiazol-3-yl)methyl-3-n-propyl-2,6-dihydro-7H-pyrazolo[4,3-d]pyrimidin-7-one Obtained as a white solid (70%) from the title compound of Preparation 76 and 1-ethylpiperazine using the procedure of Example 1. Found: C, 54.85; H, 6.16; N, 18.69. $C_{27}H_{36}N_8O_5S$; 0.25 H$_2$O requires C, 55.04; H, 6.24; N, 19.02%. δ (CDCl$_3$): 0.98 (6H, m), 1.09 (3H, t), 1.83 (2H, m), 1.98 (2H, m), 2.37 (2H, q), 2:49 (4H, m), 2.54 (3H, s), 3.00 (2H, t), 3.04 (4H, m), 4.20 (2H, t), 5.58 (2H, s), 7.10 (1H, d), 7.78 (1H, d), 8.72 (1H, s), 10.53 (1H, s). LRMS: m/z 584 (M)$^+$.

EXAMPLE 86

5-{5-[4-(2-Hydroxyethyl)piperazin-1-ylsulphonyl]-2-n-propoxyphenyl}-2-(5-methyl-1,2,4-oxadiazol-3-yl)methyl-3-n-propyl-2,6-dihydro-7H-pyrazolo-[4,3-d]pyrimidin-7-one Obtained as a white solid (86%) from the title compound of Preparation 76 and 1-(2-hydroxyethyl)piperazine using the procedure of Example 1. Found: C, 53.22; H, 6.00; N, 18.06. $C_{27}H_{36}N_8O_6S$; 0.25 H$_2$O; 0.10 CH$_3$CO$_2$CH$_2$CH$_3$ requires C, 53.60; H, 6.12; N, 18.25%. δ (CDCl$_3$): 1.04 (3H, t), 1.17 (3H, t), 1.88 (2H, m), 2.04 (2H, m), 2.30 (1H, s), 2.58 (5H, m), 2.61 (4H, m), 3.05 (2H, t), 3.12 (4H, m), 3.60 (2H, m),4.26 (2H, t), 5.63 (2H, s), 7.18 (1H, d), 7.84 (1H, d), 8.79 (1H, s), 10.60 (1H, s). LRMS: m/z 600 (M)$^+$.

EXAMPLE 87

2-Benzyl-5-[2-ethoxy-5-(4-methylpiperazin-1-ylsulphonyl)phenyl]-3-n-propyl-2,6-dihydro-7H-pyrazolo[4,3-d]pyrimidin-7-one Triethylamine (64 µl, 0.46 mmol), sodium formate (32 mg, 0.46 mmol) and tetrakis(triphenylphosphine)palladium (0) (17 mg, 0.015 mmol) were added to a stirred solution of the title compound of Example 88 (200 mg, 0.32 mmol) in a mixture of acetonitrile (1.5 ml) and dimethyl sulphoxide (1.5 ml), under nitrogen, and the resulting mixture heated under reflux for 20 hours, then evaporated under reduced pressure. The residue was suspended in brine (10 ml) and the suspension extracted with ethyl acetate (30 ml in total). The combined extracts were dried (Na$_2$SO$_4$) and evaporated under reduced pressure, then the residue purified by column chromatography on silica gel, using ethyl acetate:methanol:0.880 aqueous ammonia (94:5:1) as eluant, to furnish the title compound (84 mg) as a colourless gum. δ (CDCl$_3$): 0.95 (3H, t), 1.62 (3H, t), 1.74 (2H, m), 2.30 (3H, s), 2.57 (4H, m), 2.90 (2H, t), 3.16 (4H, m), 4.39 (2H, q), 5.58 (2H, s), 7.10–7.36 (6H, m), 7.82 (1H, d), 8.78 (1H, s), 10.60 (1H, s). LRMS: m/z 551 (M+1)$^+$.

EXAMPLE 88

2-(4-Bromobenzyl)-5-[2-ethoxy-5-(4-methylpiperazin-1-ylsulphonyl)-phenyl]-3-n-propyl-2,6-dihydro-7H-pyrazolo[4,3-d]pyrimidin-7-one Obtained as a white foam (57%) from the title compound of Preparation 89 and 1-methylpiperazine using the procedure of Example 1. Found: C, 52.80; H, 5.38; N, 12.83. $C_{28}H_{33}BrN_6O_4S$; 0.50 $H_2O$ requires C, 52.64; H, 5.37; N, 13.16%. δ ($CDCl_3$): 0.93 (3H, t), 1.60 (3H, t), 1.72 (2H, m), 2.40 (3H, s), 2.64 (4H, m), 2.90 (2H, t), 3.22 (4H, m), 4.38 (2H, q), 5.48 (2H, s), 7.04 (2H, d), 7.14 (1H, d), 7.44 (2H, d), 7.80 (1H, d), 8.76 (1H, s), 10.62 (1H, s).

EXAMPLE 89

2-(4-Bromobenzyl)-5-{2-ethoxy-5-[4-(2-hydroxyethyl)piperazin-1-ylsulphonyl]phenyl}-3-n-propyl-2,6-dihydro-7H-pyrazolo[4,3-d]pyrimidin-7-one Obtained as a white foam (66%) from the title compound of Preparation 89 and 1-(2-hydroxyethyl)piperazine using the procedure of Example 1. Found: C, 52.13; H, 5.37; N, 12.42. $C_{29}H_{35}BrN_6O_5S$; 0.50 $H_2O$ requires C, 52.05; H. 5.43; N, 12.57%. δ ($CDCl_3$): 0.97 (3H, t), 1.63 (3H, t), 1.76 (2H, m), 2.68 (3H, m), 2.78 (4H, m), 2.86 (2H, t), 3.20 (4H, m), 3.66 (2H, m), 4.39 (2H, q), 5.50 (2H, s), 7.10 (2H, d), 7.18 (1H, d), 7.46 (2H, d), 7.81 (1H, d), 8.77 (1H, s), 10.64 (1H, s). LRMS: m/z 659 $(M)^+$.

EXAMPLE 90

2-(4-Carbamoylbenzyl)-5-[2-ethoxy-5-(4-methylpiperazin-1-ylsulphonyl)phenyl]-3-n-propyl-2,6-dihydro-7H-pyrazolo[4,3-d]pyrimidine-7-one Obtained as a white foam (28%) from the title compound of Preparation 92 and 1-methylpiperazine using the procedure of Example 1. Found:.C, 55.76; H, 6.04; N. 15.56. $C_{29}H_{35}N_7O_5S$; 0.50 $CH_2Cl_2$ requires C, 55.78; H, 5.71; N, 15.44%. δ ($CDCl_3$): 0.93 (3H, t), 1.63 (3H, t), 1.76 (2H, m), 2.24 (3H, s), 2.46 (4H, m), 2.90 (2H, t), 3.08 (4H, m), 4.38 (2H, q), 5.59 (2H, s), 7.17 (1H, d), 7.25 (3H, m), 7.80 (3H, m), 8.78 (1,H, s), 10.69 (1H, s). LRMS: m/z 594 $(M+1)^+$.

EXAMPLE 91

5-[2-Ethoxy-5-(4-methylpiperazin-1-ylsulphonyl) phenyl]-2-(4-nitrobenzyl)-3-n-propyl-2,6-dihydro-7H-pyrazolo[4,3-d]pyrimidin-7-one Obtained as a yellow foam (82%) from the title compound of Preparation 96 and 1-methylpiperazine using the procedure of Example 1. Found: C, 55.96; H, 5.54; N, 16.27. $C_{28}H_{33}N_7O_6S$ requires C, 56.46; H, 5.58; N, 16.46%. δ ($CDCl_3$): 0.94 (3H, t), 1.65 (3H, t), 1.74 (2H, m), 2.27 (3H, s), 2.47 (4H, m), 2.90 (2H, t), 3.10 (4H, m), 4.38 (2H, q), 5.64 (2H, s), 7.14 (1H, d), 7.35 (2H, d), 7.82 (1H, d), 8.20 (2H, d), 8.78 (1H, s), 10.68 (1H, s). LRMS: m/z 596 $(M+1)^+$.

EXAMPLE 92

5-{2-Ethoxy-5-[4-(2-hydroxyethyl)piperazin-1-ylsulphonyl]phenyl}-2-(4-nitrobenzyl)-3-n-propyl-2,6-dihydro-7H-pyrazolo[4,3-d]pyrimidin-7-one Obtained as a yellow oil (90%) from the title compound of Preparation 96 and 1-(2-hydroxyethyl)piperazine using the procedure of Example 1. Found: C, 54.83; H, 5.61; N, 15.46. $C_{29}H_{35}N_7O7_8$; 0.50 $H_2O$ requires C, 54.88; H, 5.72; N, 15.45%. 8 ($CDCl_3$): 0.96 (3H, t), 1.62 (3H, t), 1.74 (2H, m), 2.30 (1H, s), 2.55 (2H, t), 2.60 (4H, m), 2.90 (2H, t), 3.10 (4H, m), 3.58 (2H, m), 4.39 (2H, q), 5.64 (2H, s), 7.17 (1H, d), 7.33 (2H, d), 7.82 (1H, d), 8.20 (2H, d), 8.78 (1H, s), 10.70 (1H, s).

EXAMPLE 93

2-(4-Aminobenzyl)-5-[2-ethoxy-5-(4-methylpiperazin-1-ylsulphonyl)-phenyl]-3-n-propyl-2,6-dihydro-7H-pyrazolo[4,3-d]pyrimidin-7-one Obtained as a colourless foam (77%) from the title compound of Example 91 using the procedure of Example 52. Found: C, 58.51; H, 6.18; N, 16.76. $C_{28}H_{35}N_7O_4S$; 0.50 $H_2O$ requires C, 58.52; H, 6.31; N, 17.06%. δ ($CDCl_3$): 0.83 (3H, t), 1.64 (3H, t), 1:72 (2H, m), 2.27 (3H, s), 2.48 (4H, m), 2.90 (2H, t), 3.10 (4H, m), 3.69 (2H, s), 4.36 (2H, q),5.43 (2H, s), 6.62 (2H, d), 7.06 (2H, d), 7.14 (1H, d), 7.80 (1H, d), 8.76 (1H, s), 10.58 (1H, s) ppm.

EXAMPLE 94

1-(N-Ethylcarbamoylmethyl)-5-[5-(4-methylpiperazin-1-ylsulphonyl)-2-n-propoxyphenyl]-3-n-propyl-1,6-dihydro-7H-pyrazolo[4,3-d]pyrimidin-7-one Obtained as a brown solid (40%) from the title compound of Preparation 102 and 1-methylpiperazine using the procedure of Example 1. δ ($CDCl_3$): 1.01 (3H, t), 1.08 (3H, t), 1.18 (3H, t), 1.89 (2H, m), 2.04 (2H, m), 2.28 (3H, s), 2.49 (4H, m), 2.97 (2H, t), 3.10 (4H, m), 3.29 (2H, m), 4.25 (2H, t), 5.23 (2H, s), 6.14 (1H, s), 7.18 (1H, d), 7.86 (1H, d), 8.87 (1H, s), 10.95 (1H, s). LRMS: m/z 560 $(M+1)^+$.

EXAMPLE 95

1-[N-(2-Methoxyethyl)carbamoylmethyl]-5-[5(4-methylpiperazin-1-ylsulphonyl)-2-n-propoxyphenyl]-3-n-propyl-1,6-dihydro-7H-pyrazolo[4,3-d]-pyrimidin-7-one Obtained as a white foam (63%) from the title compound of Preparation 103 and 1-methylpiperazine using the procedure of Example 1. Found: C, 54.60; H, 6.87; N, 16.02. $C_{27}H_{39}N_7O_6S$ requires C, 54.98; H, 6.67; N, 16.03%. 5 ($CDCl_3$): 1.05 (3H, t), 1.20 (3H, t), 1.89 (2H, m), 2.04 (2H, m), 2.29 (3H, s), 2.50 (4H, m), 2.98 (2H, t), 3.10 (4H, m), 3:33 (3H, s), 3.43 (4H, m), 4.29 (2H, t), 5.28 (2H, s), 6.42 (1H, s), 7.18 (1H, d), 7.86 (1H, d), 8.88 (1H, s), 10.93 (1H, s). LRMS: m/z 590 $(M+1)^+$.

EXAMPLE 96

5-[5-(4-Methylpiperazin-1-ylsulphohyl)-2-n-propoxyphenyl]-1-(morpholin-4-ylcarbonylmethyl)-3-n-propyl-1,6-dihydro-7H-pyrazolo[4,3-d] pyrimidin-7-one Obtained as a beige solid (59%) from the title compound of Preparation 104 and 1-methylpiperazine using the procedure of Example 1. Found: C, 54.25; H, 6.50; N, 14.72. $C_{28}H_{39}N_7O_6S$; $H_2O$ requires C, 54.27; H, 6.67; N, 15.82%. δ ($CDCl_3$): 1.02 (3H, t), 1.19 (3H, t), 1.88 (2H, m), 2.02 (2H, m), 2.27 (3H, s), 2.50 (4H, m), 2.98 (2H, t), 3.12 (4H, m), 3.56 (2H, m), 3.62 (2H, m), 3.73 (4H, m), 4.24 (2H, t), 5.45 (2H, s), 7.15 (1H, d), 7.83 (1H, d), 8.86 (1H, s), 10.87 (1H, s). LRMS: m/z 602 $(M+1)^+$.

EXAMPLE 97

5-15-(4-Methylpiperazin-1-ylsulphonyl)-2-n-propoxyphenyl]-1-[1S-(morpholin-4-ylcarbonyl) ethyl]-3-n-propyl-1,6-dihydro-7H-pyrazolo-[4,3-d] pyrimidin-7-one Obtained as a white solid (61%) from the title compound of Preparation 109 and 1-methylpiperazine using the procedure of Example 1. Found: C, 55.16; H, 6.58; N, 15.39. $C_{29}H_{41}N_7O_6S$; 0.25 $CH_2Cl_2$ requires C, 55.16; H, 6.57; N, 15.39%. δ ($CDCl_3$): 1.02 (3H, t), 1.20 (3H, t), 1.79 (3H, d), 1.87 (2H, m), 2.06 (2H, m), 2.28 (3H, s), 2.50 (4H, m), 2.98 (2H, t), 3.10 (4H, m), 3.48 (2H, m), 3.64 (6H, m), 4.27 (2H, t), 6.16 (1H, q), 7.18 (1H, d), 7.84 (1H, d), 8.86 (1H, s), 10.91 (1H, s). LRMS: m/z 616 (M+1)⁺.

EXAMPLE 98

5-[5-(4-Methylpiperazin-1-ylsulphonyl)-2-n-propoxyphenyl]-1-[R-(morpholin-4-ylcarbonyl) ethyl]-3-n-propyl-1,6-dihydro-7H-pyrazolo[4,3-d]-pyrimidin-7-one Obtained as a cream foam (54%) from the title compound of Preparation 112 and 1-methylpiperazine using the procedure of Example 1. Found: C, 56.26; H, 6.91; N, 15.20. $C_{29}H_{41}N_7O_6S$ requires C, 56.57; N, 6.71; N, 15.92%. δ (CDCl$_3$): 1.00 (3H, t), 1.20 (3H, t), 1.79,(3H, d), 1.87 (2H, m), 2.06 (2H, m), 2.27 (3H, s), 2.56 (4H, m), 2.97 (2H, t), 3.10 (4H, m), 3.48 (2H, m), 3.64 (6H, m), 4.27 (2H, t), 6.18 (1H, q), 7.18 (1H, d), 7.85 (1H, d), 8.89 (1H, s), 10.90 (1H, s). LRMS: m/z 616 (M+1)⁺.

EXAMPLE 99

5-[5-(4-Methylpiperazin-1-ylsulphonyl)-2-n-propoxyphenyl]-1-(2-morpholin-4-ylethyl)-3-n-propyl-1,6-dihydro-7H-pyrazolo[4,3-d]pyrimidin-7-one Obtained as a white solid (41%) from the title compound of Preparation 114 and 1-methylpiperazine using the procedure of Example 1. δ (CDCl$_3$): 1.00 (3H, t), 1.20 (3H, t), 1.86 (2H, m), 2.06 (2H, m), 2.28 (3H, s), 2.50 (8H, m), 2.92 (4H, m), 3.10 (4H, m), 3.60 (4H, m), 4.24 (2H, t), 4.68 (2H, t), 7.17 (1H, d), 7.82 (1H, d), 8.88 (1H, s), 10.84 (1H, s). LRMS: m/z 589 (M+1)⁺.

EXAMPLE 100

5-[5-(4-Ethylpiperazin-1-ylsulphonyl)-2-n-propoxyphenyl]-1-(2-morpholin-4-ylethyl)-3-n-propyl-1,6-dihydro-7H-pyrazolo[4,3-d]pyrimidin-7-one Obtained as a solid (36%) from the title compound of Preparation 114 of 1-ethylpiperazine using the procedure of Example 1. Found: C, 57.44; H, 7.22; N, 15.86. $C_{29}H_{43}N_7O_5S$ requires C, 57.88; H, 7.20; N, 16.29%. δ (CDCl$_3$): 1.00 (6H, m), 1.18 (3H, t), 1.86 (2H, m), 2.04 (2H, m), 2.40 (2H, q), 2.52 (8H, m), 2.86 (2H, t), 2.90 (2H, t), 3.10 (4H, m), 3.60 (4H, m), 4.24 (2H, t), 4.70 (2H, t), 7.16 (1H, d), 7.84 (1H, d), 8.86 (1H, s), 10.84 (1H, s). LRMS: m/z 603 (M+1)⁺.

EXAMPLE 101

5-{5-[4-(2-Methoxyethyl)piperazin-1-ylsulphonyl]-2-n-propoxyphenyl}-1-(2-morpholin-4-ylethyl)-3-n-propyl-1,6-dihydro-7H-pyrazolo[4,3-d]pyrimidin-7-one Obtained as a white solid (35%) from the title compound of Preparation 114 and 1-(2-methoxyethyl)piperazine using the procedure of Example 1. Found: C, 56.41; H, 7.11; N, 15.07. $C_{30}H_{45}N_7O_6S$: 0.30H$_2$O requires C, 56.55; H, 7.21; N, 15.39%. δ (CDCl$_3$): 1.00 (3H, t), 1.20 (3H, t), 1.86 (2H,m), 2.06 (2H, m), 2.50 (4H, m), 2.58 (4H, m), 2.86 (2H, t), 2.94 (2H, t), 3.10 (4H, m), 3.28 (3H, s), 3.42 (2H, t), 3.60 (4H, m), 4.24 (2H, t), 4.70 (2H, t), 7.14 (1H, d), 7.82 (1H, d), 8.84 (1H, s), 10.84 (1H, s). LRMS: m/z 633 (M+1)⁺.

EXAMPLE 102

2-(N-Ethylcarbamoylmethyl)-5-[5-(4-methylpiperazin-1-ylsulphonyl)-2-n-propoxyphenyl]-3-n-propyl-2,6-dihydro-7H-pyrazolo[4,3-d]pyrimidin-7-one Obtained as a cream foam (61%) from the title compound of Preparation 105 and 1-methylpiperazine using the procedure of Example 1. Found: C, 54.59; H, 6.62; N, 16.32. $C_{26}H_{37}N_7O_5S$; 0.70 H$_2$O requires C, 54.57; H, 6.76; N, 16.13%. δ (CDCl$_3$): 1.02 (3H, t), 1.10 (3H, t), 1.20 (3H, t), 1.82 (2H, m), 2.07 (2H, m), 2.28 (3H, s), 2.50 (4H, m), 3.00 (2H, t), 3.11 (4H, m), 3.29 (2H, m), 4.26 (2H, t), 4.99 (2H, s), 6.23 (1H, s), 7.17 (1H, d), 7.86 (1H, d), 8.82 (1H, s), 10.72 (1H, s). LRMS: m/z 560 (M+1)⁺.

EXAMPLE 103

2-[N-(2-Methoxyethyl)carbamoylmethyl]-5-[5-(4-methylpiperazin-1-ylsulphohyl)-2-n-propoxyphenyl]-3-n-propyl-2,6-dihydro-7H-pyrazolo-[4,3-d]pyrimidin-7-one Obtained as a cream foam (54%) from the title compound of Preparation 106 and 1-methylpiperazine using the procedure of Example 1. Found: C, 54.67; H, 6.69; N, 15.89. $C_{27}H_{39}N_7O_6S$ requires C, 54.98; H, 6.67; N, 16.03%. δ (CDCl$_3$): 1.01 (3H, t); 1.17 (3H, t), 1.85 (2H, m), 2.04 (2H, m), 2.28 (3H, s), 2.40 (4H, m), 3.00 (2H, t), 3.10 (4H, m), 3.30 (3H, s), 3.41 (4H, m), 4.26 (2H, t), 5.01 (2H, s), 6.38 (1H, s), 7.17 (1H, d), 7.83 (1H, d), 8.82 (1H, s), 10.68 (1H, s). LRMS: m/z 590 (M+1)⁺.

EXAMPLE 104

5-[5-(4-Methylpiperazin-1-ylsulphonyl)-2-n-propoxyphenyl]-2-(morpholin-4-ylcarbonylmethyl)-3-n-propyl-2,6-dihydro-7H-pyrazolo[4,3-d] pyrimidin-7-one Obtained as a white foam (52%) from the title compound of Preparation 107 and 1-methylpiperazine using the procedure of Example 1. Found: C, 54.74; H, 6.46; N, 15.72. $C_{28}H_{39}N_7O_6S$; 0.20 $CH_2Cl_2$ requires C, 54.75; H, 6.42; N, 15.85%. δ (CDCl$_3$): 1.02 (3H, t), 1.15 (3H, t), 1.90 (2H, m), 2.02 (2H, m), 2.27 (3H, s), 2.49 (4H, m), 3.00 (2H, t), 3.10 (4H, m), 3.65 (4H, m), 3.72 (4H, m), 4.24 (2H, t), 5.21 (2H, s), 7.15 (1H, d), 7.85 (1H, d), 8.81 (1H, s), 10.58 (1H, s). LRMS: m/z 602 (M+1)⁺.

EXAMPLE 105

5-[5-(4-Methylpiperazin-1-ylsulphonyl)-2-n-propoxyphenyl]-2-[1S-(morpholin-4-ylcarbonylethyl]-3-n-propyl-2,6-dihydro-7H-pyrazolo[4,3-d]-pyrimidin-7-one Obtained as a white foam (52%) from the title compound of Preparation 110 and 1-methylpiperazine using the procedure of Example 1. Found: C, 54.57; H, 6.52; N, 15.15. $C_{29}H_{41}N_7O_6S$; 0.36 $CH_2Cl_2$ requires C, 54.56; H, 6.51; N, 15.17%. δ (CDCl$_3$): 1.01 (3H, t), 1.15 (3H, t), 1.82 (3H, d), 1.88 (2H, m), 2.03 (2H, m), 2.26 (3H, s), 2.50 (4H, m), 2.98 (2H, m), 3.11 (4H, m), 3.30 (2H, m), 3.48 (2H, m), 3.64 (4H, m), 4.27 (2H, t), 5.60 (1H, q), 7.16 (1H, d), 7.83 (1H, d), 8.79 (1H, s), 10.64 (1H, s). LRMS: m/z 616 (M+1)⁺.

EXAMPLE 106

5-[5-(4-Methylpiperazin-1-ylsulphonyl)-2-n-propoxyphenyl]-2-[1R-(morpholin-4-ylcarbonyl) ethyl]-3-n-propyl-2,6-dihydro-7H-pyrazolo[4,3-d]-pyrimidin-7-one Obtained as a yellow foam (54%) from the title compound of Preparation 113 and 1-methylpiperazine using the procedure of Example 1. Found: C, 55.55; H, 6.86; N, 15.18. $C_{29}H_{41}N_7O_6S$; 0.16 $CH_2Cl_2$ requires C, 55.65; H, 6.62; N, 15.58%. δ (CDCl$_3$): 1.01 (3H, t), 1.13 (3H, t), 1.82 (3H, d), 1.90 (2H, m), 2.03 (2H, m), 2.25 (3H, s), 2.47 (4H, m), 3.00 (2H, m), 3.09 (4H, m), 3.30 (2H, m), 3.48 (2H, m), 3.66 (4H, m), 4.25 (2H, t), 5.59 (1H, q), 7.17 (1H, d), 7.83 (1H, d), 8.80 (1H, s), 10.63 (1H, s). LRMS: m/z 616 (M+1)$^+$.

EXAMPLE 107

5-[5-(4-Methylpiperazin-1-ylsulphonyl)-2-n-propoxyphenyl]-2-(2-morpholin-4-ylethyl)-3-n-propyl-2,6-dihydro-7H-pyrazolo[4,3-d]pyrimidin-7-one Obtained as a white solid (52%) from the title compound of Preparation 115 and 1-methylpiperazine using the procedure of Example 1. Found: C, 5.6.44; H, 7.16; N, 16.07. C$_{28}$H$_{41}$N$_7$O$_5$S; 0.50 H$_2$O requires C, 56.36; H, 7.09; N. 16.43%. δ (CDCl$_3$): 1.02 (3H, t), 1.12 (3H, t), 1.98 (2H, m), 2.02 (2H, m), 2.28 (3H, s), 2.50 (8H, m), 2.98 (4H, m), 3.10 (4H, m), 3.66 (4H, m), 4.22 (2H, t), 4.40 (2H, t), 7.16 (1H, d), 7.82 (1H, d), 8.80 (,1H, s); 10.56 (1H, s). LRMS: m/z 589 (M+1)$^+$.

EXAMPLE 108

5-[5-(4-Ethylpiperazin-1-ylsulphonyl)-2-n-propoxyphenyl]-2-(2-morphin-4-ylethyl)-3-n-propyl-2,6-dihydro-7H-pyrazolo[4,3-d]pyrimidin-7-one Obtained as a yellow oil (24%) from the title compound of Preparation 115 and 1-ethylpiperazine using the procedure of Example 1. Found: C, 57.04; H, 7.28; N, 15.46. C$_{29}$H$_{43}$N$_7$O$_5$S; 0.50 H$_2$O requires C, 57.03; H, 7.26; N, 16.05%. δ (CDCl$_3$): 1.04 (3H, t), 1.14 (3H, t), 1.90 (2H, m), 2.04 (2H, m), 2.40 (2H, q), 2.50 (8H, m), 3.00 (4H, m), 3.10 (4H, m), 3.68 (4H, m), 4.23 (2H, t), 4.40 (2H, t), 7.14 (1H, d), 7.82 (1H, d), 8.80 (1H, s), 10.56 (1H, s). LRMS: m/z 603 (M+1)$^+$.

EXAMPLE 109

5-{5-[4-(2-Hydroxyethyl)piperazin-1-ylsulphonyl]-2-n-propoxyphenyl}-2-(2-morpholin-4-ylethyl)-3-n-propyl-2,6-dihydro-7H-pyrazolo[4,3-d]pyrimidin-7-one Obtained as a white solid (36%) from the title compound of Preparation 115 and 1-(2-hydroxyethyl)piperazine using the procedure of Example 1. Found: C, 56.05; H, 7.02; N, 15.31. C$_{29}$H$_{43}$N$_7$O$_6$S requires C, 56.38; H. 7.02; N, 15.87%. δ (CDCl$_3$): 1.04 (3H, t), 1.14 (3H, t), 1.88 (2H, m), 2.04 (2H, m), 2.30 (1H, s), 2.48 (6H, m), 2.60 (4H, m), 2.96 (4H, m), 3.10 (4H, m), 3.57 (2H, t), 3.70 (4H, m), 4.24 (2H, t), 4.38 (2H, t), 7.17 (1H, d), 7.82 (1H, d), 8.80 (1H, s), 10.60 (1H, s). LRMS: m/z 619 (M+1)$^+$.

EXAMPLE 110

2-[2-(4-Methylpiperazin-1-yl)ethyl]-5-[5-(4-methylpiperazin-1-ylsulphonyl)-2-n-propoxyphenyl]-3-n-propyl-2,6-dihydro-7H-pyrazolo[4,3-d]pyrimidin-7-one Obtained as a white foam (43%) from the title compound of Preparation 116 and 1-methylpiperazine using the procedure of Example 1. Found: C, 56.20; H, 7.43; N, 17.78. C$_{29}$H$_{44}$N$_8$O$_4$S; 0.20 CH$_2$Cl$_2$ requires C, 56.38; H, 7.24; N, 18.14%. δ (CDCl$_3$): 1.02 (3H, t), 1.14 (3H, t), 1.86 (2H, m), 2.02 (2H, m), 2.26 (3H, s), 2.30 (3H, s), 2.46 (8H, m), 2.58 (4H, m), 2.97 (4H, m), 3.12 (4H, m), 4.20 (2H, t), 4.40 (2H, t), 7.14 (1H, d), 7.80 (1H, d), 8.80 (1H, s), 10.55 (1H, s). LRMS: m/z 602 (M+1)$^+$.

EXAMPLE 111

5-[5-(4-Ethylpiperazin-1-ylsulphonyl)-2-n-propoxyphenyl]-3-n-propyl-2-(2-pyrazol-1-ylethyl)-2,6-dihydro-7H-pyrazolo[4,3-d]pyrimidin-7-one Obtained as a white foam (45%) from the title compound of Preparation 118 and 1-ethylpiperazine using the procedure of Example 1. Found: C, 57.62; H, 6.59; N, 19.05. C$_{28}$H$_{38}$N$_8$O$_4$S requires C, 57.71; H, 6.57; N, 19.23%. δ (CDCl$_3$): 0.82 (3H, t), 0.98 (3H;t), 1.11 (3H, t), 1.44 (2H, m), 1.98 (2H, m), 2.38 (2H, m), 2.44 (2H, m), 2.48 (4H, m), 3.00 (4H, m), 4.20 (2H, t), 4.64 (2H, t), 4.76 (2H, t), 6.02 (1H, s), 6.86 (1H, s), 7.08 (1H, d), 7.54 (1H, s), 7.79 (1H, m), 8.70 (1H, s), 10.69 (1H, s). LRMS: m/z 583 (M+1)$^+$.

EXAMPLE 112

5-[5-(4-Ethylpiperazin-1-ylsulphonyl)-2-n-propoxyphenyl]-3-n-propyl-2-[2-(1,2,3-triazol-1-yl)ethyl]-2,6-dihydro-7H-pyrazolo[4,3-d]pyrimidin-7-one Obtained as a white foam (57%) from the title compound of Preparation 120 and 1-ethylpiperazine using the procedure of Example 1. Found: C, 55.13; H, 6.44; N; 21.41. C$_{27}$H$_{37}$N$_9$O$_4$S requires C, 55.56; H, 6.39; N, 21.60%. δ (CDCl$_3$): 0.82 (3H, t), 0.96 (3H, t), 1.14 (3H, t), 1.51. (2H, m), 2.00 (2H, m), 2.38 (2H, m), 2.50 (4H, m), 2.58 (2H, t), 3.04 (4H, m), 4.20 (2H, t)e 4.76 (2H, t), 5.04 (2H, t), 7.15 (2H, d), 7.63 (1H, s), 7.80 (2H, d), 8.72 (1H, s), 10.58 (1H, s). LRMS: m/z 584 (M+1)$^+$.

EXAMPLE 113

5-[5-(4-Methylpiperazin-1-ylsulphonyl)-2-n-propoxyphenyl]-3-n-propyl-2-[2-(1,2,4-triazol-1-yl)ethyl]-2,6-dihydro-7H-pyrazolo[4,3-d]pyrimidin-7-one Obtained as a white solid (33%) from the title compound of Preparation 122 and 1-methylpiperazine using the procedure of Example 1. Found: C, 54.58; H, 6.24; N, 21.57. C$_{26}$H$_{35}$N$_9$O$_4$S requires C, 54.82; H, 6.19; N, 22.13%. δ (CDCl$_3$): 0.86 (3H, t), 1.13 (3H, t), 1.55 (2H, m), 2.00 (2H, m), 2.24 (3H, s), 2.46 (4H, m), 2.62 (2H, t), 3.08 (4H, m), 4.22 (2H, t), 4.70 (2H, t), 4.90 (2H, t), 7.12 (1H, d), 7.66 (1H, s), 7.78 (1H, d), 7.92 (1H, s), 8.70 (1H, s), 10.60 (1H, s). LRMS: m/z 570 (M+1)$^+$.

EXAMPLE 114

5-[5-(4-Ethylpiperazin-1-ylsulphonyl)-2-n-propoxyphenyl]-3-n-propyl-2-[2-(1,2,4-triazol-1-yl)ethyl]-2,6-dihydro-7H-pyrazolo[4 3-d]pyrimidin-7-one Obtained as a white solid (37%) from the title compound of Preparation 122 and 1-ethylpiperazine using the procedure of Example 1. Found: C, 55.14; H, 6.37; N, 21.14. C$_{27}$H$_{37}$N$_9$O$_4$S requires C, 55.56; H, 6.39; N, 21.60%. δ (CDCl$_3$): 0.87 (3H, t), 0.98 (3H, m), 1.14 (3H, t), 1.57 (2H, m), 2.00 (2H, m), 2.38 (2H, m), 2.50 (4H, m), 2.62 (2H, t), 3.05 (4H, m), 4.22 (2H, t), 4.68 (2H, t), 4.88 (2H, t), 7.12 (1H, d), 7.66 (1H, s), 7.80 (1H, d), 7.92 (1H, s), 8.70 (1H, s), 10.60 (1H, s). LRMS: m/z 584 (M+1)$^+$.

EXAMPLE 115

5-[5-(4-Ethylpiperazin-1-ylsulphonyl)-2-n-propoxyphenyl]-2-(2-nitrophenyl)-3-n-propyl-2,6-dihydro-7H-pyrazolo[4,3-d]pyrimidin-7-one Obtained as a yellow foam (36%) from the title compound of Preparation 123 and 1-ethylpiperazine using the procedure of Example 1. δ (CDCl₃): 0.90 (3H, t), 0.99 (3H, m), 1.11 (3H, t), 1.75 (2H, m), 2.02 (2H, m), 2.38 (2H, m), 2.50 (4H, m), 2.85 (3H, t), 3.08 (4H, m), 4.20 (2H, t), 7.13 (1H, d), 7.58 (1H, d), 7.74 (3H, m), 8.17 (1H, d), 8.82 (1H, s), 10.64 (1H, s). LRMS: m/z 610 (M+1)⁺.

EXAMPLE 116

2-(2-Aminophenyl)-5-[5-(4-ethylpiperazin-1-ylsulphonyl)-2-n-propoxyphenyl]-3-n-propyl-2,6-dihydro-7H-pyrazolo[4,3-d]pyrimidin-7-one A stirred mixture of the title compound of Example 115 (622 mg, 1.02 mmol), 10% palladium on charcoal (100 mg), ethanol (10 ml) and ethyl acetate (30 ml) was hydrogenated at 345 kPa (50 psi) and 50° C. for 3 hours and then at room temperature for 18 hours. The resulting mixture was filtered, then the filtrate combined with an ethyl acetate wash of the filter pad and evaporated under reduced pressure to afford the title compound (100%) as a white powder. δ (CDCl₃): 0.87 (3H, t), 0.98 (3H, m), 1.12 (3H, t), 1.70 (2H, m), 2.01 (2H, q), 2.38 (2H, m), 2.48 (4H, m), 2.90 (2H, t), 3.08 (4H, m), 3.92 (2H, s), 4.23 (2H, t), 6.86 (2H, d), 7.13 (2H, d), 7.27 (1H, d), 7.81 (1H, d), 8.80 (1H, s), 10.62 (1H, s). LRMS: m/z 580 (M+1)⁺.

EXAMPLE 117

5-[5-(4-Ethylpiperazin-1-ylsulphonyl)-2-n-propoxyphenyl]-2-(2-methanesulphonamidophenyl)-3-n-propyl-2,6-dihydro-7H-pyrazolo[4,3-d]-pyrimidin-7-one Methanesulphonyl chloride (0.156 ml, 2.0 mmol) was added to a stirred solution of the title compound of Example 116 (583 mg, 1.0 mmol) in pyridine (8 ml), under nitrogen, and the resulting solution stirred at 50° C. for 18 hours, then evaporated under reduced pressure. The residue was partitioned between ethyl acetate and water, then the separated organic phase washed with brine, dried (MgSO₄) and evaporated under reduced pressure. The resulting brown foam was purified by column chromatography on silica gel, using an elution gradient of dichloromethane:methanol (100:0 to 99:1 to 98:2 to 97:3), to yield the title compound (32%) as a cream foam. Found: C, 53.96; H, 6.01; N, 14.38. $C_{30}H_{39}N_7O_6S_2$; 0.60 $H_2O$ requires C, 53.89; H, 6.06; N, 14.67%. δ (CDCl₃): 0.91 (3H, t), 1.01 (3H, t), 1.19 (3H, t), 1.75 (2H, m), 2.07 (2H, m), 2.40 (2H, q), 2.53 (4H, m), 2.93 (2H, t), 3.07 (3H, s), 3.09 (4H, m), 4.29 (2H, t), 7.16 (2H, m), 7.35 (2H, m), 7.57 (1H, t), 7.82 (2H, d), 8.80 (1H, s), 10.74 (1H, s). LRMS: m/z 658 (M+1)⁺.

EXAMPLE 118

5-[5-(4-Methylpiperazin-1-ylsulphonyl)-2n-propoxyphenyl]-2-(4-nitrophenyl)-3-n-propyl-2,6-dihydro-7H-pyrazolo[4,3-d]pyrimidin-7-one Obtained as a yellow foam (63%) from thetitle compound of Preparation 124 and 1-methylpiperazine using the procedure of Example 1. δ (CDCl₃): 0.96 (3H, t), 1.16 (3H, t), 1.80 (2H, m), 2.05 (2H, m), 2.27 (3H, s), 2.49 (4H, m), 3.10 (6H, m), 4.27 (2H, t), 7.18 (1H, d), 7.83 (2H, d), 7.86 (1H, d), 8.46 (2H, d), 8.84.(1H, s), 10.75 (1H, s). LRMS: m/z 596 (M+1)⁺.

EXAMPLE 119

2-(4-Aminophenyl)-5-[5-(4-methylpiperazin-1-ylsulphonyl)-2-n-propoxyphenyl]-3-n-propyl-2,6-dihydro-7H-pyrazolo[4,3-d]pyrimidin-7-one Obtained as a yellow foam (71%) from the title compound of Example 118 using the procedure of Example 116. δ (CDCl₃): 0.89 (3H, t), 1.16 (3H, t), 1.78 (2H, m), 2.04 (2H, m), 2.27 (3H, s),2.49 (4H, m), 2.96 (2H, t), 3.10 (4H, m), 4.22 (2H, t), 6.76 (2H, d), 7.18 (1H, d), 7.29 (2H, d), 7.83 (1H, d), 8.82 (1H, s), 10.59 (1H, s). LRMS: m/z 566 (M+1)⁺.

EXAMPLE 120

2-(4-Methanesulphonamidophenyl)-5-[5-(4-methylpiperazin-1-ylsulphonyl)-2-n-propoxyphenyl]-3-n-propyl-2,6-dihydro-7H-pyrazolo[4,3-d]-pyrimidin-7-one Obtained as a yellow foam (55%) from the title compound of Example 119 and methanesulphonyl chloride using the procedure of Example 117. Found: C, 53.05; H. 5.72; N; 14.94. $C_{30}H_{39}N_7O_6S_2$; 0.20 $H_2O$ requires C, 53.08; H, 5.71; N, 14.84%. δ (CDCl₃): 0.97 (3H, t), 1.19 (3H, t), 1.80 (2H, m), 2.07 (2H, m), 2.30 (3H, s), 2.52 (4H, m), 3.02 (2H, t), 3.16 (7H, m), 4.28 (2H, t), 6.90 (1H, d), 7.19 (1H, d), 7.42 (2H, d), 7.57 (2H, d), 7.85 (1H, d), 8.83 (1H, s), 10.72 (1H, s). LRMS: m/z 644 (M+1)⁺.

EXAMPLE 121

5-[5-(4-Ethylpiperazin-1-ylsulphonyl)-2-n-propoxyphenyl]-2-(4-nitrophenyl)-3-n-propyl-2,6-dihydro-7H-pyrazolo[4,3-d]pyrimidin-7-one Obtained as a yellow solid (82%) from the title compound of Preparation 124 and 1-ethylpiperazine using the procedure of Example 1. δ (CDCl₃): 0.96 (3H, t), 1.16 (3H, t), 1.42 (3H, t), 1.80 (2H, m), 2.02 (2H, m), 2.24 (2H, m), 2.44 (4H, m), 3.10 (6H, m), 4.31 (2H, t), 7.18 (1H, d), 7.80 (2H, d), 7.86 (1H, d), 8.46 (2H, d), 8.88 (1H, s.), 10.79 (1H, s). LRMS: m/z 610 (M+1)⁺.

EXAMPLE 122

2-(4-Aminophenyl)-5-[5-(4-ethylpiperazin-1-ylsulphonyl)-2-n-propoxyphenyl]-3-n-propyl-2,6-dihydro-7H-pyrazolo[4,3-d]pyrimidin-7-one Obtained as a white solid (64%) from the title compound of Example 121 using the procedure of Example 116. δ (CDCl₃): 0.91 (3H, t), 1.16 (3H, t), 1.40,(3H, t), 1.83 (2H, m), 2.05 (2H, m), 2.25 (2H, m), 2.49 (4H, m), 2.96 (2H, t), 3.10 (4H, m), 4.28 (2H, t), 6.80 (2H, d), 7.18 (1H, d), 7.32 (2H, d), 7.83 (1H, d), 8.86 (1H, s), 10.64 (1H, s). LRMS: m/z 580 (M+1)⁺.

EXAMPLE 123

2-(4-Ethanesulphonamidophenyl)-5-[5-(4-ethylpiperazin-1-ylsulphonyl)-2-n-propoxyphenyl]-3-n-propyl-2,6-dihydro-7H-pyrazolo[4,3-d]pyrimidin-7-one Obtained as a pink solid (52%) from the title compound of Example 122 and ethanesulphonyl chloride using the procedure of Example 117. Found: C, 55.07; H, 6.18; N, 14.39. $C_{31}H_{41}N_7O_6S_2$ requires C, 55.42; H, 6.15; N, 14.59%. δ (CDCl₃): 0.96 (3H, t), 1.18 (3H, t), 1.42 (3H, t), 1.78 (2H, m), 2.02 (2H, m), 2.42 (2H, m), 2.58 (4H, m), 3.02 (2H, t), 3.16 (4H, m), 3.20 (2H, m), 4.22 (2H, t), 7.18 (2H, d), 7.43 (3H, m), 7.82 (2H, d), 8.80 (1H, s), 10.70 (1H, s). LRMS: m/z 672 (M+1)⁺.

EXAMPLE 124

5-[5-(4-Ethylpiperazin-1-ylsulphonyl)-2-n-propoxyphenyl]-3-n-propyl-2-[4-(prop-2-ylsulphonamido)phenyl]-2,6-dihydro-7H-pyrazolo[4,3-d]pyrimidin-7-one Obtained as a solid (28%) from the title compound of Example 122 and 2-propanesulphonyl chloride using the procedure of Example 117. Found: C, 53.59; H, 6.15; N, 13.34. $C_{32}H_{43}N_7O6S_2$; 0.17 $H_2O$ requires C, 53.64; H, 6.53; N, 13.68%. δ ($CDCl_3$): 0.92 (3H, t); 1.03 (3H, t), 1.18 (3H, t), 1.42 (6H, m), 1.78 (2H, m), 2.07 (2H, m), 2.38 (2H, t), 2.57 (4H, m), 3.02 (2H, t), 3.16 (4H, m), 3.38 (1H, m), 4.22.(2H, t), 7.18 (2H, d), 7.45 (3H, m), 7.80 (2H, d), 8.80 (1H, s), 10.71 (1H, s). LRMS: m/z 686 $(M+1)^+$.

EXAMPLE 125

5-[5-(4-Methylpipierazin-1-ylsulphonyl)-2-n-propoxyphenyl]-3-n-propyl-2-pyrimidin-2-yl-2,6-dihydro-7H-pyrazolo[4,3-d]pyrimidin-7-one Obtained as a white foam (40%) from the title compound of Preparation 125 and 1-methylpiperazine using the procedure of Example 1. δ ($CDCl_3$): 1.00 (3H, t), 1.18 (3H, t), 1.80 (2H, m), 2.06 (2H, m), 2.28 (3H, s), 2.50 (4H, m), 3.13 (4H, m), 3.46 (2H, t). 4.26 (2H, t), 7.18 (1H, d), 7.40 (1H, m), 7.85 (1H, d), 8.88 (1H, s), 8.92 (2H, m), 10.70 (1H, s). LRMS: m/z 553 $(M+1)^+$.

EXAMPLE 126

2-Cyclobutylmethyl-5-[2-ethoxy-5-(4-methylpiperazin-1-ylsulphonyl)phenyl]-3-n-propyl-2,6-dihydro-7H-pyrazolo[4,3-d]pyrimidin-7-one Obtained as a white solid (84%) from the title compound of Preparation 126 and 1-methylpiperazine using the procedure of Example 1. δ ($CDCl_3$): 1.01 (3H, t), 1.60 (3H, t), 1.88 (6H, m), 2.08 (2H, m), 2.30 (3H, s), 2.52 (4H, m), 2.98 (3H, m), 3.12 (4H, m), 4.33 (4H, m), 7.15 (1H, d), 7.81 (1H, d), 8.79 (1H, s), 10.54 (1H, s). LRMS: m/z 529 $(M+1)^+$.

EXAMPLE 127

2-Cyclobutylmethyl-5-[5-(4-methylpiperazine-1-ylsulphonyl-2-n-propoxyphenyl]-3-n-propyl-2,6-dihydro-7H-pyrazolo[4,3-d]pyrimidin-7-one Obtained as a white foam (56%) from the title compound of Preparation 127 and 1-methylpiperazine using the procedure of Example 1.

Found: C, 59.24; H, 7.01; N, 15.24. $C_{27}H_{38}N_6O_4S$ requires C, 59.76; H, 7.06; N, 15.44%. δ ($CDCl_3$): 1.04 (3H, t), 1.12 (3H, t), 1.90 (6H, m), 2.06 (4H, m), 2.30 (3H, s), 2.50 (4H, m), 2.98 (3H, m), 3.12 (4H, m), 4.22 (2H, t), 4.30 (2H, d), 7.14 (1H, d), 7.80 (1H, d), 8.78 (1H, s), 10.54 (1H, s). LRMS: m/z 543 $(M+1)^+$.

EXAMPLE 128

5-[5-(4-Methylpiperazine-1-ylsulphonyl)-2-n-propoxyphenyl]-2-(1-oxidopyridin-2-yl)methyl-3-n-propyl-2,6-dihydro-7H-pyrazolo[4,3-d]pyrimidin-7-one 3-Chloroperoxybenzoic acid. (50–55%; 152 mg, 0.44 mmol) was added to a stirred solution of the title compound of Example 6 (108 mg, 0.19 mmol) in dichloromethane (5 ml), under nitrogen, and stirring continued for 18 hours. The reaction mixture was diluted with dichloromethane (20 ml), washed successively with 5% aqueous sodium metabisulphite solution (20 ml), 10% aqueous potassium carbonate solution (20 ml) and brine (15 ml), then dried ($MgSO_4$) and evaporated under reduced pressure. The resulting yellow foam was purified by column chromatography on silica gel, using an elution gradient of dichloromethane:methanol: 0.880 aqueous ammonia (100:1:1 to 100:3:1), to give the title compound (36 mg) as an orange solid. δ ($CDCl_3$): 1.00 (3H, t), 1.15 (3H, t), 1.79 (2H, m), 2.07 (2H, m), 2.28 (3H, m), 2.48 (4H, m), 3.00 (2H, t), 3.12 (4H, m), 4.27 (2H, t), 5.82 (2H, s), 6.79 (1H, d), 7.22 (3H, m), 7.85 (1H, d), 8.30 (1H, d), 8.80 (1H, s), 10.66 (1H, s). LRMS: m/z 582 $(M+1)^+$.

EXAMPLE 129

5-[5-(4-Ethylpiperazin-1-ylsulphonyl)-2-n-propoxyphenyl]-2-(1-oxidopyridin-2-yl)methyl-3-n-propyl-2,6-dihydro-7H-pyrazolo[4,3-d]pyrimidin-7-one Obtained as a yellow foam (63%) from the title compound of Example 12 using the procedure of Example 128. Found: C, 57.04; H, 6.14; N, 15.80. $C_{29}H_{37}N_7O_5S$; 0.25 $CH_2Cl_2$ requires C, 56.95; H, 6.13; N, 15.89%. δ ($CDCl_3$): 0.99 (6H, m), 1.19 (3H, t), 1.80 (2H, m), 2.02 (2H, m), 2.41 (2H, q), 2.52 (4H, m), 3.01 (2H, t), 3.09 (4H, m), 4.26 (2H, t), 5.80 (2H, s), 6.89 (1H, d), 7.20 (3H, m), 7.83 (1H, d), 8.28 (1H, d), 8.80 (1H, s), 11.63 (1H, s). LRMS: m/z 596 $(M+1)^+$.

EXAMPLE 130

3-Ethyl-5-[2-(2-methoxyethoxy)-5-(4-methylpiperazin-1-ylsulphonyl)phenyl]-2-(pyridin-2-yl)methyl-2,6-dihydro-7H-pyrazolo[4,3-d]pyrimidin-7-one Obtained as white foam (85%) from the title compound of Preparation 133 and 1-methylpiperazine using the procedure of Example 1. Found: C, 55.82; H, 5.84; N, 16.54. $C_{27}H_{33}N_7O_5S$; 0.75 $H_2O$ requires C, 55.80; H, 5.98; N, 16.87%. δ($CDCl_3$): 1.30 (3H, t), 2.26 (3H, s), 2.48 (4H, m), 3.01 (2H, q), 3.10 (4H, m), 3.58 (3H, s), 3.87 (2H, t), 4.42 (2H, t), 5.67 (2H, s), 7.07 (1H, d), 7.14 (1H, d), 7.20 (1H, m), 7.61 (1H, m), 7.81 (1H, d), 8.57 (1H, d), 8.70 (1H, s), 10.86 (1H, s),. LRMS: m/z 569 $(M+2)^+$.

EXAMPLE 131

3-Ethyl-5-[5-(4-ethylpiperazin-1-ylsulphonyl)-2-(2-methoxyethoxy)phenyl]-2-(pyridin-2-yl)methyl-2,6-dihydro-7H-pyrazolo[4,3-d]pyrimidin-7-one Obtained as a white foam (73%) from the title compound of Preparation 133 and 1-ethylpiperazine using the procedure of Example 1. Found: C,57.08; H, 6.04; N, 16.51. $C_{28}H_{35}N_7O_5S$; 0.50 $H_2O$ requires C,56.93; H, 6.14; N, 16.60%. δ($CDCl_3$): 1.01 (3H, t), 1.30 (3H, t), 2.39 (2H, q) 2.53 (4H, m), 3.01 (2H, q), 3.10 (4H, m), 3.59 (3H, s), 3.87 (2H, t) 4.41 (2H, t), 5.68 (2H, s), 7.08 (1H, d), 7.15 (1H, d) 7.20 (1H, m), 7.61 (1H, m), 7.82 (1H, d), 8.57 (1H, d), 8.70 (1H, s), 10.85 (1H, s). LRMS: m/z 582 $(M+1)^+$.

Preparation 1

Ethyl 3-ethyl-1H-pyrazole-5-carboxylate

Ethanolic sodium ethoxide solution (21% w/w; 143 ml, 0.39 mol) was added dropwise to a stirred, ice-cooled solution of diethyl oxalate (59.8 ml, 0.44 mol) in absolute ethanol (200 ml) under nitrogen and the resulting solution stirred for 15 minutes. Butan-2-one (39 ml, 0.44 mol) was then added dropwise, the cooling bath removed, the reaction mixture stirred for 18 hours at room temperature and then for 6 hours at 40° C., then the cooling bath reintroduced. Next, glacial acetic acid (25 ml, 0.44 mol) was added dropwise, the resulting solution stirred for 30 minutes at 0° C., hydrazine hydrate (20 ml, 0.44 mol) added dropwise, then the reaction mixture allowed to warm to room temperature and maintained there over a period of 18 hours, before being evaporated under reduced pressure. The residue was partitioned between dichloromethane (300 ml) and water (100 ml), then the organic phase separated, washed with water (2×100 ml), dried ($Na_2SO_4$) and concentrated under reduced pressure to give the title compound (66.0 g). δ ($CDCl_3$): 1.04 (3H, t), 1.16 (3H, t), 2.70 (2H, q), 4.36 (2H, q), 6.60 (1H, s). LRMS: m/z 169 $(M+1)^+$.

Preparation 2

3-Ethyl-1H-pyrazole-5-carboxylic acid

Aqueous sodium hydroxide solution (10M; 100 ml, 1.0 mol) was added dropwise to a stirred suspension of the title compound of Preparation 1 (66.0 g, 0.39 mol) in methanol and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g). δ ($DMSO_{d6}$): 1.13 (3H, t), 2.56 (2H, q), 6.42 (1H, s).

Preparation 3

4-Nitro-3-n-propyl-1H-pyrazole-5-carboxylic acid

Fuming sulphuric acid (17.8 ml) was added dropwise to stirred, ice-cooled fuming nitric acid (16.0 ml), the resulting solution heated to 50° C., then 3-n-propyl-1H-pyrazole-5-carboxylic acid (Chem. Pharm. Bull., 1984, 32, 1568; 16.4 g, 0.106 mol) added portionwise over 30 minutes whilst maintaining the reaction temperature below 60° C. The resulting solution was heated for 18 hours at 60° C., allowed to cool, then poured onto ice: The white precipitate was collected, washed with water and dried by suctiod to yield the title compound (15.4 g), m.p. 170–172° C. Found: C, 42.35; H, 4.56; N, 21.07. $C_7H_9N_3O_4$ requires C, 42.21; H, 4.55; N, 21.10%. δ ($DMSO_{d6}$): 0.90 (3H, t), 1.64(2H, m), 2.83 (2H, m), 14.00 (1H, s).

Preparation 4

3-Ethyl-4-nitro-1H-pyrazole-5-carboxylic acid

Obtained from the title compound of Preparation 2, by analogy with Preparation 3, as a brown solid (64%). δ ($DMSO_{d6}$): 1.18 (3H, t), 2.84 (2H, m), 13.72 (1H, s).

Preparation 5

4-Nitro-3-n-propyl-1H-pyrazole-5-carboxamide

A solution of the title compound of Preparation 3 (15.4 g, 0.077 mol) in thionyl chloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound (14.3 g), m.p. 197–199° C. Found: C, 42.35; H, 5.07; N, 28.38. $C_7H_{10}N_4O_3$ requires C, 42.42; H, 5.09; N, 28.27%. δ ($DMSO_{d6}$): 0.90 (3H, t), 1.68 (2H, m), 2.86 (2H, m), 7.68 (1H, s), 8.00 (1H, s).

Preparation 6

3-Ethyl-4-nitro-1H-pyrazole-5-carboxamide

Obtained from the title compound of Preparation 4, by analogy with Preparation 5, as a white solid (90%). δ ($DMSO_{d6}$): 1.17 (3H, t), 2.87 (2H, m), 7.40 (1H, s), 7.60 (1H, s), 7.90 (1H, s). LRMS: m/z 185 $(M+1)^+$.

Preparation 7

4-Amino-3-n-propyl-1H-pyrazole-5-carboxamide

A stirred mixture of the title compound of Preparation 5 (10.0 g, 0.050 mol), 10% palladium on charcoal (1.5 g) and ethanol (400 ml) was hydrogenated for 18 hours at 345 kPa. (50 psi) and 50° C., then filtered. The filtrate was combined with an ethanol wash (200 ml) of the filter pad and then evaporated under reduced pressure to give an orange solid which, on crystallisation from ethyl acetate:methanol, afforded the title compound (6.8 g) as a white solid, m.p. 196–201° C. Found: C, 48.96; H, 6.98; N, 32.08. $C_7H_{12}N_4O$; 0.25 $H_2O$ requires C, 48.68; H, 7.30; N, 32.44%. δ ($DMSO_{d6}$): 0.88 (3H, t), 1.55 (2H, m), 2.46 (2H, t), 4.40 (2H, s), 7.00 (1H, s), 7.12 (1H, s), 12.20 (1H, s).

Preparation 8

4-Amino-3-ethyl-1H-pyrazole-5-carboxamide

Obtained from the title compound of Preparation 6, by analogy with Preparation 7, as a brown solid (80%). δ (DMSOd6): 1.08 (3H, t), 2.45 (2H, q), 4.50 (1H, s), 6.88 (1H, s), 7.10 (1H, s), 7.26 (2H, s). LRMS: m/z 155 $(M+1)^+$.

Preparation 9

4-(2-n-Propoxybenzamido)-3-n-propyl-1H-pyrazole-5-carboxamide

A solution of 2-n-propoxybenzoyl chloride (57.6 g, 0.291 mol) in dichloromethane (50 ml) was added dropwise to a stirred, ice-cooled suspension of the title compound of Preparation 7 (35.0 g, 0.208 mol) in dry pyridine (350 ml) and the resulting mixture stirred for 18 hours at room temperature, then evaporated under reduced pressure. The residue was azeotroped with toluene (2×100 ml) and the resulting brown solid triturated with other (100 ml) to give the title compound (83.0 g) as a beige solid. δ ($CH_3OH_{d4}$): 0.92 (3H, t), 1.14 (3H, t), 1.65 (2H, m), 1.94 (2H, m), 2.80 (2H, t), 4.20 (2H, t), 7.08 (1H, m), 7.18 (1H, d), 7.52 (1H, m), 8.04 (1H, d). LRMS: m/z 331 $(M+1)^+$.

Preparation 10

3-Ethyl-4-(2-n-propoxybenzamido)-1H-pyrazole-5-carboxamide

Obtained from the title compound of Preparation 8, by analogy with Preparation 9, as a beige solid (68%). δ (DMSOd6): 0.93 (3H, t), 1.12 (3H, t), 1.86 (2H, q), 2.71 (2H, m), 4.15 (2H, t), 7.06 (1H, m), 7.20 (1H, d), 7.20 (1H, s), 7.40 (1H, s), 7.50 (1H, m), 7.92 (1H, d), 10.20 (1H, s). LRMS: m/z 317 $(M+1)^+$.

Preparation 11

4-(2-Ethoxybenzamido)-3-n-propyl-1H-pyrazole-5-carboxamide

Obtained from the title compound of Preparation 7 and 2-ethoxybenzoyl chloride, by analogy with Preparation 9, as a white solid (64%), m.p. 209–211° C. Found: C, 60.73; H, 6.41; N, 17.80. $C_{16}H_{20}N_4O_3$ requires C, 60.74; H, 6.37; N, 17.71%. δ (DMSO$_{d6}$): 0.82 (3H, t), 1.42 (3H, t), 1.56 (2H, m), 1.75 (2H, t), 4.27 (2H, q), 7.07 (1H, m), 7.22 (2H, m), 7.52 (2H, m), 8.00 (1H, d), 10.40 (1H, s), 12.96 (1H, s).

Preparation 12

5-(2-n-Propoxyphenyl)-3-n-propyl-1,6-dihydro-7H-pyrazolo[4,3-d]pyrimidin-7-one

Potassium t-butoxide (93.0 g, 0.832 mol) was added portionwise to a stirred solution of the title compound of Preparation 9 (83.0 g, 0.25 mol),in propan-2-ol (800 ml) under nitrogen and the mixture heated for 18 hours under reflux, then allowed to cool. Water (100 ml) was added, to produce a homogeneous solution which was acidified to pH 6 with 2M hydrochloric acid. The resulting white precipitate was collected and dried by suction to provide the title compound (37.4 g). Found: C, 65.36; H, 6.49; N, 17.99. $C_{17}H_{20}N_4O_2$ requires C, 65.37; H, 6.45; N, 17.94%. δ (CDCl$_3$): 1.05 (3H, t), 1.16 (3H, t), 2.00 (4H, m), 3.04 (2H, t), 4.20 (2H, t), 7.07 (1H, d), 7.16 (1H, m), 7.48 (1H, m), 8.52 (1H, d), 11.30 (1H, s), 12.25 (1H, s). LRMS: m/z 313 $(M+1)^+$.

Preparation 13

3-Ethyl-5-(2-n-propoxyphenyl)-1,6-dihydro-7H-pyrazolo[4,3-d]pyrimidin-7-one

Obtained from the title compound of Preparation 10, by analogy with Preparation 12, as a white solid (85%). δ (DMSO$_{d6}$): 0.95 (3H, t), 1.15 (3H, t), 1.72 (2H, m), 2.84 (2H, q), 4.03 (2H, t), 7.06 (1H, m), 7.15 (1H, d), 7.44 (1H, m), 7.72 (1H, d), 11.83 (1H, s), 13.64 (1H, s). LRMS: m/z299 $(M+1)^+$.

Preparation 14

5-(2-Ethoxyphenyl)-3-n-propyl-1,6-dihydro-7H-pyrazolo[4,3-d]pyrimidin-7-one

Obtained from the title compound of Preparation 11, by analogy with Preparation 12, as a white solid (88%), m.p. 199–201° C. Found: C, 64.44; H, 6.19; N, 18.44. $C_{16}H_{18}N_4O_2$ requires C, 64.41; H, 6.08; N, 18.78%. δ (CDCl$_3$): 1.08 (3H, t), 1.65 (3H, t), 1.98 (2H, m), 3.04 (2H, t), 4.36 (2H, q), 7.10 (1H, d), 7.20 (1H, m), 7.50 (1H, m), 8.57 (1H, d), 11.36 (1H, s), 11.88 (1H, s).

Preparation 15

Alkylation of 5-(2-alkoxyphenyl)-3-alkyl-1,6-dihydro-7H-pyrazolo[4,3-d]pyrimidin-7-ones Five general procedures, methods A to E, have been employed for the N-alkylatidn of the title compounds of Preparations 12, 13 and 14. In several cases, both the N1- and N2-isomers can be isolated from the same reaction.

Method A

The alkyl halide (2.75 mmol) was added to a stirred suspension of the pyrazolo[4,3-d]pyrimidinone substrate (2.5 mmol) in 1M aqueous sodium hydroxide solution (7.25 mmol) under nitrogen and the reaction mixture heated for 72 hours at50° C., then allowed to cool. The resulting mixture was extracted with ethyl acetate (2×25 ml) and the combined extracts dried (MgSO$_4$) and evaporated under reduced pressure to furnish the crude product, which was purified by column chromatography on silica gel.

Method B

A 60% w/w dispersion of sodium hydride in mineral oil (0.39 mmol) was added to a stirred, ice-cooled solution of the substrate (0.39 mmol) in anhydrous tetrahydrofuran (8 ml) under nitrogen. After 1 hour at 0° C., the alkyl halide (0.43 mmol) was added and the reaction mixture heated for 24 hours at 45° C., then allowed to cool. The resulting mixture was evaporated under reduced pressure and the residue partitioned between ethyl acetate (40 ml) and brine (30 ml). The organic phase was separated, dried (MgSO$_4$) and evaporated under reduced pressure to afford the crude product, which was purified by column chromatography on silica gel.

Method C

A 2M solution of sodium bis(trimethylsilyl)amide in tetrahydrofuran (2.2 mmol) was added dropwise to a stirred, ice-cooled solution of the substrate (2 mmol) in anhydrous tetrahydrofuran (8 ml) under nitrogen and the solution stirred for 1 hour at 0° C. before being cooled to −70° C. The alkyl halide (2 mmol) was then added, the cooling bath removed and the resulting solution stirred for 24 hours at room temperature, then evaporated under reduced pressure. The residue was partitioned between ethyl acetate (40 ml) and aqueous sodium bicarbonate solution (30 ml), then the organic phase separated, dried (MgSO$_4$) and evaporated under reduced pressure to yield the crude product, which was purified by column chromatography on silica gel.

Alternatively, a 0.5M solution of potassium bis(trimethylsilyl)amide in toluene may be used, with anhydrous toluene as solvent, and the alkylation conducted at about 40° C. for 20 hours.

Method D

A solution of the substrate (4.8 mmol), the alkyl halide (4.8 mmol) and Aliquat (TM) 336 (150 mg) in dichloromethane (80 ml) was added to stirred 1M aqueous sodium hydroxide solution (15 mmol) under nitrogen. The biphasic mixture was vigorously stirred for 72 hours at room temperature, then the aqueous phase was separated and extracted with ethyl acetate (2×25 ml). The extracts were combined,with the organic phase and this solution dried (MgSO$_4$) and evaporated under reduced pressure to give the crude product, which was purified by column chromatography on silica gel.

Method E

Triphenylphosphine (1.77 mmol) and the alkanol (1.77 mmol) were added to a stirred solution of the substrate (1.60 mmol) in anhydrous tetrahydrofuran (10 ml). The resulting solution was cooled to −5° C. and diethyl azodicarboxylate (1.77 mmol) added dropwise, then the reaction mixture allowed to warm to room temperature, stirred for 18 hours and evaporated under reduced pressure. The residue was partitioned between ethyl acetate (30 ml) and water (30 ml), then the organic phase separated, combined with an ethyl acetate extract (50 ml) of the aqueous phase, dried (Na$_2$SO$_4$) and evaporated under reduced pressure to yield the crude product, which was purified by column chromatography on silica gel.

Preparation 16

3-Ethyl-5-(2-n-propoxyphenyl)-1-(pyridin-2-yl)methyl-1,6-dihydro-7H-pyrazolo[4,3-d]pyrimidin-7-one Obtained as a white foam (15%) from the title compound of Preparation 13 and 2-chloromethylpyridine, using the procedure of Preparation 15B. δ (CDCl$_3$): 1.18 (3H, t), 1.43 (3H, t), 2.00 (2H, m), 3.02 (2H, q), 4.18 (2H, t), 5.95 (2H, s), 7.03 (2H, m), 7.16 (2H, m), 7.46 (1H, m), 7.60 (1H, m), 8.52 (1H, d), 8.58 (1H, d), 11.20 (1H, s). LRMS m/z 390 (M+1)+.

Preparation 17

5-(2-n-Propoxyphenyl)-3-n-propyl-1-(pyridin-2-yl) methyl-1,6-dihydro-7H-pyrazolo[4,3-d]pyrimidin-7-one Obtained as a white foam (22%) from the title compound of Preparation 12 and 2-chloromethylpyridine, using the procedure of Preparation 15D. δ (CDCl$_3$): 1.01 (3H, t), 1.17 (3H, t), 1.90 (2H, m), 2.00 (2H, m), 2.99 (2H, t), 4.20 (2H, t), 5.96 (2H, s), 6.99 (1H, d), 7.05 (1H, d), 7.17 (2H, m), 7.44 (1H, m), 7.60 (1H, m), 8.54 (1H, d), 8.59 (1H, d), 11.20 (1H, s).

LRMS: m/z 404 (M+1)+.

Preparation 18

3-Ethyl-5-(2-n-propoxyphenyl)-2-(pyridin-2-yl) methyl-2,6-dihydro-7H-pyrazolo[4,3-d]pyrimidin-7-one Obtained as a white solid (22%) from the title compound of Preparation 13 and 2-chloromethylpyridine, using the procedure of Preparation 15B.

A yield of 43% may be achieved using the procedure of Preparation 15C. δ (CDCl$_3$): 1.12 (3H, t), 1.30 (3H, t), 1.99 (2H, m), 3.00 (2H, q), 4.17 (2H, t), 5.68 (2H, s), 7.00–7.14 (3H, m), 7.20 (1H, m), 7.42, (1H, m), 7.60 (1H, m), 8.40 (1H, d), 8.58 (1H, d), 10.87 (1H, s). LRMS: m/z 390 (M+1)+.

Preparation 19

5-(2-Ethoxyphenyl)-3-n-propyl-2-(pyridin-2-yl) methyl-2,6-dihydro-7H-pyrazolo[4,3-d]pyrimidin-7-one Obtained as a white foam (59%) from the title compound of Preparation 14 and 2-chloromethylpyridine, using the procedure of Preparation 15B. δ (CDCl$_3$): 0.98 (3H, t), 1.60 (3H, t), 1.76 (2H, m), 2.98 (2H, t), 4.30 (2H, q), 5.70 (2H, s), 7.06 (2H, m), 7.15 (1H, m), 7.22 (1H, m), 7.44 (1H, m), 7.62 (1H, m), 8.41 (1H, d), 8.59 (1H, d), 10.90 (1H, s). LRMS: m/z 390 (M+1)+.

Preparation 20

5-(2-n-Propoxyphenyl)-3-n-propyl-2-(pyridin-2-yl) methyl-2,6-dihydro-7H-pyrazolo[4,3-d]pyrimidin-7-one Obtained as a white foam (54%) from the title compound of Preparation 12 and 2-chloromethylpyridine, using the procedure of Preparation 15B. δ (CDCl$_3$): 0.98 (3H, t), 1.16 (3H, t), 1.77 (2H, m), 2.00 (2H, m), 2.99 (2H, t), 4.19 (2H, t), 5.74 (2H, s), 7.04–7.16 (1H, m), 7.20 (1H, m), 7.44 (1H, m), 7.64 (1H, m), 8.41 (1H, d), 8.59 (1H, d), 10.90 (1H, s). LRMS: m/z 404 (M+1)+.

Preparation 21

5-(2-n-Propoxyphenyl)-3-n-propyl-2-(pyridin-3-yl) methyl-2,6-dihydro-7H-pyrazolo[4,3-d]pyrimidin-7-one Obtained as a cream foam (32%) from the title compound of Preparation 12 and 3-chloromethylpyridine, using the procedure of Preparation 15B. δ (CDCl$_3$): 0.98 (3H, t), 1.14 (3H, t), 1.78 (2H, m), 2.00 (2H, m), 2.92 (2H, t), 4.19 (2H, t), 5.58 (2H, s), 7.04 (1H, d), 7.14 (1H, m), 7.24 (1H, m), 7.43 (1H, m), 7.48 (1H, m), 8.40 (1H, d), 8.59,(2H, m), 10.91 (1H, s). LRMS: m/z 404 (M+1)+.

Preparation 22

4-(2-Phenylethenyl)pyridazine

Zinc chloride (820 mg, 6 mmol) was added to a stirred mixture of benzaldehyde (6.11 ml, 60 mmol) and 4-methylpyridazine (2.83 g, 30 mmol) and the resulting mixture heated for 20 hours at 150° C. The cool reaction mixture was partitioned between dichloromethane (40 ml) and 2M aqueous sodium hydroxide solution (20 ml), then the organic phase separated, combined with a dichloromethane extract (80 ml) of the aqueous phase, dried (Na$_2$SO$_4$) and evaporated under reduced pressure. The residual pale brown oil was purified by column chromatography on silica gel, using dichloromethane:methanol (99:1) as eluant, to give the title compound (3.65 g) as a pale brown solid. Found: C, 78.95; H, . 5.52; N, 15.39. C$_{12}$H$_{10}$N$_2$ requires C, 79.10; H, 5.53; N, 15.37%. δ (CDCl$_3$): 6.96 (1H, d), 7.45 (5H, m), 7.55 (2H, m), 9.12 (1H, d), 9.30 (1H, s). LRMS: m/z 183 (M+1)+.

Preparation 23

3-(2-Phenylethenyl)pyridazine

Obtained as a solid (59%) from 3-methylpyridazine, using the procedure of Preparation 22. δ (CDCl$_3$): 7.12 (1H, d), 7.34 (3H, m), 7.56 (2H, d), 7.72 (1H, d), 8.37 (1H, s), 8.50 (1H, s), 8.60 (1H, s). LRMS: m/z 183 (M+1)+.

Preparation 24

4-(2-Phenylethenyl)pyrimidine

Obtained as a solid (77%) from 4-methylpyrimidine, using the procedure of Preparation 22. δ (CDCl$_3$): 7.06 (1H, d), 7.36 (4H, m), 7.58 (2H, m), 7.92 (1H, d), 8.69 (1H, d), 9.14 (1H, s).

Preparation 25

4-Hydroxymethylpyridazine

Ozone was bubbled through a stirred solution of the title compound of Preparation 22 (3.60 g, 0.02 mol) in methanol (150 ml) at -10° C. After 30 minutes the mixture was purged with nitrogen, sodium borohydride (750 mg, 0.02 mol) added portionwise and the resulting solution stirred for 2 hours at room temperature. The reaction mixture was acidified with 2M hydrochloric acid, then basified with 0.880 aqueous ammonia solution and evaporated under reduced pressure. Purification of the residue by column chromatography on silica gel, using an elution gradient of dichlororethane:methanol (98:2 to 96:4), provided the title compound (1.64 g) as a tan-coloured solid. Found: C, 54.26; H, 5.42; N, 25.01. C$_5$H$_6$N$_2$O requires C, 54.54; H, 5.49; N, 25.44%. δ (CDCl$_3$): 3.12 (1H, s), 4.82 (2H, s), 7.54 (1H, d), 9.12 (1H, d), 9.16 (1H, s). LRMS: m/z 111 (M+1)+.

Preparation 26

3-Hydroxymethylpyridazine

Obtained as a solid (76%) from the title compound of Preparation 23, using the procedure of Preparation 25. δ (CDCl$_3$): 3,.66. (1H, s), 4.92 (2H, s), 7.48 (2H, m), 9.06 (1H, d).

Preparation 27

4-Hydroxymethylpyrimidine

Obtained as a yellow solid (83%) from the title compound of Preparation 24, using the procedure of Preparation 25. δ (CDCl$_3$): 2.88: (1H, s), 4.78 (2H, s), 7.36 (1H, d), 8.72 (1H, d), 9.18 (1H, s).

Preparation 28

3-Chloromethylpyridazihe hydrochloride

Thionyl chloride (3.05 ml, 42 mmol) was added to an ice-cooled flask containing the title compound of Preparation 26 (920 mg, 8 mmol) and the reaction mixture stirred for 45 minutes at room temperature, then evaporated under reduced pressure. The residue was azeotroped with toluene (40 ml) to furnish the crude title compound (1.4 g) as a brown solid, which was of sufficient purity for generating the free base required for use in subsequent alkylation, reactions. δ (DMSO$_{d6}$): 4.98 (2H, s), 7.80 (1H, m), 7.90 (1H, d), 8.19 (1H, s), 9.22 (1H, d).

Preparation 29

3-Ethyl-5-(2-n-propoxyphenyl)-2-(pyridazin-3-yl)methyl-2,6-dihydro-7H-pyrazolo[4,3-d]pyrimidin-7-one Obtained as a foam (28%) from the title compounds of Preparation 13 and Preparation 28 (free base), using the procedure of Preparation 15C. δ (CDCl$_3$): 1.13 (3H, t), 1.34 (3H, t), 2.00 (2H, m), 3.08 (2H, q), 4.18 (2H, t), 5.88 (2H, s), 7.04 (1H, d), 7.11 (1H, m), 7.46 (3H, m), 8.40 (1H, d), 9.15 (1H, d), 10.92 (1H, s). LRMS: m/z 391 (M+1)$^+$.

Preparation 30

5-(2-n-Propoxyphenyl)-3-n-propyl-2-(pyridazin-3-yl)methyl-2,6-dihydro-7H-pyrazolo[4,3-d]pyrimidin-7-one Obtained as a cream foam (25%) from the title compounds of Preparation 12 and Preparation 28 (free base), using the procedure of Preparation 15C. δ (CDCl$_3$): 0.93 (3H, t), 1.10 (3H, t), 1.73 (2H, m), 1.98 (2H, m), 2.99 (2H, t), 4.16 (2H, t), 5.84 (2H, s), 7.00 (1H, s), 7.08 (1H, m), 7.41 (3H, m), 8.38 (1H, d), 9.12 (1H, d), 10.90 (1H, s). LRMS: m/z 405 (M+1)$^+$.

Preparation 31

5-(2-n-Propoxyphenyl)-3-n-propyl-2-(pyridazin4-yl)methyl-2,6-dihydro-7H-pyrazolo[4,3-d]pyrimidin-7-one Obtained as a gum (13%) from the title compounds of Preparation 12 and Preparation 25, using the procedure of Preparation 15E. Found: C, 65.19; H, 5.99; N, 20.69. $C_{22}H_{24}N_6O_2$ requires C, 65.33; H, 5.98; N, 20.78%. δ (CDCl$_3$): 0.99 (3H, t), 1.13 (3H, t), 1.85 (2H, m), 1.98 (2H, m), 2.92 (2H, t), 4.15 (2H, t), 5.77 (2H, s), 7.02 (1H, d), 7.12 (1H, m), 7.35 (1H, d), 7.44 (1H, m), 8.48 (1H, d), 9.10 (1H, d), 9.16 (1H, s), 11.29 (1H, s). LRMS: m/z 405 (M+1)$^+$.

Preparation 32

5-(2-n-Propoxyphenyl)-3-n-propyl-2-(pyrimidin4-yl)methyl-2,6-dihydro-7H-pyrazolo[4,3-d]pyrimidin-7-one Obtained as a white solid (9%) from the title compounds of Preparation 12 and Preparation 27, using the procedure of Preparation 15E. δ (CDCl$_3$): 0.96 (3H, t), 1.12 (3H, t), 1.76 (2H, m), 2.00 (2H, m), 2.94 (2H, t), 4.16 (2H, t), 5.61 (2H, s), 6.98 (1H, d), 7.05 (1H, d), 7.10 (1H, m), 7.46 (1H, m), 8.40 (1H, d), 8.64 (1H, d), 9.18 (1H, s), 10.94 (1H, s). LRMS: m/z 405 (M+1)$^+$.

Preparation 33

2-[(2,4-Dichloropyrimidin-5-yl)methyl]-5-(2-n-propoxyphenyl)-3-n-propyl-2,6-dihydro-7H-pyrazolo[4,3]pyrimidin-7-one Obtained as a yellow foam (40%) from the title compound of Preparation 12 and 2,4-dichloro-5-chloromethylpyrimidine (Annalen, 1966, 692, 119), using the procedure of Preparation 15B. δ (CDCl$_3$): 0.97 (3H, t), 1.07 (3H, t), 1.80 (2H, m), 1.98 (2H, m), 2.95 (2H, t), 4.14 (2H, t), 5.57 (2H, s), 7.00 (1H, d), 7.10 (1H, m), 7.46 (1H, m), 8.13 (1H, s), 8.39 (1H, d), 10.95 (1H, s).

LRMS: m/z 474 (M+1)$^+$.

Preparation 34

5-(2-n-Propoxyphenyl)-3-n-propyl-2-(pyrimidin-5-yl)methyl-2,6-dihydro-7H-pyrazolo[4,3-d]pyrimidin-7-one The title compound of Preparation 33 (523 mg, 1.1 mmol) was added to a solution of triethylamine (3.0 ml, 21.5 mmol) in ethanol (25 ml), followed by 10% palladium on charcoal (150 mg), and the mixture hydrogenated for 1 hour at 276 kPa (40 psi) and room temperature, then filtered. The filtrate was combined with an ethanol wash (50 ml) of the filter pad and then evaporated under reduced pressure. The residue was suspended in water (15 ml) and the mixture extracted with ethyl acetate (50 ml), then the extract was dried (Na$_2$SO$_4$) and concentrated under reduced pressure. The residue was purified by column chromatography on silica gel, using dichloromethane:methanol (98:2) as eluant, to afford the title compound (243 mg) as a cream foam. δ (CDCl$_3$): 0.96 (3H, t), 1.06 (3H, t), 1.79 (2H, m), 1.99 (2H, m), 2.93 (2H, t), 4.13 (2H, t), 5.51 (2H, s), 7.01 (1H, d), 7.09 (1H, m), 7.43 (1H, m), 8.38 (1H, d), 8.63 (2H, s), 9.15 (1H, s), 10.91 (1H, s). LRMS: m/z 405 (M+1)$^+$.

Preparation 35

3-Ethyl-5-(2-n-propoxyphenyl)-2-(pyrazin-2-yl)methyl-2,6-dihydro-7H-pyrazolo[4,3-d]pyrimidin-7-one Obtained as a foam (46%) from the title compound of Preparation 13 and 2-chloromethylpyrazine (J. Org. Chem., 1973, 38, 2049), using the procedure of Preparation 15B. δ (CDCl$_3$): 1.08 (3H, t), 1.34 (3H, t), 1.96 (2H, t), 3.06 (2H, q), 4.14 (2H, t), 5.66 (2H, s), 7.00 (1H, d), 7.08 (1H, m), 7.42 (1H, m), 8.37 (1H, d), 8.46 (1H, s), 8.50 (2H, s), 10.84 (1H, s). LRMS: m/z 391 (M+1)$^+$.

Preparation 36

5-(2-n-Propoxyphenyl)-3-n-propyl-2-(pyrazin-2-yl)methyl-2,6-dihydro-7H-pyrazolo[4,3-d]pyrimidin-7-one Obtained as a cream foam (25%) from the title compound of Preparation 12 and 2-chloromethylpyrazine (J. Org. Chem., 1973, 38, 2049), using the procedure of Preparation 15B. δ (CDCl$_3$): 0.97 (3H, t), 1.08 (3H, t), 1.78 (2H, m), 1.98 (2H, m), 2.99 (2H, t), 4.16 (2H, t), 5.66 (2H, s), 7.01 (1H, d), 7.10 (1H, m), 7.41 (1H, m), 8.39 (1H, d), 8.44 (1H, s); 8.50 (2H, s), 10.85 (1H, s). LRMS: m/z 405 (M+1)$^+$.

Preparation 37

4-(2-Ethoxybenzamido)-3-methyl-1H-pyrazole-5-carboxamide

Obtained from 4-amino-3-methyl-1H-pyrazole-5-carboxamide (J. Org. Chem., 1956, 21, 833) and 2-ethoxybenzoyl chloride, by analogy with Preparation 9, as a white powder (83%). δ (DMSO$_{d6}$): 1.44 (3H, t), 2.28 (3H, s), 4.28 (2H, q), 7.06 (1H, m), 7.19 (2H, m), 7.48 (2H, m), 8.00 (1H, d), 10.46 (1H, s), 12.88 (1H, s). LRMS: m/z 289 (M+1)$^+$.

Preparation 38

4-(2-Methoxybenzamido)-3-n-propyl-1H-pyrazole-5-carboxamide

Obtained from the title compound of Preparation 7 and 2-methoxybenzoyl chloride, by analogy with Preparation 9, as a white powder (55%). δ (DMSO$_{d6}$): 0.84 (3H, t), 1.55 (2H, m), 2.79 (2H, t), 4.00 (3H, s), 7.08 (1H, m), 7.20 (1H, d), 7.28 (1H, s), 7.44 (1H, s), 7.54 (1H, m), 10.62 (1H, s). LRMS: m/z 303 (M+1)$^+$.

Preparation 39

5-(2-Ethoxyphenyl)-3-methyl-1,6-dihydro-7H-pyrazolo[4,3-d]pyrimidin-7-one

Obtained from the title compound of Preparation 37, by analogy with Preparation 12, as a white solid (92%). δ (DMSO$_{d6}$): 1.30 (3H, t), 2.40 (3H, s), 4.12 (2H, q), 7.05 (1H, m), 7.14 (1H, d), 7.46 (1H, m), 7.68 (1H, d), 11.90 (1H, s), 13.68 (1H, s). LRMS: m/z 271 (M+1)$^+$.

Preparation 40

5-(2-Methoxyphenyl)-3-n-propyl-1,6-dihydro-7H-pyrazolo[4,3-d]pyrimidin-7-one

Obtained from the title compound of Preparation 38, by analogy with Preparation 12, as a white solid (71%). δ (DMSO$_{d6}$): 0.92 (3H, t), 1.76 (2H, m), 2.80 (2H, t), 3.85 (3H, s), 7.08 (1H, m), 7.17 (1H, d), 7.49 (1H, m), 7.64 (1H, d), 11.47–11.94 (1H, br), 13.69–13.94 (1H, br). LRMS: m/z 285 (M+1)$^+$.

Preparation 41

5-(2-Methoxyphenyl)-3-n-propyl-1-(pyridin-2-yl) methyl-1,6-dihydro-7H-pyrazolo[4,3-d]pyrimidin-7-one Obtained as a white crystalline solid (38%) from the title compound of Preparation 40 and 2-chloromethylpyridine, using the procedure of Preparation 15D. Found: C, 67.00; H, 5.60; N, 18.49. C$_{21}$H$_{21}$N$_5$O$_2$ requires C,67.18; H, 5.64; N,18.65%. δ (CDCl$_3$): 1.01 (3H, t), 1.90 (2H, m), 2.98 (2H, t), 4.03 (3H, s), 5.96 (2H, s), 6.99 (1H, d), 7.05 (1H, d), 7.16 (2H, m), 7.47 (1H, m), 7.59 (1H, m), 8.48 (1H, d), 8.58 (1H, d), 10.88 (1H, s).

Preparation 42

5-(2-Ethoxyphenyl)-3-methyl-2-(pyridin-2-yl) methyl-2,6-dihydro-7H-pyrazolo[4,3-d]pyrimidin-7-one Obtained as a white foam (21%) from the title compound of Preparation 39 and 2-chloromethylpyridine, using the procedure of Preparation 15B. Found: C, 65.30; H, 5.08; N, 18.79. C$_{20}$H$_{19}$N$_5$O$_2$; 0.30 H$_2$O requires C, 65.49; H, 5.39; N, 19.09%. δ (CDCl$_3$): 1.59 (3H, t), 2.57 (3H, s), 4.28 (2H, q), 5.66 (2H, s), 7.08 (3H, m), 7.20 (1H, m), 7.44 (1H, m), 7.62 (1H, m), 8.42 (1H, d), 8.59 (1H, d), 10.88 (1H, s). LRMS: m/z 362 (M+1)$^+$.

Preparation 43

5-(2-Methoxyphenyl-3-n-propyl-2-(pyridin-2-yl) methyl-2,6-dihydro-7H-pyrazolo[4,3-d]pyrimidin-7-one Obtained as a white crystalline solid (29%) from the title compound of Preparation 40 and 2-chloromethylpyridine, using the procedure of Preparation 15B. Found: C, 66.93; H, 5.61; N, 18.61. C$_{21}$H$_{21}$N$_5$O$_2$ requires C,67.18; H, 5.64; N,18.65%. δ (CDCl$_3$): 0.96 (3H, t), 1.76(2H, m), 2.98 (2H, t), 4.03 (3H, s), 5.68 (2H, s), 7.05 (2H, 2 xd), 7.16 (1H, m), 7.21 (1H, m), 7.46 (1H, m), 7.62 (1H, m), 8.41 (1H, d), 8.58 (1H, d), 10.78 (1H, s). LRMS: m/z 376 (M+1 )$^+$.

Preparation 44

5-[5-(4-t-Butoxycarbonylpiperazin-1-ylsulphonyl)-2-n-propoxyphenyl]-3-n-propyl-2-(pyridin-2-yl) methyl-2,6-dihydro-7H-pyrazolo[4,3-d]pyrimidin-7-one Obtained as a solid (60%) from the title compound of Preparation 20 and 1-t-butoxycarbonylpiperazine, using the procedure of Example 1. δ (CDCl$_3$): 0.96 (3H, t), 1.15 (3H, t), 1.40 (9H, s), 1.76 (2H, m), 2.04 (2H, m), 2.98 (2H, t), 3.03 (4H, m), 3.52 (4H, m), 4.26 (2H, t), 5.70 (2H, s), 7.06 (1H, m), 7.16 (1H, d), 7.21 (1H, m), 7.62 (1H, m), 7.82 (1H, d), 8.58 (1H, d), 8.78 (1H, s), 10.60 (1H, s). LRMS: m/z 652 (M+1)$^+$.

Preparation 45

3-Methoxy-2-methylpyridine

A stirred solution of 3-hydroxy-2-methylpyridine (1.0 g, 9.2 mmol), phenyltrimethylammonium bromide (2.2 g, 11 mmol) and sodium methoxide (550 mg, 11 mmol) in dimethylformamide (10 ml) was heated under reflux for 3 hours, then the cool reaction mixture washed with water (40 ml) and extracted with ether (3×40 ml). The combined extracts were dried (Na$_2$SO$_4$) and evaporated under reduced pressure, then the residue purified by column chromatography on silica gel, using hexane:ethyl acetate (1:1) as eluant, to give the title compound (190 mg) as a solid. δ (CDCl$_3$): 2.34 (3H, s), 3.68 (3H, s), 6.93 (2H, m), 7.94 (1H, d). LRMS: m/z 124 (M+1)$^+$.

Preparation 46

2-Chloromethyl-3-methoxypyridine

The title compound of Preparation 45 (190 mg, 1.5 mmol) was added to a stirred solution of benzamide (5 mg, 0.4 mmol) in dichloromethane (2 ml) and the mixture heated to reflux temperature. Trichloroisocyanuric acid (190 mg, 0.82 mmol) was added portionwise, then the reaction mixture stirred under reflux for 3 hours, allowed to cool and treated with water (2 ml) and 50% aqueous potassium hydroxide solution (3 ml). The separated aqueous phase was washed with dichloromethane (3×10 ml) and the combined organic solutions dried (Na$_2$SO$_4$) and evaporated under reduced pressure to yield the title compound (180 mg) as a colourless oil. δ (CDCl₃): 3.91 (3H, s), 4.76 (2H, s), 7.25 (2H, m), 8.20 (1H, d). LRMS: m/z 158 (M+1)⁺.

Preparation 47

1-(3-Methoxypyridin-2-yl)methyl-5-(2-n-propoxyphenyl)-3-n-propyl-1,6-dihydro-7H-pyrazolo[4,3-d]pyrimidin-7-one Obtained as a white solid (4%) from the title compounds of Preparation 12 and Preparation 46, using the procedure of Preparation 15B. δ (CDCl₃): 0.98 (3H, t), 1.12 (3H, t), 1.83 (2H, m), 1.97 (2H, m), 2.92 (2H, t), 3.80 (3H, s), 4.16 (2H, t), 5.96 (2H, s), 7.00 (1H, d), 7.10 (3H, m), 7.41 (1H, m), 8.01 (1H, d), 8.48 (1H, d), 11.08 (1H, s). LRMS : m/z 434 (M+1)⁺.

Preparation 48

2-(3-Methoxypyridin-2-yl)methyl-5-(2-n-propoxyphenyl)-3-n-propyl-2,6-dihydro-7H-pyrazolo[4,3-d]pyrimidin-7-one Obtained as a white solid (78%) from the title compounds of Preparation 12 and Preparation 46, using the procedure of Preparation 15B. δ (CDCl₃): 0.98 (3H, t), 1.06 (3H, t), 1.78 (2H, m), 1.95 (2H, m), 2.97 (2H, t), 3.83 (3H, s), 4.12 (2H, t), 5.66 (2H, s), 6.99 (1H, d), 7.06 (1H, m), 7.18 (2H, m), 7.39 (1H, m), 8.06 (1H, d), 8.38 (1H, d), 10.70 (1H, s). LRMS: m/z 434 (M+1)⁺.

Preparation 49

2-(6-Pivaloylaminopyridin-2-yl)methyl-5-(2-n-propoxyphenyl)-3-n-propyl-2,6-dihydro-7H-pyrazolo[4,3-d]pyrimidin-7-one Obtained as a white solid (78%) from the title compound of Preparation 12 and 2-bromomethyl-6-pivaloylaminopyridine (Chem. Lett., 1995, 61), using the procedure of Preparation 15B. δ (CDCl₃): 0.99 (3H, t), 1.12 (3H, t), 1.36 (9H, s), 1.79 (2H, m), 2.00 (2H, m), 2.95 (2H, t), 4.18 (2H, t), 5.55 (2H, s), 6.60 (1H, d), 7.04 (1H, d), 7.12 (1H, m), 7.43 (1H, m), 7.61 (1H, m), 7.96 (1H, s), 8.16 (1H, d), 8.40 (1H, d), 10.90 (1H, s). LRMS: m/z 503 (M+1)⁺.

Preparation 50

1-(6-Pivaloylaminopyridin-2-yl)methyl-5-(2-n-propoxyphenyl)-3-n-propyl-1,6-dihydro-7H-pyrazolo[4,3-d]pyrimidin-7-one Obtained as a white solid (12%) from the title compound of Preparation 12 and 2-bromomethyl-6-pivaloylaminopyridine (Chem. Lett., 1995, 61), using the procedure of Preparation 15B. δ (CDCl₃): 1.00 (3H, t), 1.16 (3H, t), 1.32 (9H, s), 1.90 (2H, m), 2.00 (2H, m), 2.98 (2H, t), 4.17 (2H, t), 5.80 (2H, s), 6.70 (1H, d), 7.05 (1H, d), 7.14 (1H, m), 7.46 (1H, m), 7.59 (1H, m), 7.99 (1H, s), 8.12 (1H, s), 8.52 (1H, d), 11.22 (1H, s). LRMS: m/z 503 (M+1)⁺.

Preparation 51

1-(1-Methylimidazol-2-yl)methyl-5-(2-n-propoxyphenyl)-3-n-propyl-1,6-dihydro-7H-pyrazolo[4,3-d]pyrimidin-7-one Obtained as a white solid (21%) from the title compound of Preparation 12 and the free base of 2-chloromethyl-1-methylimidazole hydrochloride (J. Chem. Soc., 1957, 3305), using the procedure of Preparation 15B. δ (CDCl3): 1.00 (3H, t), 1.18 (3H, t) 1.86 (2H, m), 2.02 (2H, m), 2.92 (2H, t), 3.70 (3H, s), 4.19 (2H, t), 6.04 (2H, s), 6.82 (1H, s), 7.05 (1H, d), 7.16 (1H, m), 7.46 (1H, m), 8.50 (1H, d), 11.26 (1H, s). LRMS: m/z 407 (M+1)⁺.

Preparation 52

2-(1-Methylimidazol-2-yl)methyl-5-(2-n-propoxyphenyl)-3-n-propyl-2,6-dihydro-7H-pyrazolo[4,3-d]pyrimidin-7-one Obtained as a white solid (18%) from the title compound of Preparation 12 and the free base of 2-chloromethyl-1-methylimidazole hydrochloride (J. Chem. Soc., 1957, 3305), using the procedure of Preparation 15B. δ (CDCl₃): 0.98 (3H, t), 1.14 (3H, t), 1.75 (2H, m), 1.99 (2H, m), 3.12 (2H, t), 3.76 (3H, s), 4.18 (2H, t), 5.67 (2H, s), 6.84 (1H, s), 7.02 (1H, d), 7.13 (1H, m), 7.44 (1H, m), 8.38 (1H, d), 10.87 (1H, s). LRMS: m/z407 (M+1)⁺.

Preparation 53

1-(3,5-Dimethylimidazol-4-yl)methyl-5-(2-n-propoxyphenyl)-3-n-propyl-1,6-dihydro-7H-pyrazolo[4,3-d]pyrimidin-7-one Obtained as a white solid (44%) from the title compound of Preparation 12 and 4-chloromethyl-3,5-dimethylisoxazole using the procedure of Preparation 15D. Found: C, 65.40; H, 6.47; N, 16.53. $C_{23}H_{27}N_5O_3$ requires C, 65.54; H, 6.49; N, 16.62%. δ (CDCl₃): 1.02 (3H, t), 1.17 (3H, t), 1.86 (2H, m), 2.02 (2H, m), 2.35 (3H, s), 2.52 (3H, s), 2.92 (2H, t), 4.19 (2H, t), 5.56 (2H, s), 7.05 (1H, d), 7.16 (1H, m), 7.46 (1H, m), 8.50 (1H, d), 11.16 (1H, s). LRMS: m/z 422 (M+1)⁺.

Preparation 54

5-(2-Ethoxyphenyl)-3-methyl-1-(3,5-dimethylisoxazol-4-yl)methyl-1,6-dihydro-7H-pyrazolo[4,3-d]pyrimidin-7-one Obtained as a white solid (72%) from the title compound of Preparation 39 and 4-chloromethyl-3,5-dimethylisoxazole, using the procedure of Preparation 15A. Found: C, 63.19; H, 5.55; N, 18.30. *$C_{20}H_{21}N_5O_3$ requires C, 63.31; H, 5.58; N, 18.46%. δ (CDCl₃): 1.64 (3H, t), 2.34 (3H, s), 2.52 (6H, 2 ×s), 4.32 (2H, q), 5.54 (2H, s), 7.06 (1H, d), 7.15 (1H, m), 7.46 (1H, m), 8.51 (1H, d), 11.18 (1H, s). LRMS: m/z 380 (M+1)⁺.

Preparation 55

2-(3,5-Dimethylisoxazol4-yl)methyl-5-(2-n-propoxyphenyl)-3-n-propyl-2,6-dihydro-7H-pyrazolo[4,3-d]pyrimidin-7-one Obtained as a white solid (16%) from the title compound of Preparation 12 and 4-chloromethyl-3,5-dimethylisoxazole, using the procedure of Preparation 15D. Found: C, 64.88; H, 6.41; N. 16.33. $C_{23}H_{27}N_5O_3$ requires C, 65.54; H, 6.49; N, 16.62%. δ (CDCl₃): 1.00 (3H, t), 1.14 (3H, t), 1.78 (2H, m), 1.98 (2H, m), 2.17 (3H, s), 2.36 (3H, s), 2.90 (2H, t), 4.18 (2H, t), 5.28 (2H, s), 7.02 (1H, d), 7.12 (1H, m), 7.43 (1H, m), 8.38 (1H, d), 10.90 (1H, s). LRMS: m/z 422 (M+1)⁺.

Preparation 56

1-(2-Methylthiazol-4-yl)methyl-5-(2-n-propoxyphenyl)-3-n-propyl-1,6-dihydro-7H-pyrazolo[4,3-d]pyrimidin-7-one Obtained as a white powder (30%) from the title compound of Preparation 12 and the free base of 4-chloromethyl-2-methylthiazole hydrochloride, using the procedure of Preparation 15D. Found: C, 61.32; H, 5.86; N, 16.08. $C_{22}H_{25}N_5O_2S$; 0.40 $H_2O$ requires C, 61.35; H, 6.04; N, 16.26%. δ ($CDCl_3$: 1.03 (3H, t), 1.18 (3H, t), 1.90 (2H, m), 2.01 (2H, m), 2.67 (3H, s), 2.98 (2H, t), 4.20 (2H, t), 5.90 (2H, s), 6.88 (1H, s), 7.05 (1H, d), 7.16 (1H, m), 7.46 (1H, m), 8.52 (1H, d), 11.20 (1H, s). LRMS: m/z 424 $(M+1)^+$.

Preparation 57

5-(2-Ethoxyphenyl)-3-methyl-2-(2-methylthiazol-4-yl)methyl-2,6-dihydro-7H-pyrazolo[4,3-d]pyrimidin-7-one Obtained as a white solid (22%) from the title compound of Preparation 39 and the free base of 4-chloromethyl-2-methylthiazole hydrochloride, using the procedure of Preparation 15B. Found: C,59.47; H, 4.95; N, 18.10. $C_{19}H_{19}N_5O_2S$ requires C, 59.83; H, 5.02; N, 18.36%. δ ($CDCl_3$): 1.58 (3H,t), 2.65 (3H, s), 2.69 (3H, s), 4.28 (2H, q), 5.60 (2H, s), 6.90 (1H, s), 7.04 (1H, d), 7.13 (1H, m), 7.44 (1H, m), 8.42 (1H, d), 10.85 (1H, s). LRMS: m/z 382 $(M+1)^+$.

Preparation 58

2-(2-Methylthiazol-4-yl)methyl-5-(2-n-propoxyphenyl)-3-n-propyl-2,6-dihydro-7H-pyrazolo[4,3-d]pyrimidin-7-one Obtained as a white powder (10%) from the title compound of Preparation 12 and the free base of 4-chloromethyl-2-methylthiazole hydrochloride, using the procedure of Preparation 15D. Found: C, 61.90; H, 6.04; N, 15.95. $C_{22}H_{25}N_5O_2S$; 0.20 $H_2O$ requires C, 61.86; H, 5.99; N, 16.40%. δ ($CDCl_3$): 1.00 (3H, t), 1.14 (3H, t), 1.80 (2H, m), 2.00 (2H, m), 2.70 (3H, s), 3.04 (2H, t), 4.18 (2H, t), 5.63 (2H, s), 6.86 (1H, s), 7.05 (1H, d), 7.14 (1H, m), 7.44 (1H, m), 8.40 (1H, d), 10.85 (1H, s). LRMS: m/z 424 $(M+1)^+$.

Preparation 59

1-(1-Methyl-1,2,4-triazol-5-yl)methyl-5-(2-n-propoxyphenyl)-3-n-propyl-1,6-dihydro-7H-pyrazolo[4,3-d]pyrimidin-7-one Obtained as a white solid (31%) from the title compound of Preparation 12 and the free base of 5-chloromethyl-1-methyl-1,2,4-triazole hydrochloride (J. Antibiotics, 1993, 46, 1866), using the procedure of Preparation 15B. δ ($CDCl_3$): 1.00 (3H, t), 1.18 (3H, t), 1.86 (2H, m), 2.02 (2H, m), 2.94 (2H, t), 3.98 (3H, s), 4.20 (2H, t), 5.97 (2H, s), 7.06 (1H, d), 7.16 (1H, m), 7.46 (1H, m), 7.83 (1H, s), 8.50 (1H, d), 11.27 (1H, s). LRMS: m/z 408 $(M+1)^+$.

Preparation 60

2-(1-Methyl-1,2,4-triazol-5-yl)methyl-5-(2-n-propoxyphenyl)-3-n-propyl-2,6-dihydro-7H-pyrazolo[4,3-d]pyrimidin-7-one Obtained as a colourless foam (25%) from the title compound of Preparation 12 and the free base of 5-chloromethyl-1-methyl-1,2,4-triazole hydrochloride (J. Antibiotics, 1993, 46, 1866), using the procedure of Preparation 15B. δ ($CDCl_3$): 1.00 (3H, t), 1.14 (3H, t), 1.80 (2H, m), 1.99 (2H, m), 3.09 (2H, t), 4.00 (3H, s), 4.18 (2H, t), 5.72 (2H, s), 7.04 (1H, d), 7.14 (1H, m), 7.45 (1H, m), 7.84 (1H, s), 8.39 (1H, d), 10.94 (1H, s): LRMS: m/z 408 $(M+1)^+$.

Preparation 61

1-(2-Methoxyethyl)-1,2,4-triazole

2-Bromoethyl methyl ether (6.7 ml, 0.072 mol) was added to a stirred, ice-cooled suspension of 1,2,4-triazole (5.0 g, 0.072 mol) and potassium carbonate (10 g, 0.072 mol) in acetone (50 ml). After a further 3 hours the cooling bath was removed and stirring continued for 18 hours at room temperature. The reaction mixture was filtered, the filtrate evaporated under reduced pressure and the residue purified by column chromatography on silica gel, using dichloromethane:methanol (95:5) as eluant, to provide the title compound (5.2 g) as a clear oil. δ ($CDCl_3$): 3.32 (3H, s), 3.74 (2H, t), 4.34 (2H, t), 7.92 (1H, s), 8.14 (1H, s). LRMS: m/z 128 $(M+1)^+$.

Preparation 62

5-Hydroxymethyl-1-(2-methoxyethyl)-1,2,4-triazole

A solution of the title compound of Preparation 61 (4.3 g, 0.034 mol) in 40% aqueous formaldehyde solution (5 ml, 0.098 mol) was heated at 140° C. for 18 hours in a sealed vessel. The cool reaction mixture was evaporated under reduced pressure and the residue purified by column chromatography on silica gel, using dichloromethane:methanol (97:3) as eluant, to produce the title compound (87%) as an oil. δ ($CDCl_3$): 3.30 (3H, s), 3.76 (2H, t), 4.08 (1H, s), 4.41 (2H, t), 4.78 (2H, s), 7.85 (1H, s). m/z 158 $(M+1)^+$.

Preparation 63

5-Chloromethyl-1-(2-methoxyethyl)-1,2,4-triazole hydrochloride

The title compound of Preparation 62 (3.5 g, 0.022 mol) was added dropwise to stirred, ice-cooled thionyl chloride (10 ml), then the cooling bath removed. The reaction mixture was stirred at room temperature for 5 hours and then evaporated under reduced pressure. Azeotropy of the residue with toluene (50 ml) furnished the title compound (4.6g) as a yellow oil. δ ($CDCl_3$): 3.32 (3H, s), 3:79 (2H, t), 4.59 (2H, t), 5.15 (2H, s), 8.40 (1H, s), 10.09 (1H, s).

Preparation 64

1-[1-(2-Methoxyethyl)-1,2,4-triazol-5-yl]methyl-5-(2-n-propoxyphenyl)- 3-n-propyl-1,6-dihydro-7H-pyrazolo[4,3-d]pyrimidin-7-one Obtained as a white solid (30%) from the title compound of Preparation 12 and the free base of the title compound of Preparation 63, using the procedure of Preparation 15B. δ ($CDCl_3$): 1.00 (3H, t), 1.16 (3H, t), 1.86 (2H, m), 2.00 (2H, m), 2.84 (2H, t), 3.26 (3H, s), 3.70 (2H, t), 4.19 (2H, t), 4.56 (2H, t), 6.00 (2H, s), 7.04 (1H, d), 7.15 (1H, m), 7.45 (1H, m), 7.84 (1H, s), 8.48 (1H, d), 11.20 (1H, s). LRMS: m/z 452 $(M+1)^+$.

Preparation 65

2-[1-(2-Methoxyethyl)-1,2,4-triazol-5-yl]methyl-5-(2-n-propoxyphenyl)-3-n-propyl-2,6-dihydro-7H-pyrazolo[4,3-d]pyrimidin-7-one Obtained as a white solid (20%) from the title compound of Preparation 12 and the free base of the title compound of Preparation 63, using the procedure of Preparation 15B. δ ($CDCl_3$): 1.03 (3H, t), 1.13 (3H, t), 1.83 (2H, m), 1.99 (2H, m), 3.12 (2H, t), 3.30 (3H, s), 3.70 (2H, t), 4.18 (2H, t), 4.61 (2H, t), 5.78 (2H, s), 7.04 (1H, d), 7.14 (1H, m), 7.44 (1H, m), 7.86 (1H, s), 8.39 (1H, d), 10.87 (1H, s). LRMS: m/z 452 $(M+1)^+$.

Preparation 66

1-(4-Methyl-1,2,4-triazol-3-yl)methyl-5-(2-n-propoxyphenyl)-3n-propyl-1,6-dihydro-7H-pyrazolo[4,3-d]pyrimidin-7-one Obtained as a white solid (34%) from the title compound of Preparation 12 and the free base of 3-chloromethyl-4- methyl-1,2,4-triazole hydrochloride (Chem. Pharm. Bull., 1994, 42, 85), using the procedure of Preparation 15B. δ (CDCl$_3$): 1.00 (3H, t), 1.18 (3H, t), 1.85 (2H, m), 2.03 (2H, m), 2.92 (2H, t), 3.73 (3H, s), 4.20 (2H, t), 6.05 (2H, s), 7.06 (1H, d), 7.16 (1H, m), 7.48 (1H, m), 8.10 (1H, s), 8.50 (1H, d), 11.28 (1H, s). LRMS: m/z. 408 (M+1)$^+$.

Preparation 67

1-( 1,2,4-Oxadiazol-3-yl)methyl-5-(2-n-propoxyphenyl)-3-n-propyl-1,6-dihydro-7H-pyrazolo[4,3-d]pyrimidin-7-one Obtained as an off-white solid (24%) from the title compound of Preparation 12 and 3-chloromethyl-1,2,4-oxadiazole, using the procedure of Preparation 15D. δ (CDCl$_3$): 1.02 (3H, t), 1.18 (3H, t), 1.88 (2H, m), 2.00 (2H, m), 2.97 (2H, t), 4.19 (2H, t), 6.02 (2H, s), 7.04 (1H, d), 7.16 (1H, m), 7.46 (1H, m), 8.52 (1H, d), 8.66 (1H, s), 11.28 (1H, s). LRMS: m/z 395 (M+1)$^+$.

Preparation 68

2-Benzyloxycarbonylmethyl-5-(2-n-propoxyphenyl)-3-n-propyl-2,6-dihydro-7H-pyrazolo[4,3-d]pyrimidin-7-one Obtained as a yellow solid (45%) from the title compound of Preparation 12 and benzyl bromoacetate, using the procedure of Preparation 15B. δ (CDCl$_3$): 1.00 (3H, t), 1.14 (3H, t), 1.81 (2H, m), 2.00 (2H, m), 2.89 (2H, t), 4.18 (2H, t), 5.17 (2H, s), 5.23 (2H, s), 7.06 (1H, d), 7.13 (1H, m), 7.36 (5H, m), 7.46 (1H, m), 8.41 (1H, d), 10.87 (1H, s).

Preparation 69

2-Carboxymethyl-5-(2-n-propoxyphenyl)-3-n-propyl-2,6-dihydro-7H-pyrazolo[4,3-d]pyrimidin-7-one 10% Palladium on charcoal (20 mg) was added to a solution of the title compound of Preparation 68 (207 mg, 0.45 mmol) in ethyl acetate (25 ml) and the mixture stirred under hydrogen at 138 kPa (20 psi) for 20 hours and then filtered. Evaporation under reduced pressure of the filtrate afforded the title compound (95%) as a yellow powder. δ (DMSO$_{d6}$): 0.93 (6H, m), 1.71 (4H, m), 2.84 (2H, t), 4.03 (2H, t), 5.21 (2H, s), 7.09 (1H, m), 7.16 (1H, d), 7.48 (1H, m), 7.69 (1H, d), 11.52 (1H, s). LRMS: m/z 371 (M+1)$^+$.

Preparation 70

N-t-Butoxycarbonyl-N'-{2-[5-(2-n-propoxyphenyl)-3-n-propyl-2,6-dihydro-7H-pyrazolo[4,3-d]pyrimidin-7-on-2-yl]acetyl}hydrazine Oxalyl chloride (0.33 ml, 3.8 mmol) was added dropwise to a stirred, ice-cooled suspension of the title compound of Preparation 69 (0.70 g, 1.9 mmol) in dichloromethane (7 ml), followed by dimethylformamide (2 drops), the cooling bath removed and the reaction mixture stirred at room temperature for 2 hours, then evaporated under reduced pressure. Azeotropy of the residue with dichloromethane (30 ml) gave the required acyl chloride as a yellow solid.

This intermediate was added to a stirred solution of t-butyl carbazate (0.25 g, 1.9 mmol) and triethylamine (0.40 ml, 2.8 mmol) in dichloromethane (10 ml) and the mixture stirred at room temperature for 2 hours, then washed with 5% aqueous citric acid solution (20 ml). The aqueous washing was extracted with dichloromethane (50 ml) and the combined organic solutions dried (MgSO$_4$) and evaporated under reduced pressure. Purification of the residue by column chromatography, using an elution gradient of hexane:ethyl acetate (1:1 to 1:2), provided the title compound (0.29 g) as an orange solid. δ (CDCl$_3$): 1.06 (3H, t) 1.15 (3H, t), 1.44 (9H, s), 1.88 (2H, m), 2.00 (2H, m), 3.02 (2H, t), 4.17 (2H, t), 5.20 (2H, s), 6.59 (1H, s), 7.04 (1H, d), 7.12 (1H, m), 7.44 (1H, m), 8.40 (1H, d), 8.72 (1H, s), 10.96 (1H, s). LRMS: m/z 485 (M+1)$^+$.

Preparation 71

N-{2-[5-(2-n-Propoxyphenyl)-3-n-propyl-2,6-dihydro-7H-pyrazolo-[4,3-d]pyrimidin-7-on-2-yl]acetyl}hydrazine hydrochloride A stirred, ice-cooled solution of the title compound of Preparation 70 (0.28 g, 0.58 mmol) in dichloromethane (5 ml) was saturated with hydrogen chloride and the cooling bath then removed. The reaction mixture was stirred at room temperature for 2 hours, then evaporated under reduced pressure to yield the title compound (0.22 g) as a yellow solid. δ (DMSO$_{d6}$): 0.95 (6H, m), 1.72 (4H, m), 2.89 (2H, t), 4.02 (2H, t), 5.28 (2H, s), 7.06 (1H, m), 7.16 (1H, d), 7.48 (1H, m), 7.68 (1H, d), 11.58 (2H, s). LRMS: m/z 385 (M+1)$^+$.

Preparation 72

2-(3-Methyl-1,2,4-triazol-5-yl)methyl-5-(2-n-propoxyphenyl)-3-n-propyl-2,6-dihydro-7H-pyrazolo[4,3-d]pyrimidin-7-one A solution of sodium methoxide (62 mg, 1.16 mmol) in ethanol (2 ml) was added to a stirred solution of acetamidine hydrochloride (82 mg, 0.87 mmol) in ethanol and the mixture stirred at room temperature for 45 minutes.

Next, sodium methoxide (30 mg, 0.58 mmol) was added to a stirred suspension of the title compound of Preparation 71 (220 mg, 0.58 mmol) in ethanol (4 ml) and this mixture added to the previously prepared ethanolic solution of acetamidine. The reaction mixture was stirred under reflux for 72 hours, allowed to cool and diluted with water (15 ml), then the resulting mixture extracted with ethyl acetate (40 ml in total) and the combined organic solutions dried (MgSO$_4$) and evaporated under reduced pressure. The resulting yellow oil was purified by column chromatography on silica gel, using an elution gradient of ether:methanol (97:3 to 90:10), to produce the title compound (120 mg) as a white solid. δ (CDCl$_3$): 1.02 (3H, t), 1.12 (3H, t), 1.85 (2H, m), 1.99 (2H, m), 2.41 (3H, s), 3.07 (2H, t), 4.16 (2H, t), 5.60 (2H, s) 7.02 (1H, d), 7.10 (1H, m), 7.42 (1H, m), 8.39 (1H, d), 10.93 (1H, s). LRMS: m/z 408 (M+1)$^+$.

Preparation 73

2-Cyanomethyl-5-(2-n-propoxyphenyl)-3-n-propyl-2,6-dihydro-7H-pyrazolo[4,3-d]pyrimidin-7-one A 2M solution of sodium bis(trimethylsilyl)amide in tetrahydrofuran (4.42 ml, 8.8 mmol) was added to a stirred, ice-cooled solution of the title compound of Preparation 12 (2.3 g, 7.4 mmol) in tetrahydrofuran (25 ml) and the resulting solution stirred for 30 minutes, before being cooled to about 70° C. Bromoacetonitrile (0.54 ml, 7.7 mmol) was added dropwise, the cooling bath removed and, after a further 20 hours, the reaction mixture carefully quenched with methanol (5 ml) and evaporated under reduced pressure. The residue was purified by column chromatography on silica gel, using an elution gradient of dichloromethane:methanol (99:1 to 95:5), followed by crystallisation from hexane:ethyl acetate, to afford the title compound (1.89 g) as a white solid. Found: C, 64.84; H, 5.98; N, 19.71. $C_{19}H_{21}N_5O_2$ requires C, 64.94; H, 6.02; N, 19.93%. δ ($CDCl_3$): 1.12 (6H, m), 1.98 (4H, m), 3.08 (2H, t), 4.20 (2H, t), 5.26 (2H, s), 7.05 (1H, d), 7.16 (1H, m), 7.48 (1H, m), 8.42 (1H, d), 11.00 (1H, s). LRMS: m/z 703 (2M+1)$^+$.

Preparation 74

2-[5-(2-n-Propoxyphenyl)-3-n-propyl-2,6-dihydro-7H-pyrazolo-[4,3-d]pyrimidin-7-on-2-yl]acetamidoxime Sodium carbonate (199 mg, 1.9 mmol) and hydroxylamine hydrochloride (260 mg, 3.7 mmol) were added to a stirred suspension of the title compound of Preparation 73 (878 mg, 2.5 mmol) in 50% aqueous ethanol (10 ml) and the mixture heated under reflux for 18 hours, then allowed to cool. The resulting precipitate was collected, washed with water (30 ml) and dried under vacuum to afford the title compound (902 mg) as a white solid. Found: C, 59.23; H, 6.26; N, 21.51. $C_{19}H_{24}N_6O_3$ requires C, 59.36; H, 6.29; N, 21.86%. δ ($DMSO_{d6}$): 0.94 (6H, m), 1.63 (4H, m), 2.92 (2H, t) 4.04 (2H, t), 4.94 (2H, s), 5.48 (2H, s), 7.06 (1H, m), 7.17 (1H, d), 7.46 (1H, m), 7.68 (1H, d), 9.93 (1H, s), 11.49 (1H, s). LRMS: m/z 385 (M+1)$^+$.

Preparation 75

O-Acetyl-2-[5-(2-n-propoxyphenyl)-3-n-propyl-2,6-dihydro-7H-pyrazolo-[4,3-d]pyrimidin-7-on-2-yl]acetamidoxime Acetic anhydride (336 μl, 3.38 mmol) was added to a solution of the title compound of Preparation 74 (684 mg, 1.69 mmol) in tetrahydrofuran (5 ml) and the mixture stirred under reflux for 3 hours, then allowed to cool. The resulting precipitate was collected, washed with ether (20 ml) and dried under vacuum to yield the title compound (650 mg) as a white solid. Found: C, 59.02; H, 6.09; N, 19.58. $C_{21}H_{26}N_6O_4$ requires C, 59.14; H, 6.15; N, 19.71%. δ ($DMSO_{d6}$): 0.95 (6H, m), 1.66 (4H, m), 2.03 (3H, s), 2.95 (2H, t), 4.04 (2H, t), 5.05 (2H, s), 6.59 (2H, s), 7.06 (1H, m), 7.16 (1H, d), 7.47 (1H, m), 7.68 (1H, d), 11.52 (1H, s). LRMS: m/z 427 (M+1)$^+$.

Preparation 76

2-(5-Methyl-1,2,4-oxadiazol-3-yl)methyl-5-(2-n-propoxyphenyl)-3-n-propyl-2,6-dihydro-7H-pyrazolo[4,3-d]pyrimidin-7-one A solution of the title compound of Preparation 75 (630 mg, 1.50 mmol) in diglyme (5 ml) was stirred under reflux for 5 hours, allowed to cool and evaporated under reduced pressure. The residue was purified by column chromatography on silica gel, using hexane:ethyl acetate (34:66) as eluant, to give the title compound (520 mg) as a solid. Found: C, 61.40; H, 5.86; N, 20.28. $C_{21}H_{24}N_6O_3$ requires C, 61.75; H, 5.92; N, 20.57%. δ ($DMSO_{d6}$): 0.95 (6H, m), 1.74 (4H, m), 2.58 (3H, s), 2.98 (2H, t), 4.03 (2H, t), 5.76 (2H, s), 7.06 (1H, m), 7.16 (1H, d), 7.45 (1H, m), 7.66 (1H, d), 11.55 (1H, s). LRMS: m/z 409 (M+1)$^+$.

Preparation 77

2-Cyanomethyl-5-(2-ethoxyphenyl)-3-n-propyl-2,6-dihydro-7H-pyrazolo[4,3-d]pyrimidin-7-one Obtained as a solid (73%) from the title compound of Preparation 14 and bromoacetonitrile, using the procedure of Preparation 73. δ ($CDCl_3$): 1.10 (3H, t), 1.60 (3H, t), 1.95 (2H, m), 3.08 (2H, t), 4.31 (2H, q); 5.28 (2H, s), 7.07 (1H, d), 7.14 (1H, m), 7.48 (1H, m), 8.42 (1H, d), 11.01 (1H, s). LRMS: m/z 338 (M+1)$^+$.

Preparation 78

2-[5-(2-Ethoxyphenyl)-3-n-propyl-2,6-dihydro-7H-pyrazolo-[4,3-d]pyrimidin-7-on-2-yl]acetamidoxime Obtained as a white solid (89%) from the title compound of Preparation 77, using the procedure of Preparation 74. δ ($DMSO_{d6}$): 0.94 (3H, t), 1.33 (3H, t), 1.74 (2H, m), 2.90 (2H, t), 4.12 (2H, q), 4.92 (2H, s), 5.48 (2H, s), 7.07 (1H, m), 7.14 (1H, d), 7.46 (1H, m), 7.68 (1H, d), 9.34 (1H, s), 11.53 (1H, s). LRMS: m/z 371 (M+1)$^+$.

Preparation 79

5-(2-Ethoxyphenyl)-2-(5-methyl-1,2,4-oxadiazol-3-yl)methyl-3-n-propyl-2,6-dihydro-7H-pyrazolo[4,3-d]pyrimidin-7-one The title compound of Preparation 78 (160 mg, 0.43 mmol) was added to a mixture of acetic anhydride (122 μl, 1.3 mmol), acetic acid (2.5 ml, 40 mmol) and toluene (2 ml), then the resulting mixture stirred under reflux for 18 hours, allowed to cool and evaporated under reduced pressure. The residue was purified by column chromatography on silica gel, using an elution gradient of hexane:ethyl acetate (1:1 to 1:3), to provide the title compound (45 mg) as a solid. δ ($DMSO_{d6}$): 0.92 (3H, t), 1.31 (3H, t), 1.72 (2H, m), 2.57 (3H, s), 2.97 (2H, t), 4.12 (2H, q), 5.76 (2H, s), 7.05 (1H, m), 7.14 (1H, d), 7.47 (1H, m), 7.64 (1H, d), 11.64 (1H, s).

Preparation 80

Benzyl 1-benzyl-4-nitro-3-n-propylpyrazole-5-carboxylate

Benzyl bromide (20.4 ml, 0.172 mol) was added dropwise over 5 minutes to a stirred, ice-cooled solution of Preparation 3 (17.0 g, 0.085 mol) and cesium carbonate (56.1 g, 0.173 mol) in dimethylformamide (150 ml), then the cooling bath removed. After a further 19 hours, water (300 ml) was added and the mixture extracted with ether (1000 ml in total). The combined extracts were dried ($MgSO_4$) and evaporated under reduced pressure to furnish an oil which, on purification by column chromatography on silica gel, using an elution gradient of pentane:ethyl acetate (95:5 to 90:10), afforded the title compound (13.0 g) as a solid (as well as the 2-benzyl isomer (19.7 g)). δ ($CDCl_3$): 0.99 (3H, t), 1.76 (2H, m), 2.86 (2H, t), 5.30 (2H, s), 5.39 (2H, s), 7.17 (2H, m), 7.30 (8H, m). LRMS: m/z 397 (M+18)$^+$.

Preparation 81

1-Benzyl-4-nitro-3-n-propylyrazole-5-carboxylic acid

A mixture of the title compound of Preparation 80 (13.0 g, 0.034 mol) and 6M aqueous sodium hydroxide solution (65 ml) was stirred under reflux for 2 hours, allowed to cool, diluted with water (130 ml) and the resulting mixture extracted with ether (500 ml). The stirred aqueous phase was ice-cooled, acidified with concentrated hydrochloric acid and extracted with dichloromethane (500 ml in total). The combined dichloromethane extracts were dried ($MgSO_4$) and evaporated under reduced pressure to give the title compound (10.0 g) as a white solid. δ ($CDCl_3$): 1.10 (3H, t), 1.78 (2H, m), 2.94 (2H, t), 5.78 (2H, s), 7.32 (5H, m).

Preparation 82

1-Benzyl-4-nitro-3-n-propylpyrazole-5-carboxamide

Obtained as a cream powder(79%) from the title compound of Preparation 81, using the procedure of Preparation 5. δ (CDCl$_3$): 1.00 (3H, t), 1.76 (2H, m), 2.90 (2H, t), 5.60 (2H, s), 7.30 (5H, m). LRMS: m/z 306 (M+18)$^+$.

Preparation 83

4-Amino-1-benzyl-3-n-propylpyrazole-5-carboxamide

A stirred mixture of the title compound of Preparation 82 (7.0 g, 0.024 mol), stannous chloride dihydrate (27.4 g, 0.122 mol) and ethanol (140 ml) was heated under reflux for 2 hours. The reaction mixture was cooled, basified with saturated aqueous ammonium carbonate solution, filtered and the filtrate extracted with dichloromethane (750 ml in total). The combined extracts were dried (MgSO$_4$) and evaporated under reduced pressure to yield the title compound (4.8 g) as an orange solid. δ (CDCl$_3$): 0.99 (3H, t), 1.70 (2H, m), 2.58 (2H, t), 2.94 (2H, s), 5.70 (2H, s), 7.24 (5H, m). LRMS: m/z 259 (M+1)$^+$.

Preparation 84

5-Chlorosulphonyl-2-ethoxybenzoic acid

Molten 2-ethoxybenzoic acid (25.0 g, 0.150 mol) was added to a stirred, ice-cooled mixture of thionyl chloride (11 ml, 0.151 mol) and chlorosulphonic acid (41.3 ml, 0.621 mol), whilst maintaining the temperature of the reaction mixture below 25° C. The resulting mixture was stirred at room temperature for 18 hours and then poured into a stirred mixture of ice (270 g) and water (60 ml) to give an off-white precipitate. Stirring was continued for 1 hour, then the product was collected by filtration, washed with water and dried under vacuum to provide the title compound (36.08 g). A reference sample, m.p. 115–116° C., was obtained by crystallisation from hexane:toluene. Found: C,41.02; H, 3.27. C$_9$H$_9$ClO$_5$S requires C,40.84; H, 3.43%. δ (CDCl$_3$): 1.64(3H, t), 4.45(2H, q), 7.26(1H, d), 8.20(1H, dd), 8.80(1H, d).

Preparation 85

2-Ethoxy-5-(4-methylpiperazin-1-ylsulphonyl)benzoic acid

(a): One-Step Procedure

1-Methylpiperazine (33.6 ml, 0.303 mol) was added to a stirred suspension of the title compound of Preparation 84 (34.4g, 0.130 mol) in water (124 ml) at about 10° C., whilst maintaining the temperature of the reaction mixture below 20° C. The resulting solution was cooled to about 10° C. and, after 5 minutes, crystallisation of a solid commenced. After a further 2 hours, the solid was collected by filtration, washed with ice-water and dried under vacuum to furnish the crude product (36.7 g). A sample (15.0 g) was purified by stirring it in refluxing acetone for 1 hour; the resulting suspension was allowed to cool to room temperature and the crystalline solid collected by filtration and dried under vacuum to afford the title compound (11.7 g), m.p. 198–199° C., whose $^1$H nmr spectrum is identical with that obtained for the product of procedure (b) below.

(b): Two-Step Procedure

A solution of the title compound of Preparation 84 (50.0 g, 0.189 mol) in acetone (150 ml) was added dropwise to a stirred mixture of 1-methylpiperazine (20.81 g, 0.208 mol) and triethylamine (28.9 ml, 0.207 mol), whilst maintaining the temperature of the reaction mixture below 20° C. A white crystalline, solid formed during the addition and stirring was continued for a further 1.5 hours. Filtration, followed by washing with acetone and drying under vacuum of the product, provided the hydrochloride-triethylamine .double salt of the title compound (78.97 g), m.p. 166–169° C. Found: C,51.33; H,8.14; N,9.06; Cl,8.02. C$_{14}$H$_{20}$N$_2$O$_5$S; C$_6$H$_{15}$N; HCl requires C,51.55; H, 7.79; N,9.02; Cl, 7.61%. δ (DMSO$_{d6}$): 1.17(9H, t), 1.32(3H, t), 2.15(3H, s), 2.47(6H, br s), 2.86(2H, br s), 3.02(6H, q), 4.18(2H, q), 7.32(1H, d), 7.78(1H, d), 7.85(1H, d).

The double salt (30.0 g) was stirred in water (120 ml) to produce an almost clear solution, from which crystallisation of a solid rapidly occurred. After 2 hours, the solid was collected by filtration, washed with water and dried under vacuum to give the title compound (14.61 g) as a white solid. A reference sample, m.p. 201° C., was obtained by recrystallisation from aqueous ethanol. Found: C,51.09; H, 6.16; N,8.43. C$_{14}$H$_{20}$N$_2$O$_5$S requires C,51.21; H, 6.14; N,8.53%. δ (DMSOd6): 1.31(3H, t), 2.12(3H, s), 2.34(4H, br s), 2.84(4H, br s), 4.20(2H, q), 7.32(1H, d), 7.80(1H, dd), 7.86(1H, d).

Preparation 86

1-Benzyl-4-[2-ethoxy-5-(4-methylpiperazin-1-ylsulphonyl)benzamido]-3-n-propylpyrazole-5-carboxamide

(Benzotriazol-1-yloxy)tripyrrolidinophosphonium hexafluorophosphate (PyBOP; 7.6 g, 0.015 mol) was added to a stirred solution of the title compounds of Preparation 83 (3.8 g, 0.015 mol) and Preparation 85 (5.3 g, 0.016 mol) in dimethylformamide (50 ml) and the resulting orange solution stirred at room temperature for 20 hours, then poured into water (250 ml). The mixture was extracted with ethyl acetate (750 ml in total) and the combined extracts washed sequentially with 10% aqueous sodium bicarbonate solution (100 ml) and water (100 ml), dried (MgSO$_4$) and evaporated under reduced pressure to provide an orange solid. Crystallisation from ethanol furnished the title compound. (6.76 g) as a white crystalline solid, m.p. 182–184° C. Found: C, 58.88; H, 6.27; N, 14.66. C$_{28}$H$_{36}$N$_6$O$_5$S requires C, 59.14; H, 6.38; N, 14.78%. δ (CDCl$_3$): 0.97 (3H, t), 1.59 (3H, t), 1.68 (2H, m), 2.26 (3H, s), 2.47 (4H, m), 2.58 (2H, t), 3.08 (4H, m), 4.39 (2H, t), 5.62 (2H, s), 7.17 (1H, d), 7.26 (7H, m), 7.92 (1H, d), 8.62 (1H, S), 9.20 (1H, s). LRMS: m/z 569 (M+1)$^+$.

Preparation 87

1-(4-Chlorobenzyl)-5-(2-n-propoxyphenyl)-3-n-propyl-1,6-dihydro-7H-pyrazolo[4,3-d]pyrimidin-7-one

Obtained as a white solid (62%) from the title compound of Preparation 12 and 4-chlorobenzyl chloride, using the procedure of Preparation 15A.

Found: C, 65.96; H, 5.80; N, 12.77. C$_{24}$H$_{25}$ClN$_4$O$_2$ requires C, 65.97; H, 5.77; N, 12.82%. δ (CDCl$_3$): 1.02 (3H, t), 1.18 (3H, t), 1.88 (2H, m), 2.02 (2H, m), 2.95 (2H, t), 4.19 (2H, t), 5.74 (2H, s), 7.04 (1H, d), 7.16 (1H, m), 7.26 (2H, d), 7.37 (2H, d), 7.44 (1H, m), 8.50 (1H, d), 11.20 (1H, s). LRMS: m/z 437 (M+1)$^+$.

Preparation 88

1-(4-Chlorobenzyl)-5-(2-ethoxyphenyl)-3-n-propyl-1,6-dihydro-7H-pyrazolo[4,3-d]pyrimidin-7-one

Obtained as a white crystalline solid (77%) from the title compound of Preparation 14 and 4-chlorobenzyl chloride, using the procedure of Preparation 15A. Found: C, 65.34; H, 5.52; N, 13.38. $C_{23}H_{23}ClN_4O_2$ requires C, 65.32; H, 5.48; N, 13.25%. δ (CDCl$_3$): 1.02 (3H, t), 1.63 (3H, t), 1.90 (2H, m), 2.96 (2H, t), 4.32 (2H, q), 5.74 (2H, s), 7.05 (1H, d), 7.16 (1H, m), 7.28 (2,d), 7.38 (2H, d), 7.46 (1H, m), 8.50 (1H, d), 11.20 (1H, s). LRMS: m/z 423 (M+1)$^+$.

Preparation 89

2-(4-Bromobenzyl)-5-(2-ethoxyphenyl)-3-n-propyl-2,6-dihydro-7H-pyrazolo[4,3-d]pyrimidin-7-one Obtained as a colourless oil (54%) from the title compound of Preparation 14 and 4-bromobenzyl chloride, using the procedure of Preparation 15B. δ (CDCl$_3$): 0.94 (3H, t), 1.58 (3H, t), 1.73 (2H, m), 2.08 (2H, t), 4.08 (2H, q), 5.50 (2H, s), 7.08 (4H, m), 7.44 (3H, m), 8.38 (1H, d), 10.89 (1H, s). LRMS: m/z 484 (M+18)$^+$.

Preparation 90

1-(2-cyanobenzyl)-5-(2-ethoxyphenyl)-3-n-propyl-1,6-dihydro-7H-pyrazolo[4,3-d]pyrimidin-7-one Obtained as a solid (17%) from the title compound of Preparation 14 and 2-cyanobenzyl bromide, using the procedure of Preparation 15D. Found: C, 69.58; H, 5.60; N, 16.90. $C_{24}H_{23}N_5O_2$ requires C, 69.72; H, 5.61; N, 16.94%. δ (CDCl$_3$): 1.03 (3H, t), 1.60 (3H, t), 1.90 (2H, m), 2.98 (2H, t), 4.30 (2H, q), 6.03 (2H, s), 7.05 (2H, m), 7.16 (1H, m), 7.36 (1H, m), 7.45 (2H, m), 7.68 (1H, d), 8.54 (1H, d), 11.20 (1H, s). LRMS: m/z 414 (M+1)$^+$.

Preparation 91

1-(4-Carbamoylbenzyl)-5-(2-ethoxyphenyl)-3-n-propyl-1,6-dihydro-7H-pyrazolo[4,3-d]pyrimidin-7-one Obtained as a white solid (73%) from thetitle compound of Preparation 14 and 4-carbamoylbenzyl chloride, using the procedure of Preparation 15A. Found: C, 66.22; H, 5.81; N, 16.06. $C_{24}H_{25}N_5O_3$ requires C, 66.81; H, 5.84; N, 16.23%. δ (CDCl$_3$): 1.02 (3H, t), 1.62 (3H, t), 1.90 (2H, m), 2.96 (2H, t), 4.30 (2H, q), 5.59 (1H, s), 5.82 (2H, s), 6.00 (1H, s), 7.05 (1H, d), 7.16 (1H, m), 7.45 (3H, m), 7.78 (2H, d), 8.52 (1H, d), 11.24 (1H, s) LRMS: m/z 432 (M+1)$^+$.

Preparation 92

2-(4-Carbamoylbenzyl)-5-(2-ethoxyphenyl)-3-n-propyl-2,6-dihydro-7H-pyrazolo[4,3-d]pyrimidin-7-one Obtained as a white solid (47%) from the title compound of Preparation 14 and 4-carbamoylbenzyl bromide, using the procedure of Preparation 15B. Found: C, 66.10; H, 5.78; N, 16.02. $C_{24}H_{25}N_5O_3$; 0.07 $CH_3CO_2CH_2CH_3$ requires C, 66.63; H, 5.89; N, 16.00%. δ (CDCl$_3$): 0.95 (3H, t), 1.59 (3H, t), 1.74 (2H, m), 2.86 (2H, t), 4.30 (2H, q), 5.59 (2H, s), 5.68 (1H, s), 6.12 (1H, s), 7.03 (1H, d), 7.12 (1H, m), 7.26 (2H, d), 7.45 (1H, m), 7.79 (2H, d), 8.40 (1H, d), 10.92 (1H, s). LRMS: m/z 432 (M+1)$^+$.

Preparation 93

5-(2-Ethoxyphenyl)-1-(2-nitrobenzyl)-3-n-propyl-1,6-dihydro-7H-pyrazolo[4,3-d]pyrimidin-7-one Obtained as an off-white solid (39%) from the title compound of Preparation 14 and 2-nitrobenzyl chloride, using the procedure of Preparation 15A. Found: C, 63.62; H, 5.32; N, 16.07. $C_{23}H_{23}N_5O_4$ requires C, 63.73; H, 5.35; N, 16.16%. δ (CDCl$_3$): 1.05 (3H, t), 1.60 (3H, t), 1.92 (2H, m), 3.00 (2H, t), 4.32 (2H, q), 6.25 (2H, s), 6.70 (1H, d), 7.06 (1H, d), 7.18 (1H, m), 7.45 (3H, m), 8.14 (1H, d), 8.54 (1H, d), 11.24 (1H, s). LRMS: m/z 434 (M+1)$^+$.

Preparation 94

1-(2-Nitrobenzyl)-5-(2-n-propoxyphenyl)-3-n-propyl-1,6-dihydro-7H-pyrazolo[4,3-d]pyrimidin-7-one Obtained as a white solid (46%) from the title compound of Preparation 12 and 2-nitrobenzyl chloride, using the procedure of Preparation 15A. δ (CDCl$_3$): 1.02 (3H, t), 1.15 (3H, t), 1.90 (2H, m), 2.00 (2H, m), 2.99 (2H, t), 4.20 (2H, t), 6.24 (2H, s), 6.66 (1H, d), 7.04 (1H, d), 7.18 (1H, m), 7.45 (3H, m), 8.14 (1H, d), 8.54 (1H, d), 11.26 (1H, s). LRMS: m/z 448 (M+1)$^+$.

Preparation 95

5-(2-Ethoxyphenyl)-1-(4-nitrobenzyl)-3-n-propyl-1,6-dihydro-7H-pyrazolo[4,3-d]pyrimidin-7-one Obtained as a crystalline solid (61%) from the title compound of Preparation 14 and 4-nitrobenzyl chloride, using the procedure of Preparation 15A. Found: C, 63.59; H, 5.31; N, 16.02. $C_{23}H_{23}N_5O_4$ requires C, 63.73; H, 5.35; N, 16.16%. δ (CDCl$_3$): 1.02 (3H, t), 1.60 (3H, t), 1.88 (2H, m), 2.97 (2H, t), 4.30 (2H, q), 5.84 (2H, s), 7.04 (1H, d), 7.16 (1H, m), 7.46 (1H, m), 7.52 (2H, d), 8.18 (2H, d), 8.50 (1H, d), 11.26 (1H, s). LRMS: m/z 434 (M+1)$^+$.

Preparation 96

5-(2-Ethoxyphenyl)-2-(4-nitrobenzyl)-3-n-propyl-2,6-dihydro-7H-pyrazolo[4,3-d]pyrimidin-7-one Obtained as a yellow solid (30%) from the title compound of Preparation 14 and 4-nitrobenzyl bromide, using the procedure of Preparation 15C. δ (CDCl$_3$): 0.98 (3H, t), 1.60 (3H, t), 1.76 (2H, m), 2.90 (2H, t), 4.30 (2H, q), 5.64 (2H, s), 7.05 (1H, d), 7.14 (1H, m), 7.36 (2H, d), 7.46 (1H, m), 8.20 (2H, d), 8.41 (1H, d), 10.98 (1H, s). LRMS: m/z 434 (M+1)$^+$.

Preparation 97

1-(2-Aminobenzyl)-5-{5-[4-(2-t-butyldimethylsilyloxyethyl)piperazin-1-ylsulphonyl]-2-n-propoxyphenyl}-3-n-propyl-1,6-dihydro-7H-pyrazolo-[4,3-d]pyrimidin-7-one Imidazole (39 mg, 0.57 mmol) and t-butyldimethylsilyl chloride (69 mg, 0.46 mmol) were added to a stirred solution of the title compound of Example 53 (233 mg, 0.38 mmol) in dichloromethane (4 ml) and the mixture stirred at room temperature for 20 hours. Water (5 ml) was added, the aqueous phase separated and extracted with dichloromethane (20 ml), then the combined organic solutions dried (Na$_2$SO$_4$) and evaporated under reduced pressure. The resulting yellow oil was purified by column chromatography on silica gel, using pentane:ethyl acetate (1:1) as eluant, to afford the title compound (212 mg) as a colourless oil. δ (CDCl$_3$): 0.00 (6H, s), 0.85 (9H, s), 1.02 (3H, t), 1.20 (3H, t), 1.88 (2H, m), 2.06 (2H, m), 2.52 (2H, t), 2.62 (4H, m), 2.95 (2H, t), 3.08 (4H, m), 3.66 (2H, t), 4.26 (2H, t), 5.79 (2H, s), 7.18 (2H, m), 7.36 (1H, m), 7.60 (1H, d), 7.70 (1H, d), 7.82 (1H, d), 8.80 (1H, s), 9.70 (1H, s), 10.98 (1H, s). LRMS: m/z 724 (M+1)$^+$.

Preparation 98

5-{5-[4-(2-t-Butyldimethylsilyloxyethyl)piperazin-1-ylsulphonyl]-2-n-propoxyphenyl}-1-(2-methanesulphonamidobenzyl-3-n-propyl-1,6-dihydro-7H-pyrazolo[4,3-d]pyrimidin-7-one Methanesulphonyl chloride (24 μl, 0.30 mmol) was added to a stirred, ice-cooled solution of the title compound of Preparation 97 (200 mg, 0.28 mmol) in pyridine (3 ml) and the mixture stirred at room temperature for 20 hours, then evaporated under reduced pressure. The residue was treated with water (10 ml) and the resulting suspension:extracted with ethyl acetate (40 ml in total). The combined extracts were dried ($Na_2SO_4$) and evaporated under reduced pressure to give a yellow oil which was purified by column chromatography on silica gel, using pentane:ethyl acetate (1:1) as eluant, to provide the title compound (145 mg) as a colourless oil. δ ($CDCl_3$): 0.00 (6H, s), 0.85 (9H, s), 1.02 (3H, t), 1.20 (3H, t), 1.88 (2H, m), 2.06 (2H, m), 2.52 (2H, t), 2.62 (4H, m), 2.95 (2H, t), 3.08 (4H, m), 3.66 (2H, t), 4.26 (2H, t), 5.79 (2H, s), 7.18 (2H, m), 7.36 (1H, m), 7.60 (1H, d), 7.70 (1H, d), 8.80 (1H, s), 9.70 (1H, s), 10.98 (1H, s). LRMS: m/z 802 (M+1)$^+$.

Preparation 99

5-(2-Ethoxyphenyl)-3-n-propyl-1-(4-sulphamoylbenzyl)-1,6-dihydro-7H-pyrazolo[4,3-d]pyrimidin-7-one Obtained as a solid (51%) from the title compound of Preparation 14 and 4-sulphamoylbenzyl chloride (J. Med. Chem., 1986, 29, 18.14), using the procedure of Preparation 15A. Found: C, 58.78; H, 5.37; N, 14.83. $C_{23}H_{25}N_5O_4S$ requires C, 59.08; H, 5.39; N, 14.98%. δ ($DMSO_{d6}$): 0.90 (3H, t), 1.32 (3H, t), 1.74 (2H, m), 2.79 (2H, t), 4.14 (2H, q), 5.78 (2H, s), 7.04 (1H, m), 7.16 (1H, d), 7.28 (2H, s), 7.38 (2H, d), 7.45 (1H, m), 7.66 (1H, d), 7.78 (2H, d), 12.02 (1H, s). LRMS: m/z 468 (M+1)$^+$.

Preparation 100

1-Benzyloxycarbonylmethyl-5-(2-n-propoxyphenyl)-3-n-propyl-1,6-dihydro-7H-pyrazolo[4,3-d]pyrimidin-7-one Obtained as a white solid (28%) from the title compound of Preparation 12 and benzyl bromoacetate, using the procedure of Preparation 15D. δ ($CDCl_3$): 1.02 (3H, t), 1.17 (3H, t), 1.90 (2H, m), 2.02 (2H, m), 2.97 (2H, t), 4.19 (2H, t), 5.21 (2H, s), 5.42 (2H, s), 7.06 (1H, d), 7.17 (1H, m), 7.33 (5H, m), 7.47 (1H, m), 8.50 (1H, d), 11.23 (1H, s). LRMS: m/z 461 (M+1)$^+$.

Preparation 101

1-Carboxymethyl-5-(2-n-propoxyphenyl)-3-n-propyl-1,6-dihydro-7H-pyrazolo[4,3-d]pyrimidin-7-one Obtained as a beige solid (92%) from the title compound of Preparation 1.00, using the procedure of Preparation 69. δ ($CDCl_3$): 1.04 (3H, t), 1.18 (3H, t), 1.91 (2H, m), 2.01 (2H, m), 2.97 (2H, t), 4.20 (2H, t), 5.41 (2H, s), 7.06 (1H, d), 7.17 (1H, m), 7.48 (1H, m), 8.51 (1H, d), 11.36 (1H, s). LRMS: m/z 371 (M+1)$^+$.

Preparation 102

1-(N-Ethylcarbamoylmethyl)-5-(2-n-propoxyphenyl)-3-n-propyl-1,6-dihydro-7H-pyrazolo[4,3-d]pyrimidin-7-one N-Methylmorpholine (91 μl, 0.83 mmol) was added to a stirred solution of the title compound of Preparation 101 (93 mg, 0.23 mmol) in dichloromethane (5 ml) under nitrogen and the resulting solution cooled in an ice-bath. Ethylamine hydrochloride (24 mg, 0.30 mmol), 1-hydroxybenzotriazole hydrate (41 mg, 0.30 mmol) and 1-(3-dimethylaminopropyl)-3-ethylcarbodiimide hydrochloride (73 mg, 0.38 mmol) were added, then the resulting mixture allowed to warm to room temperature, stirred for a further 20 hours and evaporated under reduced pressure. The residue was partitioned between ethyl acetate (10 ml) and 2M hydrochloric acid (10 ml), the separated aqueous phase washed with ethyl acetate (10 ml) and the combined organic solutions washed successively with saturated aqueous sodium bicarbonate solution (10 ml) and brine (10 ml), dried ($MgSO_4$) and evaporated under reduced pressure to give the title compound (89 mg) as a cream solid. δ ($CDCl_3$): 1.03 (3H, t), 1.10 (3H, t); 1.18 (3H, t), 1.90 (2H, m), 2.01 (2H, m), 2.98 (2H, t), 3.36 (2H, m), 4.19 (2H, t), 5.23 (2H, s), 6.22 (1H, s), 7.06 (1H, d), 7.18 (1H, m), 7.49 (1H, m), 8.52 (1H, d), 11.29 (1H, s).

LRMS: m/z 398 (M+1)$^+$.

Preparation 103

1-[N-(2-Methoxyethyl)carbamoylmethyl]-5-(2-n-propoxyphenyl)-3-n-propyl-1,6-dihydro-7H-pyrazolo[4,3-d]pyrimidin-7-one Obtained as a white powder (44%) from the title compound of Preparation 101 and 2-methoxyethylamine, using the procedure of Preparation 102. δ ($CDCl_3$): 1.03 (3H, t), 1.18 (3H, t), 1.88 (2H, m), 2.00 (2H, m), 2.98 (2H, t), 3.29 (3H, s), 3.42 (4H, m), 4.21 (2H, t), 5.29 (2H, s), 6.45 (1H, s), 7.04 (1H, d), 7.15 (1H, d), 7.48 (1H, m), 8.50 (1H, d), 11.27 (1H, s).

LRMS: m/z 428 (M+1)$^+$.

Preparation 104

1-(Morpholin-4-ylcarbonylmethyl)-5-(2-n-propoxyphenyl)-3-n-propyl-1,6-dihydro-7H-pyrazolo[4,3-d]pyrimidin-7-one Obtained as a cream foam (95%) from the title compound of Preparation 101 and morpholine, using the procedure of Preparation 102. δ ($CDCl_3$): 1.03 (3H, t), 1.19 (3H, t), 1.90 (2H, m), 2.00 (2H, m), 2.98 (2H, t), 3.50–3.78 (8H, m), 4.19 (2H, t), 5.45 (2H, s), 7.05 (1H, d), 7.18 (1H, m), 7.46 (1H, m), 8.50 (1H, d), 11.20 (1H, s). LRMS: m/z440 (M+1)$^+$.

Preparation 105

2-(N-Ethylcarbamoylmethyl)-5-(2-n-propoxyphenyl)-3-n-propyl-2,6-dihydro-7H-pyrazolo[4,3-d]pyrimidin-7-one Obtained as a white powder (58%) from the title compound of Preparation 69 and ethylamine hydrochloride, using the procedure of Preparation 102. δ ($CDCl_3$): 1.10 (3H, t), 1.05 (3H, t), 1.14 (3H, t), 1.82 (2H, m), 2.02 (2H, m), 3.00 (2H, t), 3.30 (2H, m), 4.19 (2H, t), 4.99 (2H, s), 6.23 (1H, s), 7.07 (1H, d), 7.15 (1H, m), 7.48 (1H, m), 8.42 (1H, d), 11.00 (1H, s). LRMS: m/z 398 (M+1)$^+$.

Preparation 106

2-[N-(2-Methoxyethyl)carbamoylmethyl]-5-(2-n-propoxyphenyl)-3-n-propyl-2,6-dihydro-7H-pyrazolo[4,3-d]pyrimidin-7-one Obtained as a cream foam (74%) from the title compound of Preparation 69 and 2-methoxyethylamine,.using the procedure of Preparation 102. δ (CDCl₃): 1.02 (3H, t), 1.15 (3H, t), 1.84 (2H, m), 2.00 (2H, m), 3.00 (2H, t), 3.28 (3H, s), 3.40 (4H, m), 4.19 (2H, t), 5.00 (2H, s), 6.40 (1H, s), 7.06 (1H, d), 7.16 (1H, m), 7.46 (1H, m), 8.43 (1H, d), 10.97 (1H, s). LRMS: m/z 428 M+1)⁺.

Preparation 107

2-(Morpholin-4-ylcarbonylmethyl)-5-(2-n-propoxyphenyl)-3-n-propyl-2,6-dihydro-7H-pyrazolo[4,3-d]pyrimidin-7-one Obtained as a white foam (55%) from the title compound of Preparation 69 and morpholine, using the procedure of Preparation 102. δ (CDCl₃): 1.05 (3H, t), 1.13 (3H, t), 1.91 (2H, m), 2.00 (2H, m), 3.01 (2H, t), 3.66 (8H, m), 4.17 (2H, t), 5.20 (2H, s), 7.04 (1H, d), 7.15 (1H, m), 7.45 (1H, m), 8.41 (1H, d), 10.36 (1H, s). LRMS: m/z 440 (M+1)⁺.

Preparation 108

4-(2S-Chloropropanoyl)morpholine

N-Methylmorpholine (1.5 ml, 13.8 mmol) followed by 1-hydroxybenzotriazole (1.483 g, 11.0 mmol) and 1-(3-dimethylaminopropyl)-3-ethylcarbodiimide hydrochloride (2.317 g, 12.0 mmol), were added to a stirred, ice-cooled solution of S-(−)-2-chloropropionic acid (1.0 g, 9.2 mmol) in dichloromethane (30 ml) and the resulting solution stirred at about 0° C. for 45 minutes. Morpholine (2.4 ml, 27.6 mmol) was then added, the cooling bath removed and the reaction mixture stirred at room temperature for 66 hours, then evaporated under reduced pressure. The residue was partitioned between ethyl acetate and water, then the separated organic phase washed with brine, dried (MgSO₄) and evaporated under reduced pressure. The resulting yellow oil was purified by column chromatography on silica gel, using mixtures of hexane:ethyl acetate (3:1 and then 2:1) as eluants, to provide the title compound (57 mg) as a colourless oil. $[\alpha]_D^{25}$ +51° (c=0.1, CH₃OH). δ (CDCl₃): 1.67 (3H, d), 3.42–3.89 (8H, m), 4.53 (1H, q). LRMS: m/z 195 (M+NH₄)⁺.

Preparation 109

1-[1S-(Morpholin-4-ylcarbonyl)ethyl]-5-(2-n-propoxyphenyl)-3-n-propyl-1,6-dihydro-7H-pyrazolo[4,3-d]pyrimidin-7-one Obtained as a white foam (44%) from the title compounds of Preparation 12 and Preparation 108, using the procedure of Preparation 15B. δ (CDCl₃): 1.02 (3H, t), 1.18 (3H, t), 1.78 (3H, d), 1.88 (2H, m), 2.03 (2H, m), 2.98 (2H, m), 3.40–3.74 (8H, m), 4.20 (2H, t), 6.18 (1H, q), 7.06 (1H, d), 7.16 (1H, m), 7.46 (1H, m), 8.52 (1H, d), 11.24 (1H, s). LRMS: m/z 454 (M+1)⁺.

Preparation 110

2-[1S-(Morpholin-4-ylcarbonyl)ethyl]-5-(2-n-propoxyphenyl)-3-n-propyl-2,6-dihydro-7H-pyrazolo[4,3-d]pyrimidin-7-one Obtained as a white foam (33%) from the title compounds of Preparation 12 and Preparation 108, using the procedure of Preparation 15B. δ (CDCl₃): 1.05 (3H, t), 1.15 (3H, t), 1.82 (3H, d), 1.90 (2H, m), 2.00 (2H, m), 2.98 (2H, m), 3.30 (2H, m), 3.48 (2H, m), 3.66 (4H, m), 4.19 (2H, t), 5.58 (1H, q), 7.06 (1H, d), 7.47 (1H, m), 8.40 (1H, d), 10.94 (1H, s). LRMS: m/z 454 (M+1)⁺.

Preparation 111

4-(2R-Chloropropanoyl)morpholine

Obtained as a pale yellow oil (16%) from R-(+)-2-chloropropionic acid and morpholine, using the procedure of Preparation 108. $[\alpha]_D^{25}$ −46° (c=0.1, CH₃OH). δ (CDCl₃): 1.69 (3H, d), 3.49–3.87 (8H, m), 4.53 (1H, q). LRMS: m/z 195 (M+NH₄)⁺.

Preparation 112

1-[1R-(Morpholin-4-ylcarbonyl)ethyl]-5-(2-n-propoxyphenyl)-3-n-propyl-1,6-dihydro-7H-pyrazolo[4,3-d]pyrimidin-7-one Obtained as a yellow solid (8%) from the title compounds of Preparation 12 and Preparation 111, using the procedure of Preparation 15B. δ (CDCl₃): 1.02 (3H, t), 1.18 (3H, t), 1.79 (3H, d), 1.91 (2H, m), 2.04 (2H, m), 2.98 (2H, m), 3.40–3.76 (8H, m) 4.20 (2H, t), 6.19 (1H, q), 7.06 (1H, d), 7.18 (1H, m), 7.46 (1H, m), 8.52 (1H, d), 11.24 (1H, s). LRMS: m/z 454 (M+1)⁺.

Preparation 113

2-[1R-(Morpholin-4-ylcarbonyl)ethyl]-5-(2-n-propoxyphenyl)-3-n-propyl-2,6-dihydro-7H-pyrazolo[4,3-d]pyrimidin-7-one Obtained as a yellow powder (23%) from the title compounds of Preparation 12 and Preparation 111, using the procedure of Preparation 15B. δ (CDCl₃): 1.04 (3H, t), 1.14 (3H, t), 1.82 (3H, d), 1.92 (2H, m), 2.00 (2H, m), 2.99 (2H, m), 3.30 (2H, m), 3.48 (2H, m), 3.63 (4H, m), 4.19 (2H, t), 5.59 (1H, q), 7.06 (1H, d), 7.16 (1H, m), 7.45 (1H, m), 8.40 (1H, d), 10.95 (1H, s). LRMS: m/z 454 (M+1)⁺.

Preparation 114

1-(2-Morpholin-4-ylethyl)-5-(2-n-propoxyphenyl)-3-n-propyl-1,6-dihydro-7H-pyrazolo[4,3-d]pyrimidin-7-one Obtained as a clear oil (40%) from the title compound of Preparation 12 and the free base of 4-(2-chloroethyl)morpholine hydrochloride, using the procedure of Preparation 15B. δ (CDCl₃): 1.03 (3H, t), 1.15 (3H, t), 1.88 (2H, m), 2.00 (2H, m), 2.52 (4H, m), 2.88 (2H, t), 2.93 (2H, t), 3.62 (4H, m), 4.19 (2H, t), 4.70 (2H, t), 7.04 (1H, d), 7.15 (1H, m), 7.44 (1H, m), 8.50 (1H, d), 10.65 (1H, s). LRMS: m/z 427 (M+2)⁺.

Preparation 115

2-(2-Morpholin-4-ylethyl)-5-(2-n-propoxyphenyl)-3-n-propyl-2,6-dihydro-7H-pyrazolo[4,3-d]pyrimidin-7-one Obtained as a yellow foam (24%) from the title compound of Preparation 12 and the free base of 4-(2-chloroethyl)morpholine hydrochloride, using the procedure of Preparation 15B. Found: C, 63.90; H, 7.33; N, 16.21. C₂₃H₃₁N₅O₃; 0.10 CH₂Cl₂ requires C, 63.93; H, 7:25; N, 16.14%. δ (CDCl₃): 1.06 (3H, t), 1.14 (3H, t), 1.88 (2H, m), 2.00 (2H, m), 2.52 (4H, m), 3.00 (4H, m), 3.69 (4H, m), 4.18 (2H, t), 4.42 (2H, t), 7.04 (1H, d), 7.14 (1H, m), 7.45 (1H, m), 8.40 (1H, d), 10.85 (1H, s). LRMS: m/z 426 (M+1)⁺.

Preparation 116

2-[2-(4-Methylpiperazin-1-yl)ethyl]-5-(2-n-propoxyphenyl)-3-n-propyl-2,6-dihydro-7H-pyrazolo[4,3-d]pyrimidin-7-one Obtained as a white foam (17%) from the title compound of Preparation 12 and 1-(2-chloroethyl)-4-methylpiperazine (Europ. J. Med. Chem., 1995, 30, 77), using the procedure of Preparation 15B. δ (CDCl$_3$): 1.05 (3H, t), 1.12 (3H, t), 1.86 (2H, m), 1.98 (2H, m), 2.28 (3H, s), 2.44 (4H, m), 2.58 (4H, m), 2.97 (4H, m), 4.17 (2H, t), 4.39 (2H, t), 7.03 (1H, d), 7.12 (1H, m), 7.44 (1H, m), 8.40 (1H, d), 10.85 (1H, s). LRMS: m/z 439 (M+1)$^+$.

Preparation 117

1-(2-Chloroethyl)pyrazole

1-Bromo-2-chloroethane (6.0 ml, 72 mmol) was added dropwise, under nitrogen, to a vigorously stirred, ice-cooled mixture of pyrazole (5.0 g, 73 mmol), potassium carbonate (10.0 g, 73 mmol) and acetone (95 ml). After 3 hours, the cooling bath was removed and the reaction mixture stirred at room temperature for a further 3 days, then filtered. The filtrate was evaporated under reduced pressure and the residue purified by column chromatography on silica gel, using dichloromethane:methanol (97:3) as eluant, to yield the title compound (1.62 g) as a clear oil. δ (CDCl$_3$): 3.90 (2H, m), 4.42 (2H, m), 6.23 (1H, s), 7.63 (1H, s), 7.65 (1H, s). LRMS: m/z 131 (M+1)$^+$.

Preparation 118

5-(2-n-Propoxyphenyl)-3-n-propyl-2-(2-pyrazol-1-ylethyl)-2,6-dihydro-7H-pyrazolo[4,3-d]pyrimidin-7-one Obtained as a white solid (63%) from the Title compounds of Preparation 12 and Preparation 117, using the procedure of Preparation 15B. δ (CDCl$_3$): 0.82 (3H, t), 1.10 (3H, t), 1.56 (2H, m), 1.98 (2H, m), 2.47 (2H, t), 4.16 (2H, t), 4.64 (2H, m), 4.78 (2H, m), 6.02 (1H, s), 6.88 (1H, s), 7.00 (1H, d), 7,04 (1H, m), 7.40 (1H, m), 7.50 (1H, m), 8.36 (1H, d), 10.58 (1H, s). LRMS: m/z 407 (M+1)$^+$.

Preparation 119

1-(2-Chloroethyl)-1,2,3-triazole

Sodium methoxide (7.0 g, 121 mmol) was added to a stirred, ice-cooled solution of 1,2,3-triazole (8.4 g, 121 mmol) in methanol (125 ml) followed, dropwise, by 1-bromo-2-chloroethane (10.0 ml, 121 mmol). The cooling bath was removed and the reaction mixture stirred at room temperature for 2 days, then evaporated under reduced pressure. The residue was partitioned between ethyl acetate (125 ml) and brine (100 ml), then the separated organic phase dried (MgSO$_4$) and evaporated under reduced pressure. The residue was purified by column chromatography on silica gel, using dichloromethane: methanol (96:4) as eluant, to furnish the title compound (2.19 g) as a clear oil. δ (CDCl$_3$): 3.88 (2H, m), 4.68 (2H, m), 7.50 (1H, s), 7.60 (1H, s). LRMS: m/z 132 (M+1)$^+$.

Preparation 120

5-(2-n-Propoxyphenyl)-3-n-propyl-2-[2-(1,2,3-triazol-1-yl)ethyl]-2,6-dihydro-7H-pyrazolo[4,3-d]pyrimidin-7-one Obtained as a white solid (60%) from the title compounds of Preparation 12 and Preparation 119, using the procedure of Preparation 15B. δ (CDCl$_3$): 0.82 (3H, t), 1.07 (3H, t), 1.50 (2H, m), 1.96 (2H, m), 2.56 (2H, t), 4.08 (2H, t), 4.72 (2H, t), 5.04 (2H, t), 7.00 (1H, d), 7.04–7.08 (2H, m), 7.40 (1H, m), 7.46 (1H, s), 8.38 (1H, d), 10.96 (1H, s). LRMS: m/z 408 (M+1)$^+$.

Preparation 121

1-(2-Chloroethyl)-1,2,4-triazole

Obtained as a clear oil (22%) from 1,2,4-triazole and 1-bromo-2-chloroethane, using the procedure of Preparation 117. δ (CDCl$_3$): 3.79 (2H, m), 4.18 (2H, m), 7.84 (1H, s), 8.04 (1H, s).

Preparation 122

5-(2-n-Propoxyphenyl)-3-n-propyl-2-[2-(1,2,4-triazol-1-yl)ethyl]-2,6-dihydro-7H-pyrazolo[4,3-d]pyrimidin-7-one Obtained as a white foam (32%) from the title compounds of Preparation 12 and Preparation 121, using the procedure of Preparation 15B. δ (CDCl$_3$): 0.88 (3H, t), 1.11 (3H, t), 1.58 (2H, m), 1.98 (2H, m), 2.60 (2H, m), 2.84 (2H, t), 4.68 (2H, t), 4.88 (2H, t), 7.00 (1H, d), 7.06 (1H, m), 7.40 (1H, m), 7.68 (1H, s), 7.92 (1H, s), 8.32 (1H, d), 10.90 (1H, s). LRMS: m/z 408 (M+1)$^+$.

Preparation 123

2-(2-Nitrophenyl)-5-(2-n-propoxyphenyl)-3-n-propyl-2,6-dihydro-7H-pyrazolo[4,3-d]pyrimidin-7-one Obtained as a yellow powder (60%) from the title compound of Preparation 12 and 2-fluoronitrobenzene, using the procedure of Preparation 15B. δ (CDCl$_3$): 0.90 (3H, t), 1.07 (3H, t), 1.76 (2H, m), 1.99 (2H, m), 2.84 (2H, t), 4.15 (2H, t), 7.01 (1H, d), 7.10 (1H, t), 7.43 (1H, t), 7.58 (1H, d), 7.70 (1H, t), 7.78 (1H, t), 8.16 (1H, d), 8.42 (1H, m), 10.93 (1H, s). LRMS: m/z 434 (M+1)$^+$.

Preparation 124

2-(4-Nitrophenyl)-5-(2-n-propoxyphenyl)-3-n-propyl-2,6-dihydro-7H-pyrazolo[4,3-d]pyrimidin-7-one Obtained as a yellow solid (72%) from the title compound of Preparation 12 and 4-fluoronitrobenzene, using the procedure of Preparation 15B. δ (CDCl$_3$): 0.96 (3H, t), 1.14 (3H, t), 1.80 (2H, m), 2.02 (2H, m), 3.12 (2H, t), 4.20 (2H, t), 7.08 (1H, d), 7.18 (1H, t), 7.49 (1H, t), 7.84 (2H, d), 8.45 (3H, m), 11.03 (1H, s). LRMS: m/z 434 (M+1)$^+$.

Preparation 125

5-(2-n-Propoxyphenyl)-3-n-propyl-2-pyrimidin-2-yl-2,6-dihydro-7H-pyrazolo[4,3-d]pyrimidin-7-one Obtained as a white solid (26%) from the title compound of Preparation 12 and 2-chloropyrimidine, using the procedure of Preparation 15B. δ (CDCl$_3$): 1.00 (3H, t), 1.17 (3H, t), 1.80 (2H, m), 2.01 (2H, m), 3.48 (2H, t), 4.19 (2H, t), 7.05 (1H, d), 7.17 (1H, m), 7.40 (1H, m), 7.46 (1H, m), 8.50 (1H, d), 8.92 (2H, d), 10.98 (1H, s). LRMS: m/z 391 (M+1)$^+$.

Preparation 126

2-Cyclobutylmethyl-5-(2-ethoxyphenyl)-3-n-propyl-2,6-dihydro-7H-pyrazolo[4,3-d]pyrimidin-7-one Obtained (25%) from the title compound of Preparation 14 and methanesulphonyloxymethylcyclobutane (J. Chem. Soc. Perkin II, 1981, 970), using the procedure of Preparation 15C. Found: C, 68.62; H, 7.13; N, 15.21. C$_{21}$H$_{26}$N$_4$O$_2$ requires C, 68.83; H, 7.15; N, 15.29%. δ (CDCl$_3$): 1.05 (3H, t), 1.58 (3H, t), 1.88 (6H, m), 2.07 (2H, m), 2.88 (3H, s), 4.30 (4H, m), 7.03 (1H, d), 7.12 (1H, m), 7.44 (1H, m), 8.40 (1H, d), 10.84 (1H, s). LRMS: m/z 367 M+1)$^+$.

Preparation 127

2-Cyclobutylmethyl-5-(2-n-propoxyphenyl)-3-n-propyl-2,6-dihydro-7H-pyrazolo[4,3-d]pyrimidin-7-one Obtained as a white solid (23%) from the title compound of Preparation 12 and methanesulphonyloxymethylcyclobutane (J. Chem. Soc. Perkin II, 1981, 970), using the procedure of Preparation 15C. δ (CDCl$_3$): 1.05 (3H, t), 1.12 (3H, t), 1.84–2.06 (10H, m), 2.98 (3H, m), 4.17 (2H, t), 4.32 (2H, d), 7.04 (1H, d), 7.12 (1H, m), 7.44 (1H, m), 8.39 (1H, d), 10.70 (1H, s). LRMS: m/z 381 (M+1)$^+$.

Preparation 128

Methyl 2-(2-methoxyethoxy)benzoate

Diethyl azodicarboxylate (7.0 g, 40.4 mmol) was added dropwise to a stirred solution of methyl salicylate (5.1 g, 33.5 mmol), 2-methoxyethanol (2.6 g, 34.1 mmol) and triphenylphosphine (10.6 g, 40.4 mmol), then the reaction mixture stirred at room temperature for 18 hours and evaporated under reduced pressure. The residue was triturated with ether, the resulting mixture filtered, the filtrate evaporated under reduced pressure and the resulting residue purified by column chromatography on silica gel, using an elution gradient of pentane:ether (100:0 to 80:20), to afford the title compound (4.809, 68%) as a colourless oil. δ (CDCl$_3$):3.51 (3H, s), 3.85 (2H, t), 3.92 (3H, s), 4.23 (2H, t), 7.03 (2H, m), 7.48 (1H, m), 7.83 (1H, d).

Preparation 129

2-(2-Methoxyethoxy)benzoic acid

A mixture of the title compound of Preparation 128 (4.8 g, 22.8 mmol) and 2M aqueous sodium hydroxide solution (25 ml, 50 mmol) was stirred at room temperature for 4 hours, then washed with ether. The resulting aqueous solution was acidified to pH 3 using 1M hydrochloric acid and extracted with dichloromethane (3×50 ml). The, combined extracts were dried (MgSO$_4$) and evaporated under reduced pressure to give the title compound (4.16 g, 93%) as an oil. δ (CDCl$_3$): 3.50 (3H, s), 3.86 (2H, t), 4.41 (2H, t), 7.08 (1H, d), 7.19 (1H, m), 7.58 (1H, m), 8.22 (1H, d).

Preparation 130

3-Ethyl-4-nitro-2-(pyridin-2-yl)methylpyrazole-5-carboxamide

A mixture of the title compound of Preparation 6 (20.0 g, 109 mmol), 2-chloromethylpyridine hydrochloride (17.9 g, 109 mmol), cesium carbonate (74.7 g, 222 mmol) and dimethylformamide (120 ml) was stirred at room temperature for 18 hours, then evaporated under reduced pressure. The residue was partitioned between dichloromethane (100 ml) and, water (100 ml), then the aqueous phase separated and extracted with dichloromethane (3×100 ml). The organic phase was added to the extracts and the combined dichloromethane solutions dried (MgSO$_4$) and evaporated under reduced pressure. Crystallisation of the residue from dichloromethane:methanol provided the 1-isomer of the title compound, i.e. 3-ethyl-4-nitro-1-(pyridin-2-yl)methylpyrazole-5-carboxamide.

The mother liquor was evaporated under reduced pressure and the residue purified by column chromatography on silica gel, using an elution gradient of dichloromethane:methanol (100:0 to 95:5), to yield the title compound (17.36g, 58%) as a white solid. δ (CDCl$_3$): 1.16 (3H, t), 3.06 (2H, q), 5.48 (2H, s), 5.88 (1H, s), 7.19 (1H, d), 7.27 (2H, m), 7.70 (1H, m), 8.57 (1H, d).

Preparation 131

4-Amino-3-ethyl-2-(pyridin-2-yl)methylpyrazole-5-carboxamide

Obtained as a white solid (87%) from the title compound of Preparation 130, using the procedure of Preparation 7 except that the hydrogenation was conducted for only 4 hours. δ (CDCl$_3$): 1.03 (3H, t), 2.53 (2H, q), 4.00 (2H, s), 5.22 (1H, s), 5.36 (2H, s), 6.60 (1H, s), 6.81 (1H, d), 7.20 (1H, m), 7.62 (1H, m), 8.57 (1H, d). LRMS: m/z 246 (M+1)$^+$.

Preparation 132

3-Ethyl-4-[2-(2-methoxyethoxy)benzamido]-2-(pyridin-2-yl)methylpyrazole-5-carboxamide Oxalyl chloride (3.05 g, 24 mmol) was added dropwise to a stirred solution of the title compound of Preparation 129 (2.35 g, 12 mmol) and dimethylformamide (5 drops) in dichloromethane (40 ml) and the reaction mixture stirred at room temperature for 1 hour, then evaporated under reduced pressure.

A solution of the residual, crude acyl chloride in dichloromethane (20 ml) was added dropwise to a stirred suspension of the title compound of Preparation 131 (2.45 g, 10 mmol) in a mixture of triethylamine (5.05 g, 50 mmol) and dichloromethane (20 ml). The reaction mixture was stirred at room temperature for 18 hours and then evaporated under reduced pressure. The residue was partitioned between ethyl acetate (50 ml) and water (20 ml), then the organic phase washed successively with 1M aqueous citric acid solution (20 ml), 2M aqueous sodium hydroxide solution (20 ml) and brine (20 ml), dried (MgSO$_4$) and evaporated under reduced pressure. The crude product was purified by column chromatography on silica gel, using an elution gradient of dichloromethane:methanol (100:0 to 93:7), to furnish the title compound (3.19 g, 75%) as a foam. δ (CDCl$_3$): 1.08 (3H, t), 2.84 (2H, q), 3.36 (3H, s), 3.94 (2H, t), 4.40 (2H, t), 5.27 (1H, s), 5.48 (2H, s), 6.73 (1H, s), 6.92 (1H, d), 7.07 (2H, m), 7.22 (1H, m), 7.45 (1H, m), 7.65 (1H, m), 8.23 (1H, d), 8.59 (1H, d), 10.34 (1H, s). LRMS: m/z 424 (M+1)$^+$.

Preparation 133

3-Ethyl-5-[2-(2-methoxyethoxy)phenyl]-2-(pyridin-2-yl)methyl-2,6-dihydro-7H-pyrazolo[4,3-d]pyrimidin-7-one Potassium t-butoxide (1.12 g, 10 mmol) was added to a stirred solution of the title compound of Preparation 132 (3.15 g, 7.45 mmol) in n-propanol (40 ml) and the reaction mixture heated under reflux for 6 hours, then allowed to cool. Ethyl acetate (60 ml) was added and the resulting mixture washed successively with 1M aqueous citric acid solution (25 ml) and brine (25 ml), dried (MgSO$_4$) and evaporated under reduced pressure. The residue was purified by column chromatography on silica gel, using an elution gradient of dichloromethane:methanol (100:0 to 95:5) to afford the title compound (2.17 g, 72%). δ (CDCl$_3$): 1.29

(3H, t), 3.00 (2H, q), 3.57 (3H, s), 3.86 (2H, t), 4.35 (2H, t), 5.68 (2H, s), 7.05 (2H, m), 7.12 (1H, m), 7.20 (1H, m), 7.43 (1H, m), 7.60 (1H, m), 8.34 (1H, d), 8.57 (1H, d), 11.03 (1H, s). LRMS:, m/z 407 (M+2)$^+$.

Preparation 134

5-Chlorosulphonyl-2-n-propoxybenzoic acid

A three-neck flask, equipped with a 5M aqueous sodium hydroxide scrub (550 ml), was charged with thionyl chloride (40 ml, 0.55 mol) and chlorosulphonic acid (150 ml, 2.26 mol) and the stirred mixture cooled to about −10° C. A solution of 2-n-propoxybenzoic acid (100 g, 0.55 mol) in dichloromethane (200 ml) was added over 20 minutes, ensuring that the reaction temperature was maintained below 5° C., then the reaction mixture was allowed to warm to room temperature. The resulting solution was added over 1 hour to stirred, ice-cold water, whilst maintaining the temperature at about 0° C., and stirring continued for a further 30 minutes. The mixture was filtered and the solid thus obtained was washed with cold water (100 ml) and dried under vacuum to give the title compound (122.2 g, 80%) as a white solid. δ (DMSOd$_6$): 1.13 (3H, t), 2.00 (2H, m), 4.32 (2H, t), 7.23 (1H, d), 8.21, (1H, m), 8.82 (1H, d).

Preparation 135

5-(4-Ethylpiperazin-1-ylsulphonyl)-2-n-propoxybenzoic acid

1-Ethylpiperazine (135 ml, 1.063 mol) was added over 10 minutes to a stirred, ice-cooled suspension of the title compound of Preparation 134 (295.5 g, 1.063 mol) in water (1.2 l), followed by a solution of 50% w/v aqueous sodium hydroxide solution (64 ml, 0.33 mol) at such a rate as to maintain a pH of 6 to 7. The reaction mixture was stirred at below 10° C. for 2 hours, the pH adjusted to 7 and stirring continued at room temperature for 18 hours. Next, the pH was adjusted to 5 using concentrated hydrochloric acid, sodium chloride (240 g) added and the resulting mixture stirred vigorously until solution was achieved. This aqueous solution was extracted with dichloromethane (2×1.05 l), the extracts combined and the dichloromethane removed by distillation whilst replacing it with butan-2-one so as to maintain a constant volume; once a head temperature of about 77° C. had been achieved, the solution was cooled to about 36° C. Methanesulphonic acid (59 ml, 0.909 mol) and more butan-2-one (500 ml) were added dropwise over 1 hour, with gradual heating to 75° C. to enable constant stirring, and the resulting suspension stirred at room temperature for a further 18 hours. Filtration, followed by washing with butan-2-one (500 ml) and drying at 40° C. of the solid thus obtained, provided the methanesulphonate salt of the title compound (383 g, 80%), m.p. 187–188° C. δ (DMSOd$_6$): 0.97 (3H, t), 1.15. (3H, t), 1.75 (2H, m), 3.10 (4H, m), 3.50 (2H, m), 3.70 (2H, m); 4.11 (2H, t), 7.39 (1H, d), 7.86 (1H, m), 7.93 (1H, m).

A portion (20 g) of this salt was dissolved in water (100 ml), then the pH of the stirred solution adjusted to 5.3 using 5M aqueous sodium hydroxide solution and sodium chloride (26 g) added. Next 4-methylpentan-2-one (200 ml) was added, then the resulting mixture vigorously stirred for 30 minutes and filtered. The solid thus obtained was dried to yield the crude product (10 g, 64%), m.p. 83–90° C., crystallisation of a sample of which from butan-2-one:acetone provided the pure title compound, m.p. 143–145° C. δ (DMSOd$_6$): 0.91 (3H, t), 0.99 (3H, t), 1.74 (2H, m), 2.30 (2H, q), 2.45 (4H, m), 2.85 (4H, m), 4.09 (2H, t), 7.32 (1H, d), 7.70 (1H, d), 7.87 (1H, s). LRMS: m/z 357 (M+1)$^+$.

Preparation 136

3-Ethyl-4-[5-(4-ethylpiperazin-1-ylsulphonyl)-2-n-propoxybenzamido]-2-(pyridin-2-yl)methylpyrazole-5-carboxamide A stirred mixture of the title compound of Preparation 135 (356.5 g, 1.0 mol) and butan-2-one (2.85 l) was heated under reflux and then distilled at atmospheric pressure until a substantial portion (1.08 l) of solvent had been removed. The resulting solution was cooled to room temperature under nitrogen and 97% N,N-carbonyidiimidazole (163.9 g, 0.98 mol) added over 2 hours, using an Archimedean screw and washing-in with butan-2-one (100 ml). The mixture was heated to reflux temperature over 1 hour, stirred for a further 30 minutes, allowed to cool and stirred at room temperature for a further 18 hours. Next, the title compound of Preparation 131 (245.3 g, 1.0 mol) was washed in using butan-2-one (20 ml) and the reaction mixture stirred under reflux for 32 hours and then at room temperature for 18 hours. The resulting solid was collected, washed twice with butan-2-one (300 ml. then 150 ml), dried under suction and then stirred with water (1.725 l) for 30 minutes. Filtration gave a further solid which was washed with water (215 ml) and dried at 55° C. to furnish the title compound (385.1 g, 66%) as an off-white solid, m.p. 191–192° C. Found: C,57.43; H, 6.38; N,16.69. C$_{28}$H$_{37}$N$_7$O$_5$S requires C,57.62; H, 6.39; N, 16.80. δ (CDCl$_3$): 1.05 (9H, m), 2.04, (2H, m), 2.38 (2H, q), 2.50 (4H, m), 2.88 (2H, q). 3.05 (4H, m), 4.29 (2H, t), 5.25 (1H, s), 5.47 (2H, s), 6.68 (1H, s), 6.92 (1H, d), 7.12 (1H, d), 7.22 (1H, m), 7.66 (1H, m), 7.86 (1H, d), 8.60 (2H, m), 10.36 (1H, s). LRMS: m/z 584 (M+1)$^+$.

Biological Activity

The following Table illustrates the in vitro activities for a range of the compounds of the invention as inhibitors of cGMP PDE5.

TABLE

| EXAMPLE NO. | IC$_{50}$ (nM) |
| --- | --- |
| 4 | 2.2 |
| 7 | 2.6 |
| 31 | 4.0 |
| 77 | 7.1 |
| 41 | 3.9 |
| 87 | 12.0 |
| 100 | 1.9 |
| 108 | 2.1 |
| 117 | 3.2 |
| 125 | 2.8 |
| 126 | 9.2 |
| 129 | 6.5 |

Safety Profile

Several compounds of the invention have been tested at doses of up to 3 mg/kg i.v. in mouse and at 0.5 mg/kg i.v. and 1 mg/kg p.o. in dog, with no untoward effects being observed.

What is claimed is:

1. A compound of formula (XI):

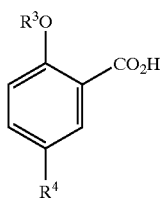

(XI)

wherein $R^3$ is $C_1$ to $C_6$ alkyl optionally substituted with $C_1$–$C_4$ alkoxy;

$R^4$ is $SO_2NR^7R^8$;

$R^7$ and $R^8$, together with the nitrogen atom to which they are attached, form a 4-$R^{10}$-piperazinyl group; and $R^{10}$ is H or $C_1$ to $C_4$ alkyl optionally substituted with OH, $C_1$ to $C_4$ alkoxy or $CONH_2$;

with the proviso that when $R^3$ is ethyl, $R^4$ is not 4-methylpiperizin-1-ylsulfonyl.

2. A process for the preparation of a compound of formula (IXA) or (IXB):

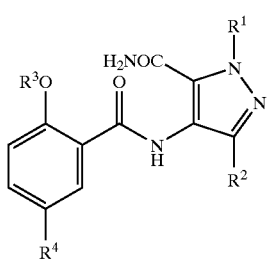

(IXA)

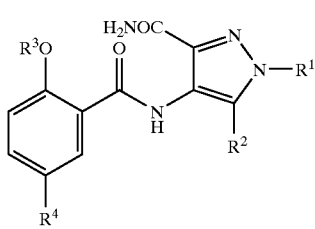

(IXB)

comprising reacting a compound of formula (XA) or (XB) respectively:

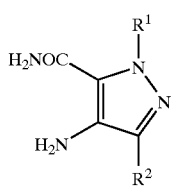

(XA)

(XB)

with a compound of formula (XI):

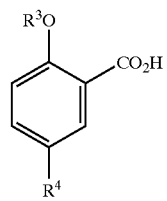

(XI)

wherein $R^1$ is $C_1$ to $C_3$ alkyl substituted with $C_3$ to $C_6$ cycloalkyl, $CONR^5R^6$ or a N-linked heterocyclic group selected from pyrazolyl, imidazolyl, triazolyl, pyrrolidinyl, piperidinyl, morpholinyl and 4-$R^9$-piperazinyl; $(CH_2)_n$Het or $(CH_2)_n$Ar;

$R^2$ is $C_1$ to $C_6$ alkyl;

$R^3$ is $C_1$ to $C_6$ alkyl optionally substituted with $C_1$–$C_4$ alkoxy;

$R^4$ is $SO_2NR^7R^8$;

$R^5$ and $R^6$ are each independently selected from H and $C_1$ to $C_4$ aikyl optionally substituted with $C_1$ to $C_4$ alkoxy, or, together with the nitrogen atom to which they are attached, form a pyrrolidinyl, piperidinyl, morpholinyl or 4-$R^9$-piperazinyl group;

$R^7$ and $R^8$, together with the nitrogen atom to which they are attached, form a 4-$R^{10}$-piperazinyl group;

$R^9$ is $C_1$ to $C_4$ alkyl;

$R^{10}$ is H or $C_1$ to $C_4$ alkyl optionally substituted with OH, $C_1$ to $C_4$ alkoxy or $CONH_2$;

Het is a C-linked 6-membered heterocydic group containing one or two nitrogen atoms as the only heteroatoms therein, optionally in the form of its mono-N-oxide, or a C-linked 5-membered heterocyclic group containing from one to four heteroatoms selected from nitrogen, oxygen and sulphur, wherein either of said heterocyclic groups is optionally substituted with one or two substituents selected from $C_1$ to $C_4$ alkyl optionally substituted with $C_1$ to $C_4$ alkoxy, $C_1$ to $C_4$ alkoxy, halo and $NH_2$;

Ar is phenyl optionally substituted with one or two substituents selected from $C_1$ to $C_4$ alkyl, $C_1$ to $C_4$ alkoxy, halo, CN, $CONH_2$, $NO_2$, $NH_2$, $NHSO_2$ ($C_1$ to $C_4$ alkyl) and $SO_2NH_2$;

and n is 0 or 1.

* * * * *